United States Patent
Kaiser et al.

(10) Patent No.: US 8,088,130 B2
(45) Date of Patent: Jan. 3, 2012

(54) METHOD AND APPARATUS FOR COUPLING SOFT TISSUE TO A BONE

(75) Inventors: Ryan A. Kaiser, Leesburg, IN (US);
Gregory J. Denham, Warsaw, IN (US);
Kevin T. Stone, Winona Lake, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 136 days.

(21) Appl. No.: 12/474,802

(22) Filed: May 29, 2009

(65) Prior Publication Data
US 2009/0312776 A1 Dec. 17, 2009

Related U.S. Application Data

(63) Continuation-in-part of application No. 11/541,506, filed on Sep. 29, 2006, now Pat. No. 7,601,165, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned, and a continuation-in-part of application No. 12/196,407, filed on Aug. 22, 2008, and a continuation-in-part of application No. 12/196,410, filed on Aug. 22, 2008, and a continuation-in-part of application No. 12/196,405, filed on Aug. 22, 2008, and a continuation-in-part of application No. 11/541,505, filed on Sep. 29, 2006, now Pat. No. 7,658,751.

(51) Int. Cl.
*A61B 17/10* (2006.01)
(52) U.S. Cl. ...................................................... 606/139
(58) Field of Classification Search .................. 606/74, 606/103, 139, 223–225, 228, 232; 600/29–30, 600/37; 52/22; 24/115 H
See application file for complete search history.

(56) References Cited

U.S. PATENT DOCUMENTS 26,501 A 10/1859 Kendrick et al.
(Continued)

FOREIGN PATENT DOCUMENTS
AU 4957264 3/1966
(Continued)

OTHER PUBLICATIONS

"Do your next distal tendon repair with . . . The Lubbers Technique", Teno Fix® brochure, 2003 (2 pages) Ortheon® Medical.

(Continued)

*Primary Examiner* — Darwin Erezo
*Assistant Examiner* — Son Dang
(74) *Attorney, Agent, or Firm* — Harness, Dickey

(57) ABSTRACT

A method and apparatus for coupling a soft tissue implant into a locking cavity formed within a bone is disclosed. The apparatus includes a member to pull the soft tissue implant into a femoral tunnel. The member includes a suture having first and second ends which are passed through first and second openings associated with the longitudinal passage to form a pair of loops. Portions of the suture lay parallel to each other within the suture. Application of tension onto the suture construction causes retraction of the soft tissue implant into the femoral tunnel.

23 Claims, 43 Drawing Sheets

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 0,268,407 A | 12/1882 | Hughes |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |

| | | | | | |
|---|---|---|---|---|---|
| 4,235,238 A | 11/1980 | Ogiu et al. | 4,738,255 A | 4/1988 | Goble et al. |
| 4,237,779 A | 12/1980 | Kunreuther | 4,741,330 A | 5/1988 | Hayhurst |
| 4,243,037 A | 1/1981 | Smith | 4,741,336 A | 5/1988 | Failla et al. |
| 4,249,525 A | 2/1981 | Krzeminski | 4,744,353 A | 5/1988 | McFarland |
| 4,263,913 A | 4/1981 | Malmin | 4,744,793 A | 5/1988 | Parr et al. |
| 4,265,246 A | 5/1981 | Barry | 4,750,492 A | 6/1988 | Jacobs |
| 4,273,117 A | 6/1981 | Neuhauser et al. | 4,760,843 A | 8/1988 | Fischer et al. |
| 4,275,717 A | 6/1981 | Bolesky | 4,760,844 A | 8/1988 | Kyle |
| 4,287,807 A | 9/1981 | Pacharis et al. | 4,760,848 A | 8/1988 | Hasson |
| 4,291,698 A | 9/1981 | Fuchs et al. | 4,772,261 A | 9/1988 | Von Hoff et al. |
| 4,301,551 A | 11/1981 | Dore et al. | 4,772,286 A | 9/1988 | Goble et al. |
| 4,312,337 A | 1/1982 | Donohue | 4,773,910 A | 9/1988 | Chen et al. |
| 4,316,469 A | 2/1982 | Kapitanov et al. | 4,775,380 A | 10/1988 | Seedhom et al. |
| 4,326,531 A | 4/1982 | Shimonaka et al. | 4,776,328 A | 10/1988 | Frey et al. |
| 4,345,601 A | 8/1982 | Fukuda | 4,781,190 A | 11/1988 | Lee et al. |
| 4,349,027 A | 9/1982 | DiFrancesco | 4,784,126 A | 11/1988 | Hourahane et al. |
| 4,388,921 A | 6/1983 | Sutter et al. | 4,787,882 A | 11/1988 | Claren et al. |
| 4,400,833 A | 8/1983 | Kurland | 4,790,297 A | 12/1988 | Luque et al. |
| 4,402,445 A | 9/1983 | Green | 4,793,363 A | 12/1988 | Ausherman et al. |
| 4,409,974 A | 10/1983 | Freedland | 4,809,695 A | 3/1989 | Gwathmey et al. |
| 4,438,769 A | 3/1984 | Pratt et al. | 4,813,406 A | 3/1989 | Ogle, II |
| 4,441,489 A | 4/1984 | Evans et al. | 4,823,794 A | 4/1989 | Pierce |
| 4,454,875 A | 6/1984 | Pratt et al. | 4,828,562 A | 5/1989 | Kenna |
| 4,462,395 A | 7/1984 | Johnson | 4,832,026 A | 5/1989 | Jones |
| 4,463,753 A | 8/1984 | Gustilo | 4,834,098 A | 5/1989 | Jones |
| 4,473,102 A | 9/1984 | Ohman et al. | 4,838,282 A | 6/1989 | Strasser et al. |
| 4,484,570 A | 11/1984 | Sutter et al. | 4,841,960 A | 6/1989 | Garner |
| 4,489,446 A | 12/1984 | Reed | 4,851,005 A | 7/1989 | Hunt et al. |
| 4,493,323 A | 1/1985 | Albright et al. | 4,858,608 A | 8/1989 | McQuilkin et al. |
| 4,496,468 A | 1/1985 | House et al. | 4,860,513 A | 8/1989 | Whitman |
| 4,505,274 A | 3/1985 | Speelman | 4,863,383 A | 9/1989 | Grafelmann et al. |
| 4,509,516 A | 4/1985 | Richmond | 4,870,957 A | 10/1989 | Goble et al. |
| 4,531,522 A | 7/1985 | Bedi et al. | 4,873,976 A | 10/1989 | Schreiber |
| 4,532,926 A | 8/1985 | O'Holla | 4,887,601 A | 12/1989 | Richards |
| 4,534,350 A | 8/1985 | Golden et al. | 4,890,615 A | 1/1990 | Caspari et al. |
| 4,535,764 A | 8/1985 | Ebert | 4,893,619 A | 1/1990 | Dale et al. |
| 4,537,185 A | 8/1985 | Stednitz | 4,893,974 A | 1/1990 | Fischer et al. |
| 4,549,545 A | 10/1985 | Levy | 4,895,148 A | 1/1990 | Bays et al. |
| 4,549,652 A | 10/1985 | Free | 4,896,668 A | 1/1990 | Popoff et al. |
| 4,561,432 A | 12/1985 | Mazor | 4,898,156 A | 2/1990 | Gatturna et al. |
| 4,564,007 A | 1/1986 | Coombs et al. | 4,899,743 A | 2/1990 | Nicholson et al. |
| 4,570,623 A | 2/1986 | Ellison et al. | 4,901,721 A | 2/1990 | Hakki |
| 4,573,844 A | 3/1986 | Smith | 4,923,461 A | 5/1990 | Caspari et al. |
| 4,576,608 A | 3/1986 | Homsy | 4,927,421 A | 5/1990 | Goble et al. |
| 4,584,722 A | 4/1986 | Levy et al. | 4,946,468 A | 8/1990 | Li |
| 4,590,928 A | 5/1986 | Hunt et al. | 4,950,270 A | 8/1990 | Bowman et al. |
| 4,595,007 A | 6/1986 | Mericle | 4,950,285 A | 8/1990 | Wilk |
| 4,596,249 A | 6/1986 | Freda et al. | 4,960,381 A | 10/1990 | Niznick |
| 4,602,635 A | 7/1986 | Mulhollan et al. | 4,961,741 A | 10/1990 | Hayhurst |
| 4,602,636 A | 7/1986 | Noiles | 4,968,315 A | 11/1990 | Gatturna |
| 4,604,997 A | 8/1986 | De Bastiani et al. | 4,968,317 A | 11/1990 | Tormala et al. |
| 4,605,414 A | 8/1986 | Czajka | 4,969,886 A | 11/1990 | Cziffer et al. |
| 4,616,650 A | 10/1986 | Green et al. | 4,976,736 A | 12/1990 | White et al. |
| 4,621,640 A | 11/1986 | Mulhollan et al. | 4,978,350 A | 12/1990 | Wagenknecht et al. |
| 4,624,254 A | 11/1986 | McGarry et al. | 4,979,956 A | 12/1990 | Silvestrini |
| 4,632,100 A | 12/1986 | Somers et al. | 4,983,176 A | 1/1991 | Cushman et al. |
| 4,635,637 A | 1/1987 | Schreiber | 4,988,351 A | 1/1991 | Paulos et al. |
| 4,636,121 A | 1/1987 | Miller | 4,994,074 A | 2/1991 | Bezwada et al. |
| 4,641,652 A | 2/1987 | Hutterer et al. | 4,997,433 A | 3/1991 | Goble et al. |
| 4,649,952 A | 3/1987 | Jobe | 5,002,550 A | 3/1991 | Li |
| 4,653,486 A | 3/1987 | Coker | 5,002,562 A | 3/1991 | Oberlander |
| 4,653,487 A | 3/1987 | Maale | 5,007,921 A | 4/1991 | Brown |
| 4,653,489 A | 3/1987 | Tronzo | 5,030,224 A | 7/1991 | Wright et al. |
| 4,655,777 A | 4/1987 | Dunn et al. | 5,037,422 A | 8/1991 | Hayhurst et al. |
| 4,662,068 A | 5/1987 | Polonsky | 5,041,129 A | 8/1991 | Hayhurst et al. |
| 4,667,662 A | 5/1987 | Titone et al. | 5,046,513 A | 9/1991 | Gatturna et al. |
| 4,667,675 A | 5/1987 | Davis | 5,047,030 A | 9/1991 | Draenert et al. |
| 4,669,473 A | 6/1987 | Richards et al. | 5,053,046 A | 10/1991 | Janese |
| 4,683,895 A | 8/1987 | Pohndorf | 5,053,047 A | 10/1991 | Yoon |
| 4,688,561 A | 8/1987 | Reese | 5,059,201 A | 10/1991 | Asnis |
| 4,690,169 A | 9/1987 | Jobe | 5,059,206 A | 10/1991 | Winters |
| 4,705,040 A | 11/1987 | Mueller et al. | 5,061,277 A | 10/1991 | Carpentier et al. |
| 4,708,132 A | 11/1987 | Silvestrini | 5,062,344 A | 11/1991 | Gerker |
| 4,716,893 A | 1/1988 | Fischer et al. | 5,062,843 A | 11/1991 | Mahony, III |
| 4,719,671 A | 1/1988 | Ito et al. | 5,074,874 A | 12/1991 | Yoon et al. |
| 4,719,917 A | 1/1988 | Barrows et al. | 5,078,731 A | 1/1992 | Hayhurst |
| 4,723,540 A | 2/1988 | Gilmer, Jr. | 5,078,843 A | 1/1992 | Pratt |
| 4,724,839 A | 2/1988 | Bedi et al. | 5,084,050 A | 1/1992 | Draenert et al. |
| 4,728,332 A | 3/1988 | Albrektsson et al. | 5,084,058 A | 1/1992 | Li |

| | | | | | |
|---|---|---|---|---|---|
| 5,085,661 A | 2/1992 | Moss | 5,354,298 A | 10/1994 | Lee et al. |
| 5,087,263 A | 2/1992 | Li | 5,356,413 A | 10/1994 | Martins et al. |
| 5,092,866 A | 3/1992 | Breard et al. | 5,358,511 A | 10/1994 | Gatturna et al. |
| 5,098,435 A | 3/1992 | Stednitz et al. | 5,360,431 A | 11/1994 | Puno et al. |
| 5,100,415 A | 3/1992 | Hayhurst | 5,362,294 A | 11/1994 | Seitzinger |
| 5,100,417 A | 3/1992 | Cerier et al. | 5,364,400 A | 11/1994 | Rego, Jr. et al. |
| 5,116,337 A | 5/1992 | Johnson | 5,368,599 A | 11/1994 | Hirsch et al. |
| 5,116,373 A | 5/1992 | Jakob et al. | 5,370,661 A | 12/1994 | Branch |
| 5,116,375 A | 5/1992 | Hofmann | 5,370,662 A | 12/1994 | Stone et al. |
| 5,123,913 A | 6/1992 | Wilk et al. | 5,372,146 A | 12/1994 | Branch |
| 5,123,914 A | 6/1992 | Cope | 5,372,604 A | 12/1994 | Trott |
| 5,127,785 A | 7/1992 | Faucher et al. | 5,372,821 A | 12/1994 | Badylak et al. |
| 5,129,901 A | 7/1992 | Decoste | 5,374,268 A | 12/1994 | Sander |
| 5,129,902 A | 7/1992 | Goble et al. | 5,379,492 A | 1/1995 | Glesser |
| 5,129,904 A | 7/1992 | Illi et al. | 5,383,878 A | 1/1995 | Roger et al. |
| 5,129,906 A | 7/1992 | Ross et al. | 5,383,904 A | 1/1995 | Totakura et al. |
| 5,139,499 A | 8/1992 | Small et al. | 5,391,171 A | 2/1995 | Schmieding |
| 5,139,520 A | 8/1992 | Rosenberg | 5,391,176 A | 2/1995 | de la Torre |
| 5,143,498 A | 9/1992 | Whitman | 5,393,302 A | 2/1995 | Clark et al. |
| 5,147,362 A | 9/1992 | Goble | RE34,871 E | 3/1995 | McGuire et al. |
| 5,149,329 A | 9/1992 | Richardson | 5,397,356 A | 3/1995 | Goble et al. |
| 5,152,790 A | 10/1992 | Rosenberg et al. | 5,403,328 A | 4/1995 | Shallman |
| 5,154,189 A | 10/1992 | Oberlander | 5,403,329 A | 4/1995 | Hinchcliffe |
| 5,156,616 A | 10/1992 | Meadows et al. | 5,403,348 A | 4/1995 | Bonutti |
| 5,163,960 A | 11/1992 | Bonutti | 5,417,691 A | 5/1995 | Hayhurst |
| D331,626 S | 12/1992 | Hayhurst et al. | 5,417,712 A | 5/1995 | Whittaker et al. |
| 5,169,400 A | 12/1992 | Muhling et al. | 5,423,819 A | 6/1995 | Small et al. |
| 5,176,682 A | 1/1993 | Chow | 5,423,823 A | 6/1995 | Schmieding |
| 5,178,629 A | 1/1993 | Kammerer | 5,423,860 A | 6/1995 | Lizardi et al. |
| 5,183,458 A | 2/1993 | Marx | 5,425,733 A | 6/1995 | Schmieding |
| 5,192,282 A | 3/1993 | Draenert et al. | 5,425,766 A | 6/1995 | Bowald et al. |
| 5,197,987 A | 3/1993 | Koch et al. | 5,433,751 A | 7/1995 | Christel et al. |
| 5,203,784 A | 4/1993 | Ross et al. | 5,437,680 A | 8/1995 | Yoon |
| 5,203,787 A | 4/1993 | Noblitt et al. | 5,439,684 A | 8/1995 | Prewett et al. |
| 5,207,679 A | 5/1993 | Li | 5,443,468 A | 8/1995 | Johnson |
| 5,209,753 A | 5/1993 | Biedermann et al. | 5,443,482 A | 8/1995 | Stone et al. |
| 5,209,805 A | 5/1993 | Spraggins | 5,443,483 A | 8/1995 | Kirsch et al. |
| 5,211,647 A | 5/1993 | Schmieding | 5,443,509 A | 8/1995 | Boucher et al. |
| 5,211,650 A | 5/1993 | Noda | 5,445,833 A | 8/1995 | Badylak et al. |
| 5,214,987 A | 6/1993 | Fenton, Sr. | 5,447,512 A | 9/1995 | Wilson et al. |
| 5,219,359 A | 6/1993 | McQuilkin et al. | 5,451,203 A | 9/1995 | Lamb |
| 5,222,976 A | 6/1993 | Yoon | 5,454,811 A | 10/1995 | Huebner |
| 5,224,946 A | 7/1993 | Hayhurst et al. | 5,456,685 A | 10/1995 | Huebner |
| 5,230,699 A | 7/1993 | Grasinger | 5,456,722 A | 10/1995 | McLeod et al. |
| 5,232,436 A | 8/1993 | Janevski | 5,458,601 A | 10/1995 | Young, Jr. et al. |
| 5,234,435 A | 8/1993 | Seagrave, Jr. | 5,458,604 A | 10/1995 | Schmieding |
| 5,235,238 A | 8/1993 | Nomura et al. | 5,462,560 A | 10/1995 | Stevens |
| 5,236,445 A | 8/1993 | Hayhurst et al. | 5,464,426 A | 11/1995 | Bonutti |
| 5,236,461 A | 8/1993 | Forte | 5,464,427 A | 11/1995 | Curtis et al. |
| 5,242,447 A | 9/1993 | Borzone | 5,464,440 A | 11/1995 | Johansson et al. |
| 5,246,441 A | 9/1993 | Ross et al. | 5,466,237 A | 11/1995 | Byrd, III et al. |
| 5,249,899 A | 10/1993 | Wilson | 5,467,786 A | 11/1995 | Allen et al. |
| 5,258,015 A | 11/1993 | Li et al. | 5,470,334 A | 11/1995 | Ross et al. |
| 5,258,016 A | 11/1993 | DiPoto et al. | 5,470,337 A | 11/1995 | Moss |
| 5,258,040 A | 11/1993 | Bruchman et al. | 5,470,338 A | 11/1995 | Whitfield et al. |
| 5,268,001 A | 12/1993 | Nicholson et al. | 5,472,452 A | 12/1995 | Trott |
| 5,269,160 A | 12/1993 | Wood | 5,474,565 A | 12/1995 | Trott |
| 5,269,783 A | 12/1993 | Sander | 5,474,568 A | 12/1995 | Scott |
| 5,269,809 A | 12/1993 | Hayhurst et al. | 5,474,572 A | 12/1995 | Hayhurst |
| 5,281,422 A | 1/1994 | Badylak et al. | 5,478,344 A | 12/1995 | Stone et al. |
| 5,282,809 A | 2/1994 | Kammerer et al. | 5,478,345 A | 12/1995 | Stone et al. |
| 5,282,832 A | 2/1994 | Toso et al. | 5,480,403 A | 1/1996 | Lee et al. |
| 5,285,040 A | 2/1994 | Brandberg et al. | 5,480,406 A | 1/1996 | Nolan et al. |
| 5,290,217 A | 3/1994 | Campos | 5,484,442 A | 1/1996 | Melker et al. |
| 5,306,301 A | 4/1994 | Graf et al. | 5,486,197 A | 1/1996 | Le et al. |
| 5,312,422 A | 5/1994 | Trott | 5,490,750 A | 2/1996 | Gundy |
| 5,312,438 A | 5/1994 | Johnson | 5,496,331 A | 3/1996 | Xu et al. |
| 5,318,577 A | 6/1994 | Li | 5,496,348 A | 3/1996 | Bonutti |
| 5,318,578 A | 6/1994 | Hasson | 5,500,000 A | 3/1996 | Feagin et al. |
| 5,320,115 A | 6/1994 | Kenna | 5,505,736 A | 4/1996 | Reimels et al. |
| 5,320,626 A | 6/1994 | Schmieding | 5,507,754 A | 4/1996 | Green et al. |
| 5,320,633 A | 6/1994 | Allen et al. | 5,520,691 A | 5/1996 | Branch |
| 5,324,308 A | 6/1994 | Pierce | 5,520,702 A | 5/1996 | Sauer et al. |
| 5,334,204 A | 8/1994 | Clewett et al. | 5,522,817 A | 6/1996 | Sander et al. |
| 5,336,229 A | 8/1994 | Noda | 5,522,820 A | 6/1996 | Caspari et al. |
| 5,336,231 A | 8/1994 | Adair | 5,522,844 A | 6/1996 | Johnson |
| 5,336,240 A | 8/1994 | Metzler et al. | 5,522,845 A | 6/1996 | Wenstrom, Jr. |
| 5,342,369 A | 8/1994 | Harryman, II | 5,522,846 A | 6/1996 | Bonutti |
| 5,346,462 A | 9/1994 | Barber | 5,524,946 A | 6/1996 | Thompson |

| | | | | | |
|---|---|---|---|---|---|
| 5,527,321 A | 6/1996 | Hinchliffe | 5,707,373 A | 1/1998 | Sevrain et al. |
| 5,527,342 A | 6/1996 | Pietrzak et al. | 5,713,005 A | 1/1998 | Proebsting |
| 5,527,343 A | 6/1996 | Bonutti | 5,713,904 A | 2/1998 | Errico et al. |
| 5,534,012 A | 7/1996 | Bonutti | 5,713,905 A | 2/1998 | Goble et al. |
| 5,540,718 A | 7/1996 | Bartlett | 5,713,921 A | 2/1998 | Bonutti |
| 5,545,178 A | 8/1996 | Kensey et al. | 5,716,359 A | 2/1998 | Ojima et al. |
| 5,545,228 A | 8/1996 | Kambin | 5,716,397 A | 2/1998 | Myers |
| 5,549,613 A | 8/1996 | Goble et al. | 5,718,717 A | 2/1998 | Bonutti |
| 5,549,617 A | 8/1996 | Green et al. | 5,720,747 A | 2/1998 | Burke |
| 5,549,630 A | 8/1996 | Bonutti | 5,720,765 A | 2/1998 | Thal |
| 5,549,631 A | 8/1996 | Bonutti | 5,720,766 A | 2/1998 | Zang et al. |
| 5,562,683 A | 10/1996 | Chan | 5,725,549 A | 3/1998 | Lam |
| 5,562,685 A | 10/1996 | Mollenauer et al. | 5,725,556 A | 3/1998 | Moser et al. |
| 5,562,686 A | 10/1996 | Sauer et al. | 5,725,581 A | 3/1998 | Brångemark et al. |
| 5,569,269 A | 10/1996 | Hart et al. | 5,725,582 A | 3/1998 | Bevan et al. |
| 5,569,305 A | 10/1996 | Bonutti | 5,726,722 A | 3/1998 | Uehara et al. |
| 5,571,090 A | 11/1996 | Sherts | 5,728,107 A | 3/1998 | Zlock et al. |
| 5,571,139 A | 11/1996 | Jenkins, Jr. | 5,728,109 A | 3/1998 | Schulze et al. |
| 5,572,655 A | 11/1996 | Tuljapurkar et al. | 5,728,136 A | 3/1998 | Thal |
| 5,573,286 A | 11/1996 | Rogozinski | 5,733,293 A | 3/1998 | Scirica et al. |
| 5,573,542 A | 11/1996 | Stevens | 5,733,306 A | 3/1998 | Bonutti |
| 5,573,548 A | 11/1996 | Nazre et al. | 5,733,307 A | 3/1998 | Dinsdale |
| 5,577,299 A | 11/1996 | Thompson et al. | 5,735,875 A | 4/1998 | Bonutti et al. |
| 5,578,057 A | 11/1996 | Wenstrom, Jr. | 5,741,259 A | 4/1998 | Chan |
| 5,584,695 A | 12/1996 | Lal Sachdeva et al. | 5,741,281 A | 4/1998 | Martin et al. |
| 5,584,835 A | 12/1996 | Greenfield | 5,743,912 A | 4/1998 | Lahille et al. |
| 5,584,836 A | 12/1996 | Ballintyn et al. | 5,746,751 A | 5/1998 | Sherts |
| 5,584,862 A | 12/1996 | Bonutti | 5,746,752 A | 5/1998 | Burkhart |
| 5,586,986 A | 12/1996 | Hinchliffe | 5,746,754 A | 5/1998 | Chan |
| 5,588,575 A | 12/1996 | Davignon | 5,749,898 A | 5/1998 | Schulze et al. |
| 5,591,180 A | 1/1997 | Hinchliffe | 5,755,729 A | 5/1998 | de la Torre et al. |
| 5,591,181 A | 1/1997 | Stone et al. | 5,766,176 A | 6/1998 | Duncan |
| 5,591,207 A | 1/1997 | Coleman | 5,766,250 A | 6/1998 | Chervitz et al. |
| 5,593,407 A | 1/1997 | Reis et al. | 5,769,894 A | 6/1998 | Ferragamo |
| 5,593,425 A | 1/1997 | Bonutti et al. | 5,769,899 A | 6/1998 | Schwartz et al. |
| 5,601,557 A | 2/1997 | Hayhurst | 5,772,673 A | 6/1998 | Cuny et al. |
| 5,601,559 A | 2/1997 | Melker et al. | 5,776,196 A | 7/1998 | Matsuzaki et al. |
| 5,601,571 A | 2/1997 | Moss | 5,782,862 A | 7/1998 | Bonutti |
| 5,603,716 A | 2/1997 | Morgan et al. | 5,782,864 A | 7/1998 | Lizardi |
| 5,607,429 A | 3/1997 | Hayano et al. | 5,782,866 A | 7/1998 | Wenstrom, Jr. |
| 5,618,290 A | 4/1997 | Toy et al. | 5,785,714 A | 7/1998 | Morgan et al. |
| 5,628,756 A | 5/1997 | Barker, Jr. et al. | 5,792,142 A | 8/1998 | Galitzer |
| 5,628,766 A | 5/1997 | Johnson | 5,792,149 A | 8/1998 | Sherts et al. |
| 5,630,824 A | 5/1997 | Hart | 5,796,127 A | 8/1998 | Hayafuji et al. |
| 5,632,748 A | 5/1997 | Beck, Jr. et al. | 5,797,928 A | 8/1998 | Kogasaka et al. |
| 5,641,256 A | 6/1997 | Gundy | 5,800,407 A | 9/1998 | Eldor et al. |
| 5,643,266 A | 7/1997 | Li | 5,810,824 A | 9/1998 | Chan |
| 5,643,269 A | 7/1997 | Harle et al. | 5,810,848 A | 9/1998 | Hayhurst |
| 5,643,295 A | 7/1997 | Yoon | 5,814,069 A | 9/1998 | Schulze et al. |
| 5,643,320 A | 7/1997 | Lower et al. | 5,814,070 A | 9/1998 | Borzone et al. |
| 5,643,321 A | 7/1997 | McDevitt | 5,814,072 A | 9/1998 | Bonutti |
| 5,645,546 A | 7/1997 | Fard | 5,814,073 A | 9/1998 | Bonutti |
| 5,645,547 A | 7/1997 | Coleman | 5,823,980 A | 10/1998 | Kopfer |
| 5,645,568 A | 7/1997 | Chervitz et al. | 5,824,011 A | 10/1998 | Stone et al. |
| 5,645,588 A | 7/1997 | Graf et al. | 5,843,084 A | 12/1998 | Hart et al. |
| 5,647,874 A | 7/1997 | Hayhurst | 5,845,645 A | 12/1998 | Bonutti |
| 5,649,959 A | 7/1997 | Hannam et al. | 5,846,254 A | 12/1998 | Schulze et al. |
| 5,649,963 A | 7/1997 | McDevitt | 5,848,983 A | 12/1998 | Basaj et al. |
| 5,658,289 A | 8/1997 | Boucher et al. | 5,860,973 A | 1/1999 | Michelson |
| 5,658,299 A | 8/1997 | Hart | 5,868,740 A | 2/1999 | LeVeen et al. |
| 5,658,313 A | 8/1997 | Thal | 5,868,789 A | 2/1999 | Huebner |
| 5,662,658 A | 9/1997 | Wenstrom, Jr. | 5,871,484 A | 2/1999 | Spievack et al. |
| 5,662,663 A | 9/1997 | Shallman | 5,871,486 A | 2/1999 | Huebner et al. |
| 5,665,112 A | 9/1997 | Thal | 5,871,490 A | 2/1999 | Schulze et al. |
| 5,667,513 A | 9/1997 | Torrie et al. | 5,885,294 A | 3/1999 | Pedlick et al. |
| 5,671,695 A | 9/1997 | Schroeder | 5,891,168 A | 4/1999 | Thal |
| 5,674,224 A | 10/1997 | Howell et al. | 5,893,592 A | 4/1999 | Schulze et al. |
| 5,679,723 A | 10/1997 | Cooper et al. | 5,895,395 A | 4/1999 | Yeung |
| 5,681,352 A | 10/1997 | Clancy, III et al. | 5,897,564 A | 4/1999 | Schulze et al. |
| 5,683,419 A | 11/1997 | Thal | 5,897,574 A | 4/1999 | Bonutti |
| 5,688,285 A | 11/1997 | Yamada et al. | 5,899,902 A | 5/1999 | Brown et al. |
| 5,690,676 A | 11/1997 | DiPoto et al. | 5,899,938 A | 5/1999 | Sklar et al. |
| 5,690,678 A | 11/1997 | Johnson | 5,908,421 A | 6/1999 | Beger et al. |
| 5,695,497 A | 12/1997 | Stahelin et al. | 5,908,436 A | 6/1999 | Cuschieri et al. |
| 5,697,929 A | 12/1997 | Mellinger | 5,910,148 A | 6/1999 | Reimels et al. |
| 5,699,657 A * | 12/1997 | Paulson .............. 57/22 | 5,911,721 A | 6/1999 | Nicholson et al. |
| 5,702,397 A | 12/1997 | Goble et al. | 5,918,604 A | 7/1999 | Whelan |
| 5,702,422 A | 12/1997 | Stone | 5,921,986 A | 7/1999 | Bonutti |
| 5,702,462 A | 12/1997 | Oberlander | 5,925,008 A | 7/1999 | Douglas |

| Patent No. | Date | Name |
|---|---|---|
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex et al. |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom et al. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |

| | | |
|---|---|---|
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 * | 1/2003 | Fumex .................. 606/232 |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein et al. |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,066,942 B2 | 6/2006 | Treace |
| 7,066,944 B2 | 6/2006 | Laufer et al. |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,307 B2 | 12/2006 | Scribner et al. |
| 7,153,312 B1 | 12/2006 | Torrie et al. |
| 7,201,722 B2 | 4/2007 | Krueger |
| 7,255,675 B2 | 8/2007 | Gertner et al. |
| 7,261,716 B2 | 8/2007 | Strobel et al. |
| 7,264,634 B2 | 9/2007 | Schmieding |
| 7,285,124 B2 | 10/2007 | Foerster |
| 7,306,417 B2 | 12/2007 | Dorstewitz |
| 7,326,222 B2 | 2/2008 | Dreyfuss et al. |
| 7,390,332 B2 | 6/2008 | Selvitelli et al. |

| Patent No. | Date | Inventor |
|---|---|---|
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0208210 A1 | 11/2003 | Dreyfuss et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0267479 A1 | 12/2005 | Morgan et al. |
| 2005/0267533 A1 | 12/2005 | Gertner |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0253130 A1 | 11/2006 | Wolniewicz |
| 2006/0271192 A1 | 11/2006 | Olsen et al. |

| | | | | | |
|---|---|---|---|---|---|
| 2006/0280768 A1 | 12/2006 | Hwang et al. | EP | 0129442 | 12/1984 |
| 2006/0282085 A1 | 12/2006 | Stone et al. | EP | 0172130 | 2/1986 |
| 2006/0293709 A1 | 12/2006 | Bojarski et al. | EP | 0241240 | 10/1987 |
| 2007/0005080 A1 | 1/2007 | Wolniewicz et al. | EP | 0241792 | 10/1987 |
| 2007/0016305 A1 | 1/2007 | Chudik | EP | 0260970 | 3/1988 |
| 2007/0055255 A1 | 3/2007 | Siegel | EP | 0270704 | 6/1988 |
| 2007/0060922 A1 | 3/2007 | Dreyfuss | EP | 0282789 | 9/1988 |
| 2007/0067025 A1 | 3/2007 | Schwartz | EP | 0315371 | 5/1989 |
| 2007/0073307 A1 | 3/2007 | Scribner et al. | EP | 0317406 | 5/1989 |
| 2007/0078435 A1 | 4/2007 | Stone et al. | EP | 0340159 | 11/1989 |
| 2007/0083236 A1 | 4/2007 | Sikora et al. | EP | 0346183 | 12/1989 |
| 2007/0093847 A1 | 4/2007 | Scribner et al. | EP | 0349173 | 1/1990 |
| 2007/0142838 A1 | 6/2007 | Jordan | EP | 0374088 | 6/1990 |
| 2007/0185532 A1 | 8/2007 | Stone et al. | EP | 0409364 | 1/1991 |
| 2007/0239209 A1 | 10/2007 | Fallman | EP | 0415915 | 3/1991 |
| 2007/0239275 A1 | 10/2007 | Willobee | EP | 0440991 | 8/1991 |
| 2007/0250163 A1 | 10/2007 | Cassani | EP | 0441065 | 8/1991 |
| 2008/0027446 A1 | 1/2008 | Stone et al. | EP | 0451932 | 10/1991 |
| 2008/0046009 A1 | 2/2008 | Albertorio et al. | EP | 0464480 | 1/1992 |
| 2008/0065114 A1 | 3/2008 | Stone et al. | EP | 0497079 | 8/1992 |
| 2008/0082127 A1 | 4/2008 | Stone et al. | EP | 0502509 | 9/1992 |
| 2008/0082128 A1 | 4/2008 | Stone | EP | 0502698 | 9/1992 |
| 2008/0132753 A1 | 6/2008 | Goddard | EP | 520177 | 12/1992 |
| 2008/0132932 A1 | 6/2008 | Hoeppner et al. | EP | 0546726 | 6/1993 |
| 2008/0140092 A1 | 6/2008 | Stone et al. | EP | 0574707 | 12/1993 |
| 2008/0140093 A1 | 6/2008 | Stone et al. | EP | 0582514 | 2/1994 |
| 2008/0161852 A1 | 7/2008 | Kaiser et al. | EP | 0591991 | 4/1994 |
| 2008/0188936 A1 | 8/2008 | Ball et al. | EP | 0598219 | 5/1994 |
| 2008/0255613 A1 | 10/2008 | Kaiser et al. | EP | 0611551 A1 | 8/1994 |
| 2008/0268064 A1 | 10/2008 | Woodell-May | EP | 0627203 | 12/1994 |
| 2008/0269674 A1 | 10/2008 | Stone | EP | 0651979 | 5/1995 |
| 2008/0275477 A1 | 11/2008 | Sterrett et al. | EP | 0669110 | 8/1995 |
| 2008/0312689 A1 | 12/2008 | Denham et al. | EP | 0686373 | 12/1995 |
| 2009/0054928 A1 | 2/2009 | Denham et al. | EP | 0702933 | 3/1996 |
| 2009/0062854 A1 | 3/2009 | Kaiser et al. | EP | 0775473 | 5/1997 |
| 2009/0082805 A1 | 3/2009 | Kaiser et al. | EP | 0913123 | 5/1999 |
| 2009/0177233 A1 | 7/2009 | Malek | EP | 0913131 | 5/1999 |
| 2009/0192468 A1 | 7/2009 | Stone | EP | 99121106 | 10/1999 |
| 2009/0204146 A1 | 8/2009 | Kaiser et al. | EP | 991210527 | 10/1999 |
| 2009/0306711 A1 | 12/2009 | Stone et al. | EP | 0995409 | 4/2000 |
| 2009/0312776 A1 | 12/2009 | Kaiser et al. | EP | 1013229 | 6/2000 |
| 2009/0318961 A1 | 12/2009 | Stone et al. | EP | 1093773 | 4/2001 |
| 2010/0042114 A1 | 2/2010 | Schaffhausen | EP | 1093774 | 4/2001 |
| 2010/0087857 A1 | 4/2010 | Stone et al. | EP | 1555945 | 7/2005 |
| 2010/0145384 A1 | 6/2010 | Stone et al. | FR | 2622790 | 5/1989 |
| 2010/0211075 A1 | 8/2010 | Stone | FR | 2655840 | 6/1991 |
| 2010/0256677 A1 | 10/2010 | Albertorio et al. | FR | 2682867 | 4/1993 |
| 2010/0268275 A1 | 10/2010 | Stone et al. | FR | 2687911 | 9/1993 |
| 2010/0292792 A1 | 11/2010 | Stone et al. | FR | 2688689 | 9/1993 |
| 2010/0305698 A1 | 12/2010 | Metzger et al. | FR | 2704140 | 10/1994 |
| 2010/0305709 A1 | 12/2010 | Metzger et al. | FR | 2717070 | 9/1995 |
| 2010/0312341 A1 | 12/2010 | Kaiser et al. | FR | 2723528 | 2/1996 |
| 2011/0087284 A1 | 4/2011 | Stone et al. | FR | 2744010 | 8/1997 |
| 2011/0098727 A1 | 4/2011 | Kaiser et al. | FR | 2745999 | 9/1997 |
| | | | FR | 2770764 | 5/1999 |
| FOREIGN PATENT DOCUMENTS | | | GB | 401677 | 11/1933 |
| AU | 440266 | 10/1967 | GB | 1413477 | 11/1975 |
| AU | 2223767 | 11/1968 | GB | 1485681 | 9/1977 |
| AU | 5028569 | 8/1970 | GB | 2083751 | 3/1982 |
| AU | 5850469 | 1/1971 | GB | 2118474 | 11/1983 |
| AU | 5963869 | 2/1971 | GB | 2227175 | 7/1990 |
| AU | 1505470 | 11/1971 | GB | 2253147 | 9/1992 |
| AU | 3615171 | 5/1973 | GB | 2312376 | 10/1997 |
| AU | 7110887 | 10/1987 | JP | 5362911 | 5/1978 |
| AU | 639410 | 11/1989 | JP | 5362912 | 5/1978 |
| AU | 651929 | 8/1994 | JP | 5374942 | 6/1978 |
| DE | 2529669 | 3/1976 | JP | 5378230 | 6/1978 |
| DE | 2747312 | 4/1979 | JP | 62159647 | 7/1987 |
| DE | 2818254 | 10/1979 | JP | 62295657 | 12/1987 |
| DE | 2919009 | 11/1979 | JP | 5269160 | 10/1993 |
| DE | 3027138 | 12/1981 | JP | 5300917 | 11/1993 |
| DE | 3225620 | 2/1983 | JP | 751292 | 2/1995 |
| DE | 3136083 | 3/1983 | JP | 10211213 | 8/1998 |
| DE | 233303 | 2/1986 | WO | WO-2005104992 | 12/1899 |
| DE | 4127550 | 2/1993 | WO | WO-8300615 | 3/1983 |
| DE | 4302397 | 7/1993 | WO | WO-8603666 | 7/1986 |
| DE | 29621340 | 5/1998 | WO | WO-8701270 | 3/1987 |
| DE | 19841252 | 3/2000 | WO | WO-8901767 | 3/1989 |
| EP | 0108912 | 5/1984 | WO | WO-8909030 | 10/1989 |

| | | |
|---|---|---|
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03071962 | 9/2003 |
| WO | WO-03077772 | 9/2003 |

OTHER PUBLICATIONS

"Make your next tendon repair an open-and-shut case. The Teno Fix® Tendon Repair System", Teno Fix® brochure, 2003 (2 pages) Ortheon® Medical.

"EZ Loc Femoral Fixation Device," copyright 2005 Arthrotek, Inc. (8 sheets).

"PANALOK Anchor with PDS II and ETHIBOND Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-JOURNAL 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Bio-Intrafix (TCP/PLA & Intrafix, Tibial Soft Tissue Fasteners, by DePuy Mitek, 6 sheets, (date unknown).

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

US 6,238,418, 05/2001, Schwartz et al. (withdrawn)

* cited by examiner

METHOD AND APPARATUS FOR COUPLING SOFT TISSUE TO A BONE

CROSS-REFERENCE TO RELATED APPLICATIONS

This application is a continuation-in-part application of U.S. patent application Ser. No. 11/541,506 filed on Sep. 29, 2006 now U.S. Pat. No. 7,601,165, and is a continuation-in-part application of U.S. patent application Ser. No. 11/541, 505 filed on Sep. 29, 2006 now U.S. Pat. No. 7,658,751, and is a continuation-in-part application of U.S. patent application Ser. No. 12/014,399 filed on Jan. 15, 2008 now U.S. Pat. No. 7,909,851, and is a continuation-in-part application of U.S. patent application Ser. No. 12/014,340 filed on Jan. 15, 2008 now U.S. Pat. No. 7,905,904, and is a continuation-in-part application of U.S. patent application Ser. Nos. 11/935, 681 filed on Nov. 6, 2007 now U.S. Pat. No. 7,905,903, and is a continuation-in-part application of 11/869,440 filed on Oct. 9, 2007 now U.S. Pat. No. 7,857,830, and is a continuation-in-part application of 11/784,821 filed on Apr. 10, 2007, and is a continuation-in-part application of 11/347,661 filed on Feb. 3, 2006 now U.S. Pat. No. 7,749,250, and is a continuation-in-part application of 11/347,662 filed on Feb. 3, 2006. This application is also a continuation-in-part of U.S. patent application Ser. No. 12/196,405 filed on Aug. 22, 2008, U.S. patent application Ser. No. 12/196,407, filed on Aug. 22, 2008, and U.S. patent application Ser. No. 12/196,410, filed on Aug. 22, 2008. The disclosure of the above applications is incorporated herein by reference.

FIELD

The present disclosure relates to method of coupling soft tissue and, more particularly, to a method of coupling soft tissue to a bone.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction in a femoral tunnel is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the femoral tunnel. Soft tissue is then passed through the first and second loops. Tension is applied onto the first and second ends to constrict the first and second loops about the soft tissue.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. A first and second tunnels are formed in first and second bones. A locking member having a first profile which allows insertion of the locking member through the tunnel and a second profile which allows engagement with the positive locking surface upon rotation of the locking member is provided. The suture construction described above is coupled to the locking member. The first and second ends and the first and second loops of the construction and the locking member are threaded through the first and second tunnels. Soft tissue is threaded through the first and second loops so as to engage bearing surfaces on the first and second loops. The locking member is then engaged.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
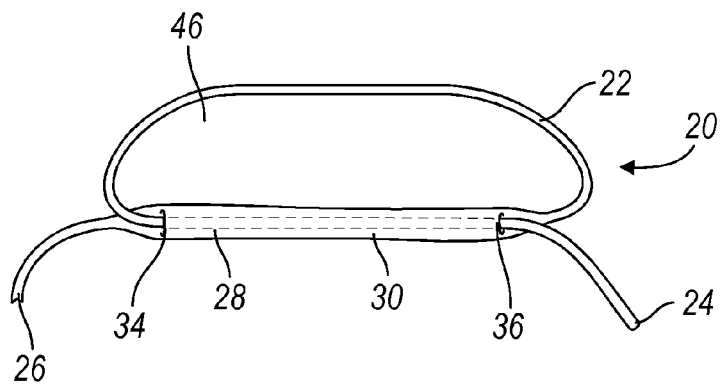
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
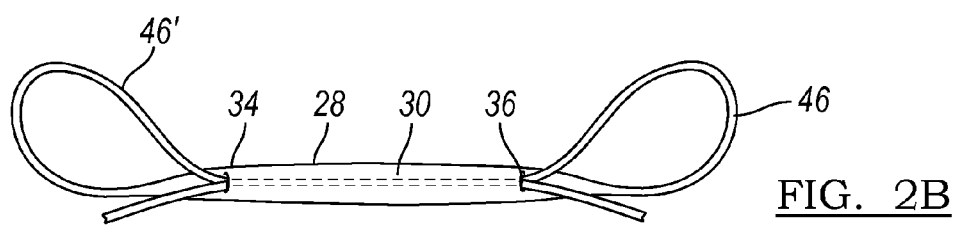
Figure 3:
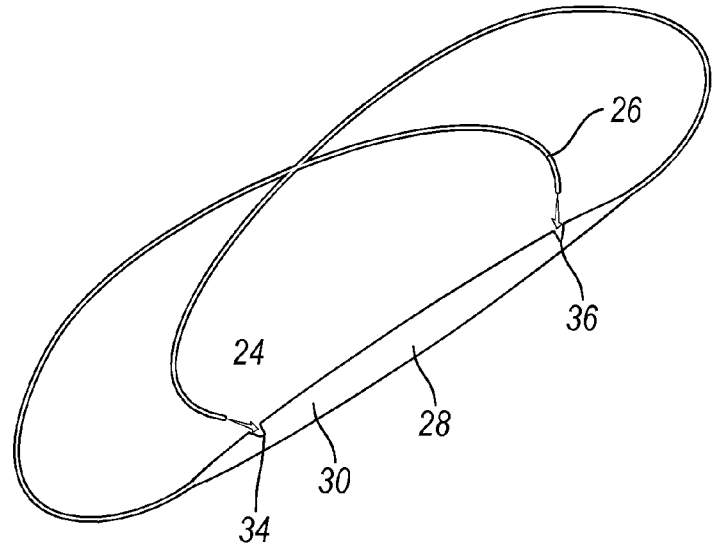
FIG. 3 represents the formation of the suture configuration shown in FIG. 2A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

Figure 4A:
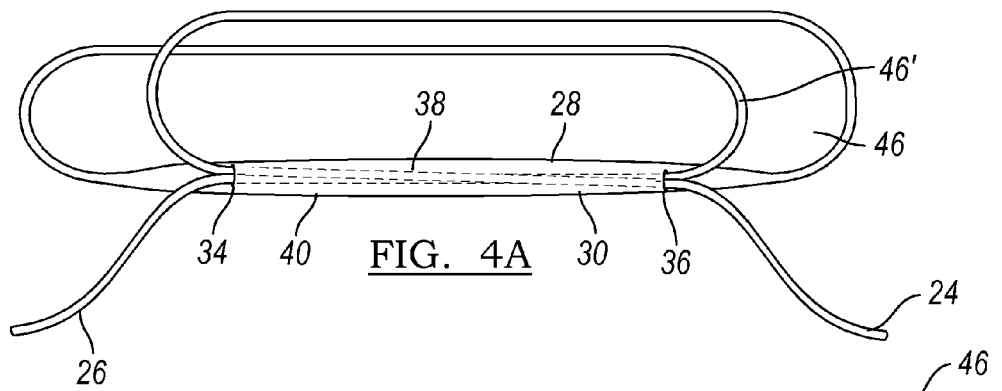
FIGS. 4A and 4B represent alternate suture configurations.
Figure 4B:
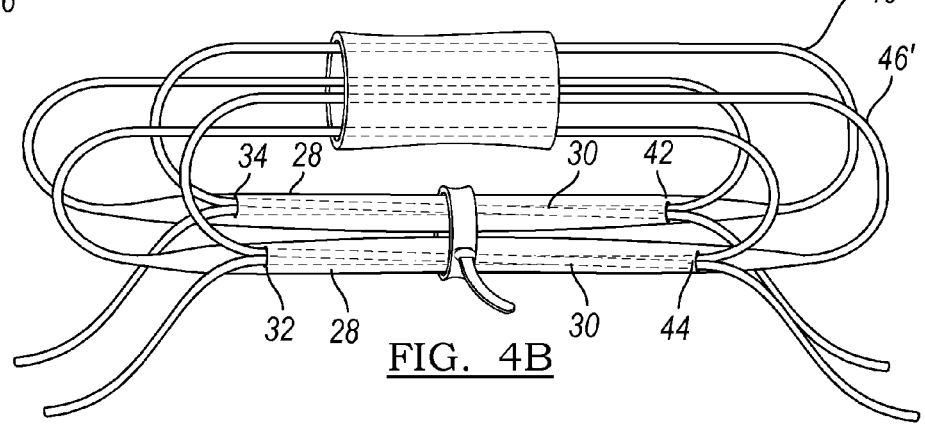

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
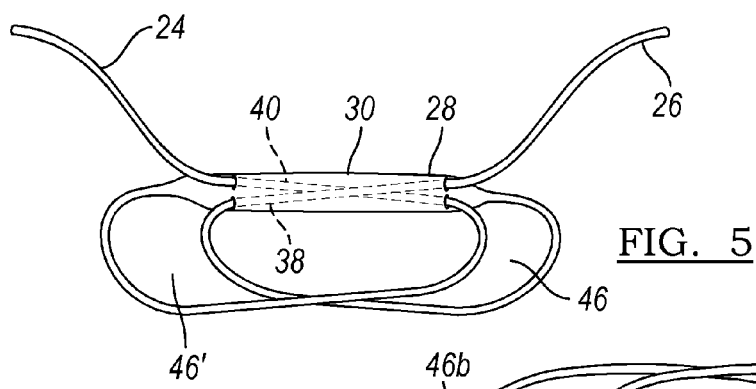
FIGS. 5-7 represent further alternate suture configurations.
Figure 6:
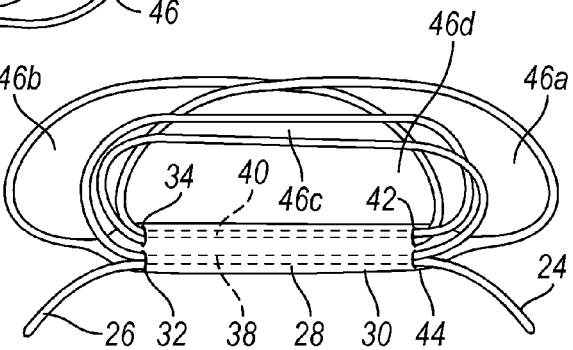
Figure 7:
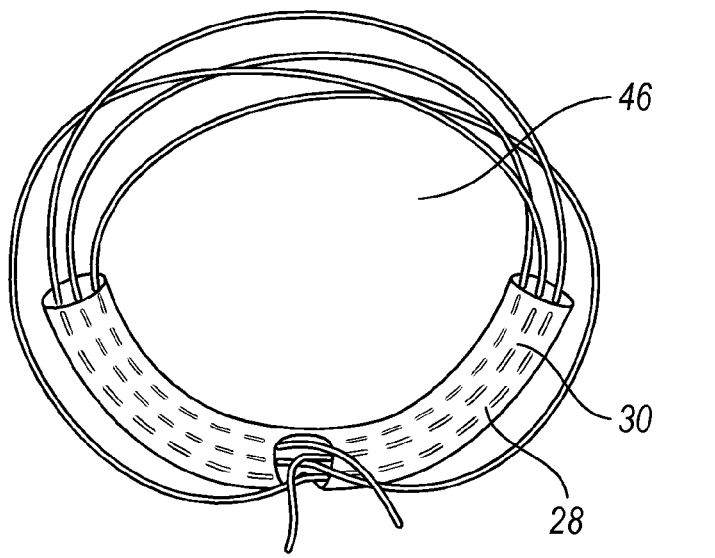
Figure 8:
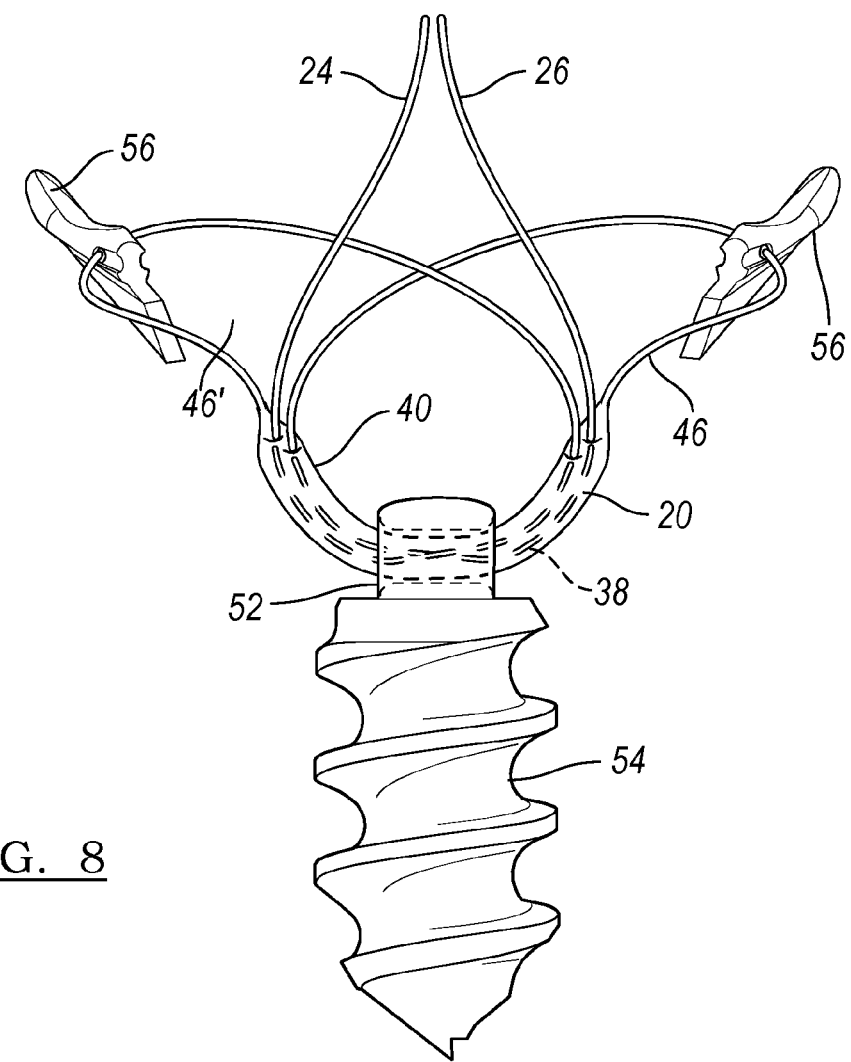
FIG. 8 represents the suture construction according to FIG. 5 coupled to a bone engaging fastener.
Figure 9:
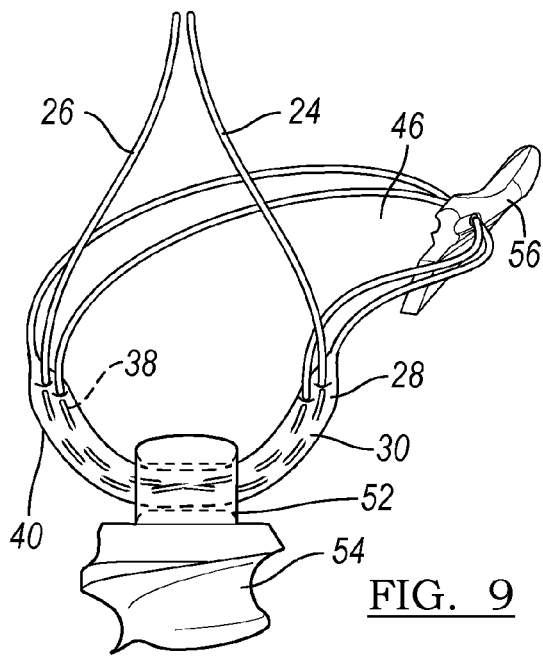
FIGS. 9-11 represent the coupling of the suture construction according to FIG. 5 to a bone screw.
Figure 10:
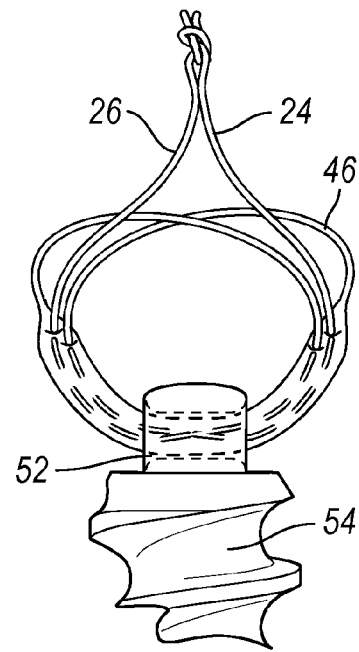

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
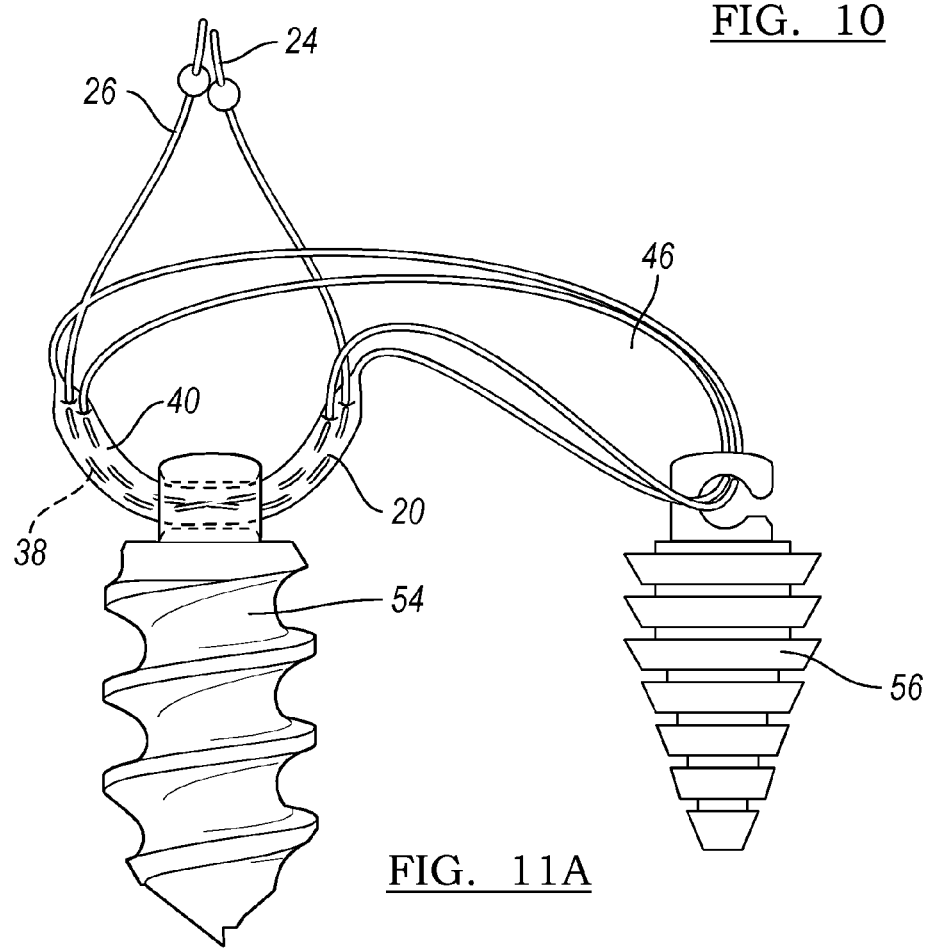
Figure 11B:
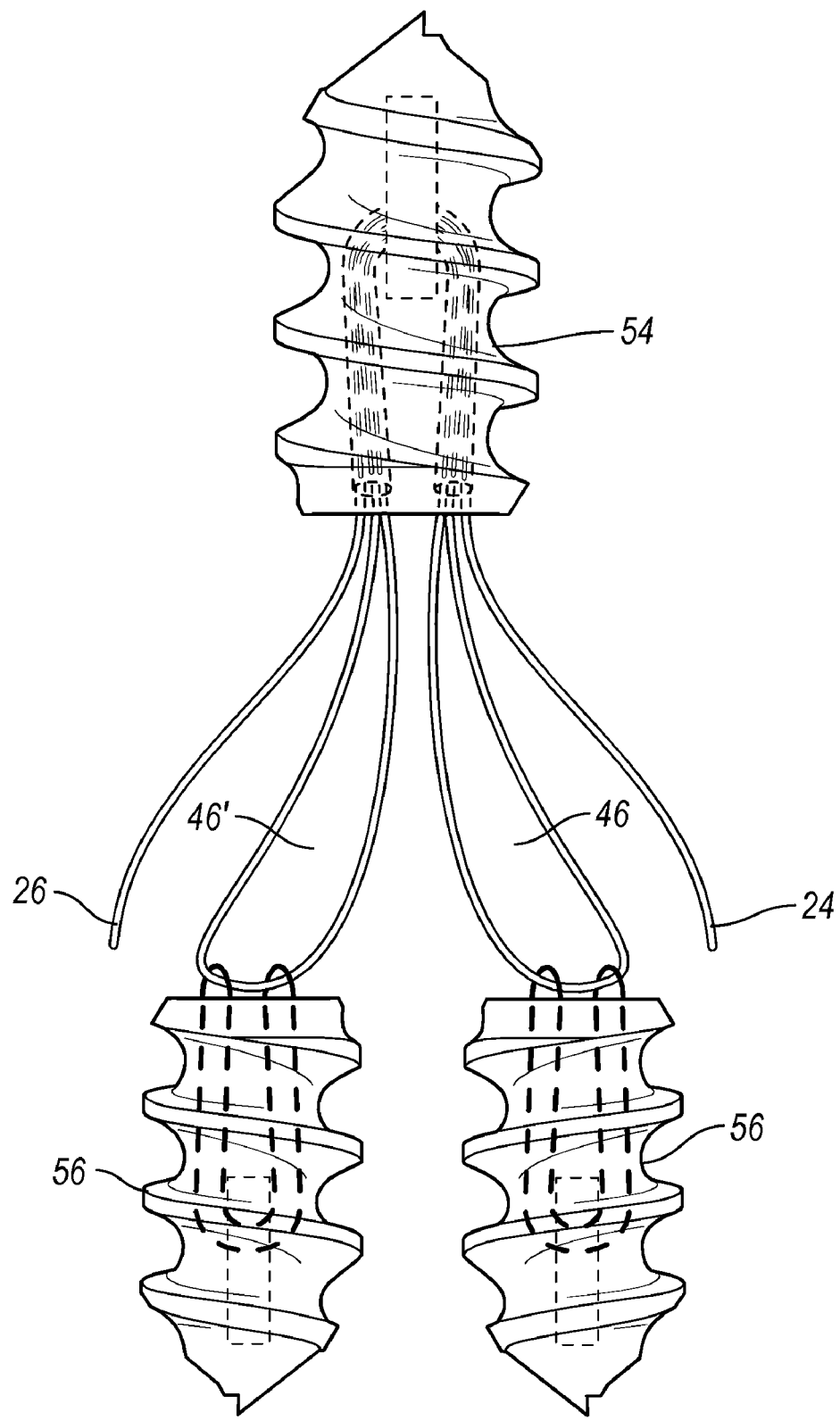

FIG. 11b represents the coupling of the suture construction according to FIG. 2B with a bone fastening member. Coupled to a pair of loops 46 and 46' are tissue fastening members 56. The application of tension to either the first or second end 24 or 26 will tighten the loops 46 or 46' separately.

Figure 12A:
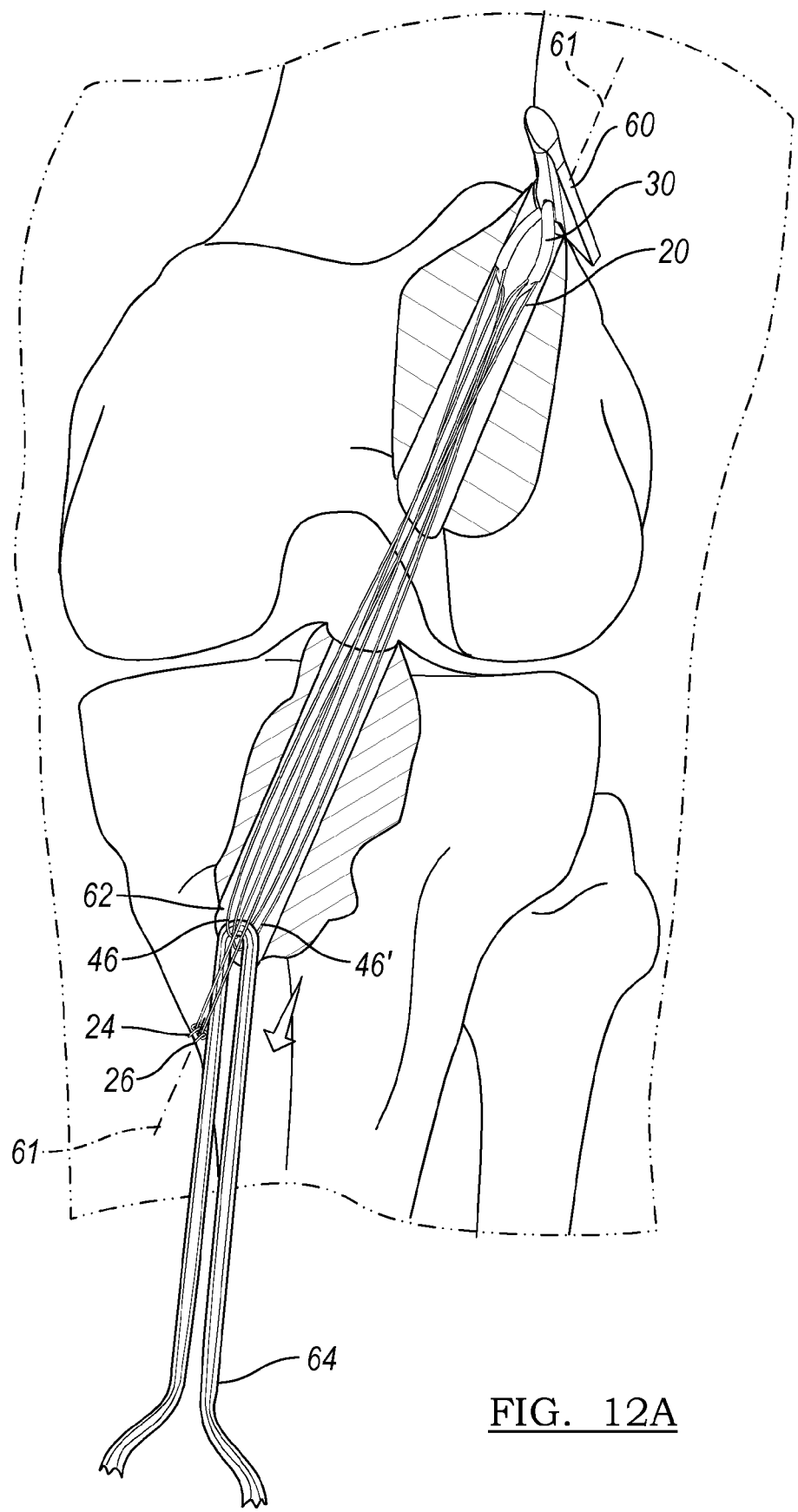
FIGS. 12A-12E represent the coupling of a soft tissue to an ACL replacement in a femoral/humeral reconstruction.
Figure 12B:
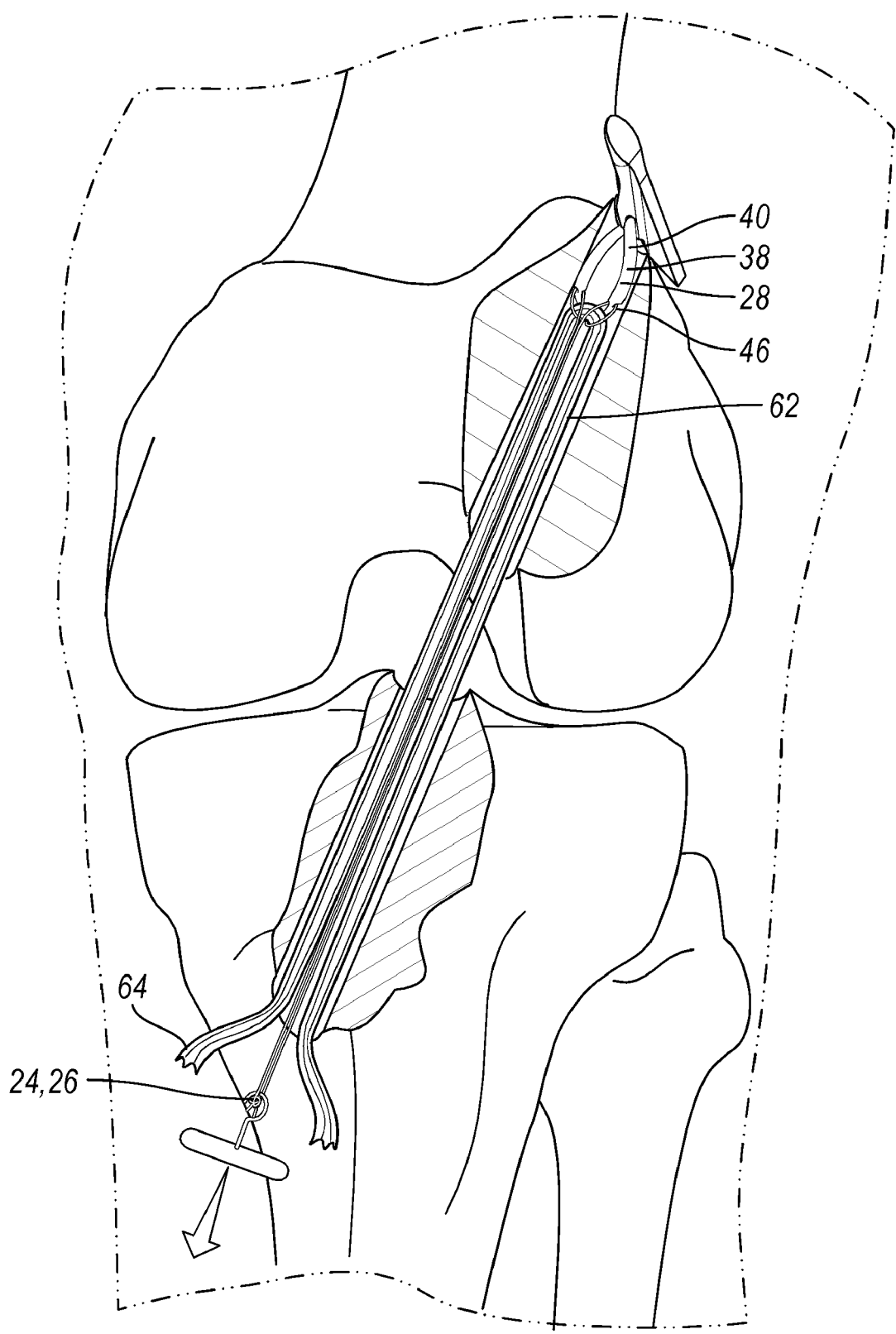

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member or fastener 60. The fixation member 60 can have a first profile which allows insertion of the fixation member 60 through the tunnel and a second profile which allows engagement with a positive locking surface upon rotation. The longitudinal passage portion 30 of the suture construction 20, fixation member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the fixation member 60, application of forces to the ends 24, 26 may reduce the seating force applied by the fixation member 60 onto the bone.

Figure 12C:
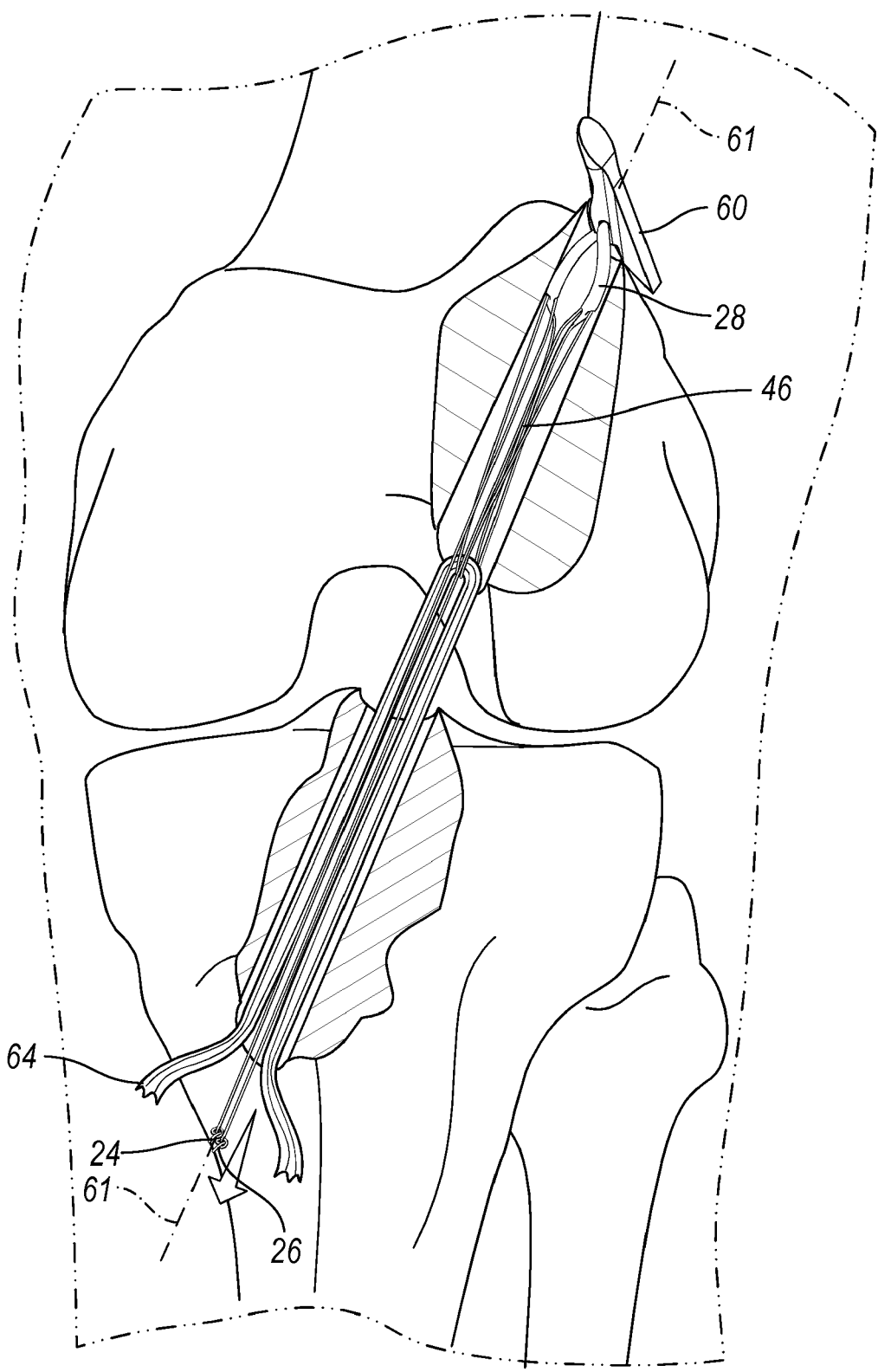
Figure 12D:
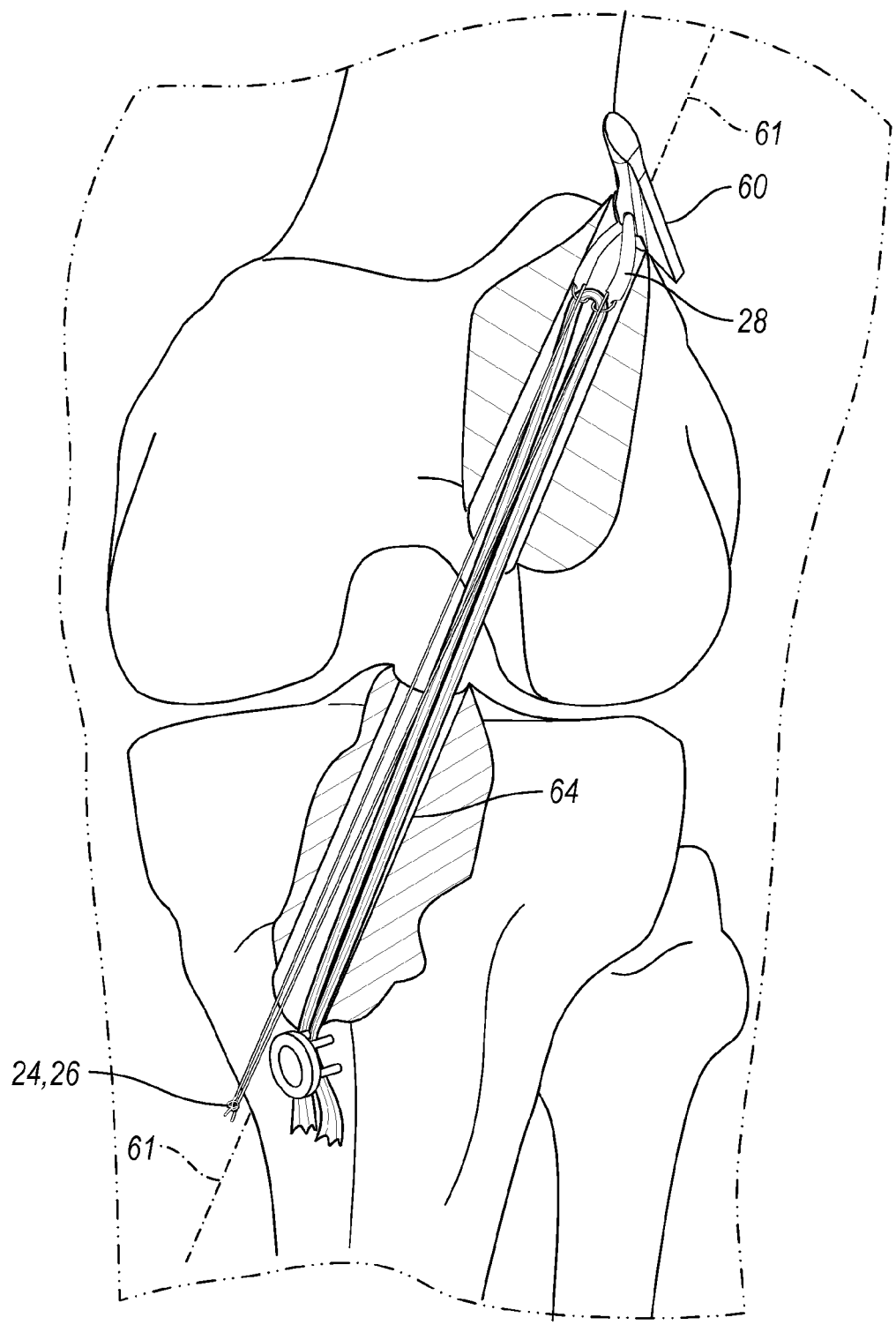

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
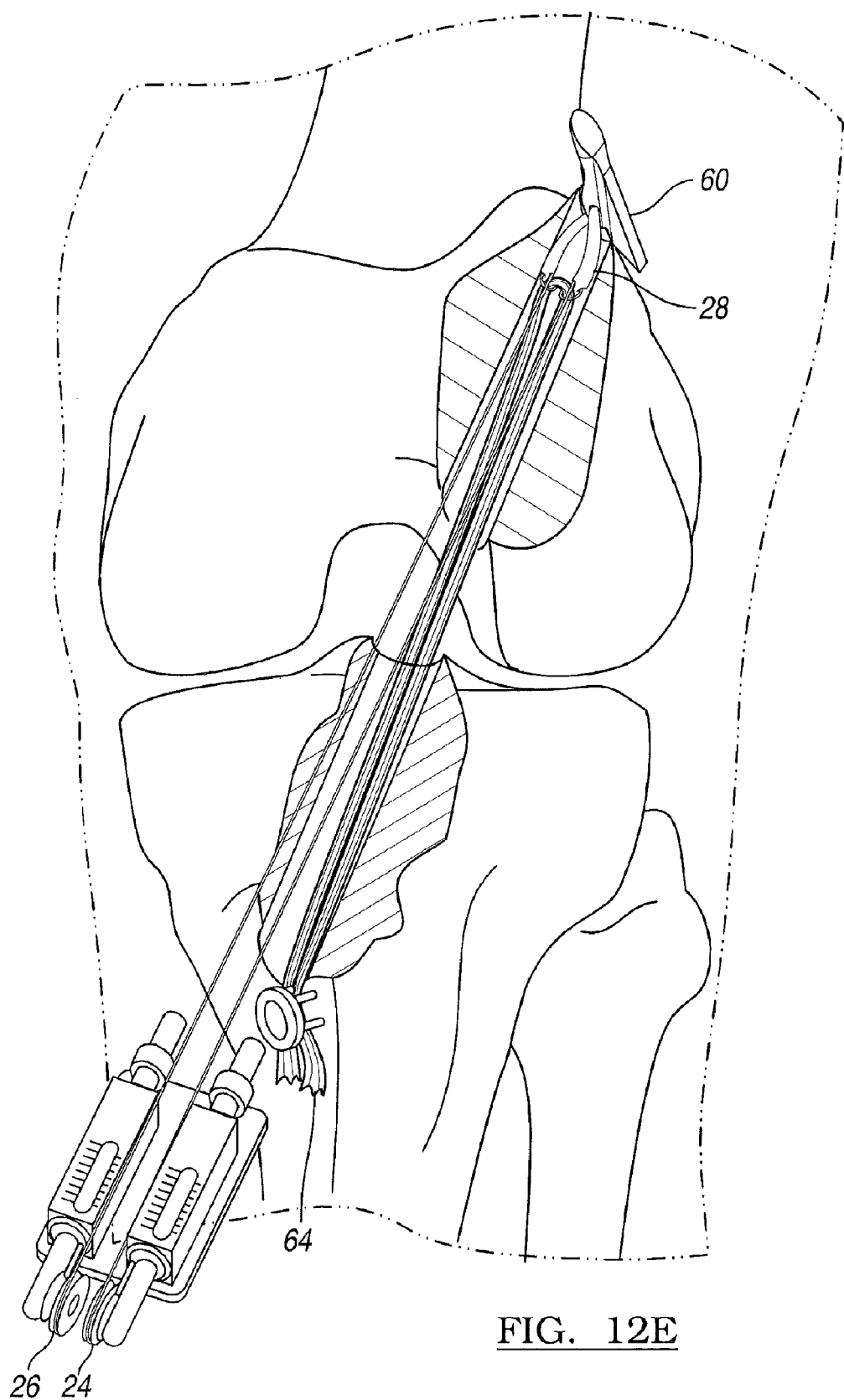
Figure 13A:
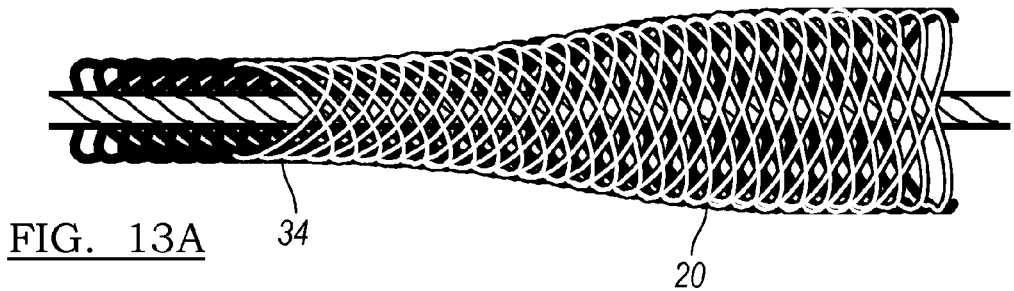
FIGS. 13A-13D represent a close-up view of the suture shown in FIGS. 1-11C.
Figure 13B:
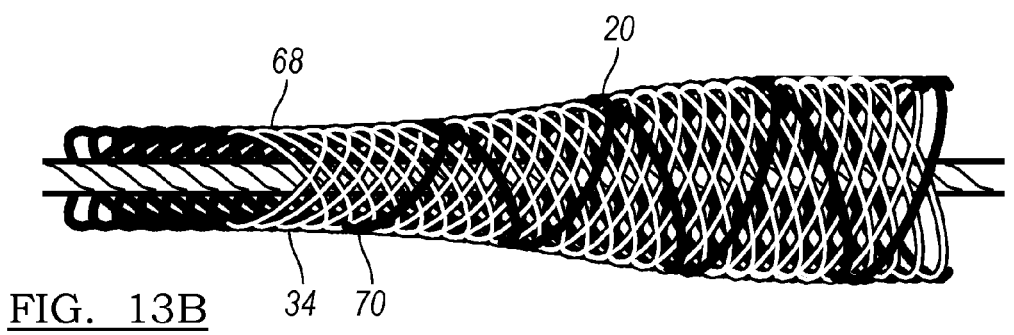
Figure 13C:
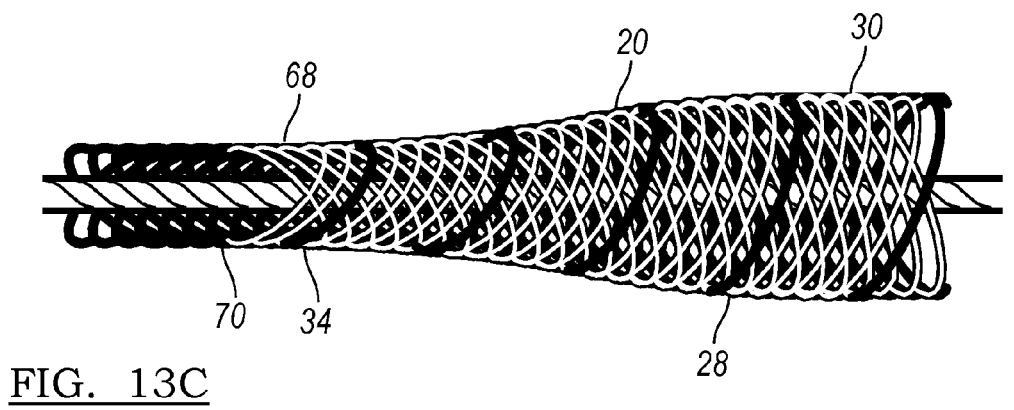
Figure 13D:
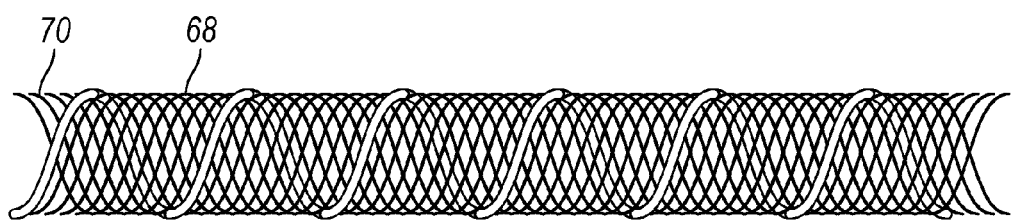

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14A:
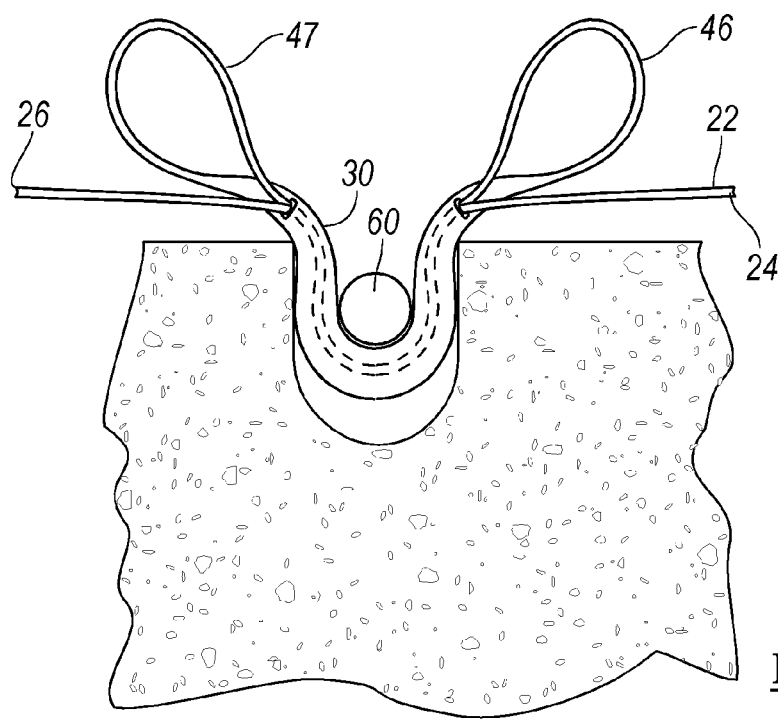
FIGS. 14A and 14B represent the coupling of the suture construction of FIG. 2A and FIG. 4 to bone.
Figure 14B:
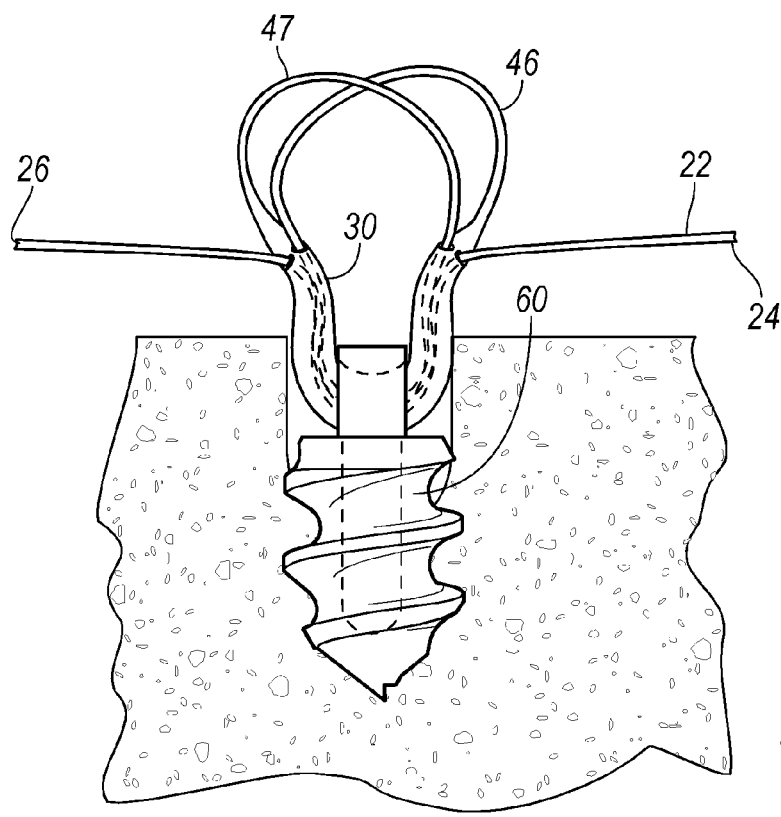

FIGS. 14A and 14B represent the coupling of suture construction 22 of FIG. 2A and FIG. 4 to a bone. The longitudinal passage 30 is coupled to a fixation member 60 which can be disposed within an aperture formed in the bone. The fixation member 60 can be, for example, a staple or a bone engaging screw. After coupling the suture construction 22 to the bone, loops 46 and 47 and ends 24 and 26 are readily accessible by the physician. The application of tension to the ends 24 and/or 26 causes the loops 46 and 47 to constrict. The loops 46 and 47 can be used to couple two or more portions of the anatomy. In this regard, the loops can be used to couple bone to bone or soft tissue to bone.

Figure 15A:
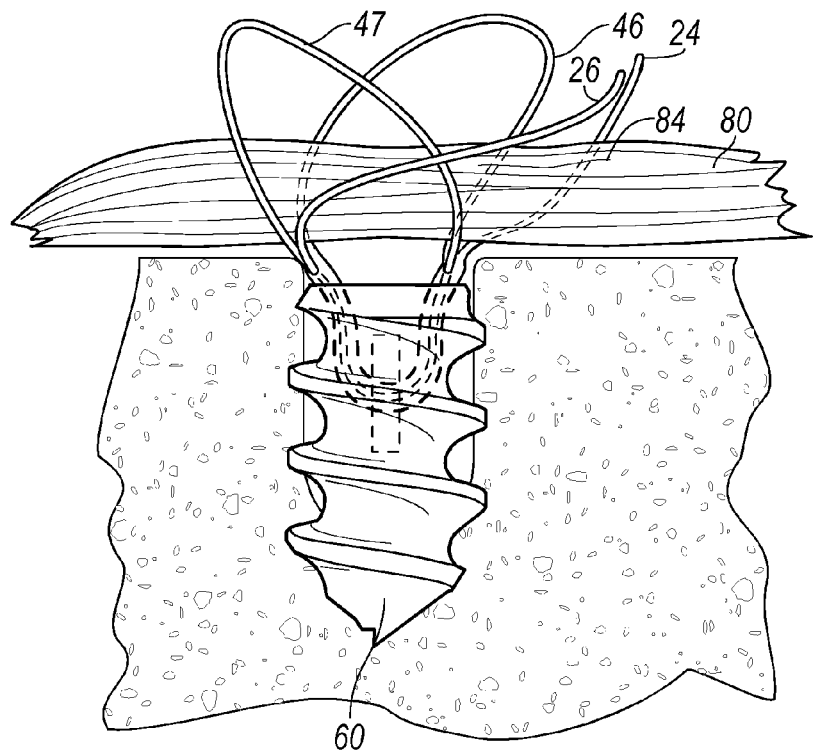
FIGS. 15A-15G represent the coupling of soft tissue to a bone according to the present teachings.
Figure 15B:
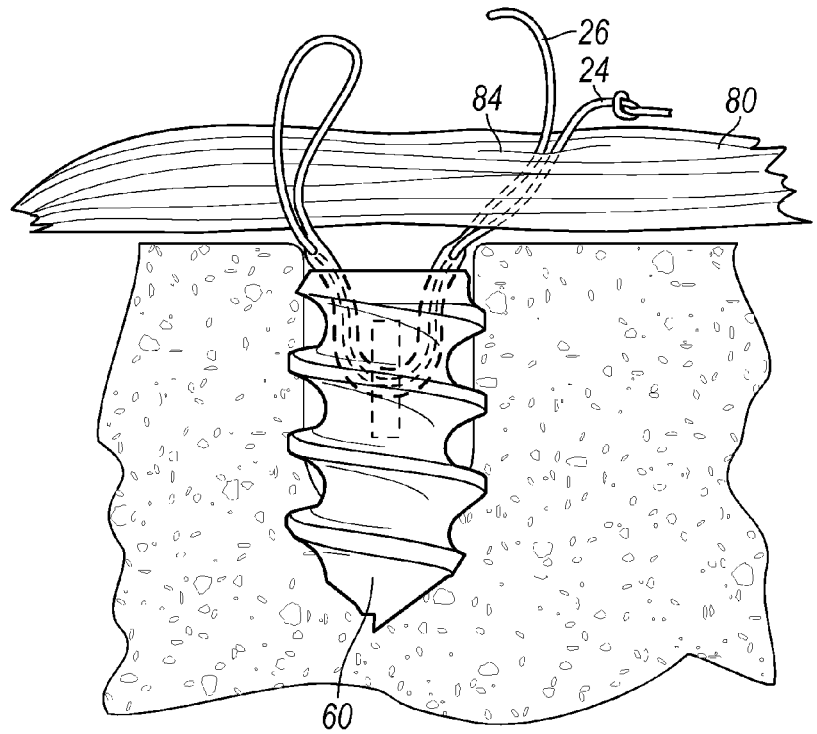

FIGS. 15A-15G represent the coupling of soft tissue 80 to bone. As shown in FIGS. 15A and 15B, the suture construction 22 is disposed about a portion of the soft tissue 80. Alternatively, an aperture or hole 84 can be formed in the soft tissue 80. A portion of the suture construction 22, for example, a loop 46 or loops 46, 47 or ends 24 and 26 can be threaded or pulled through the aperture 84. As seen in FIG. 15B, a single loop 46 of suture can be coupled to the fastener 60. This single loop 46 can be disposed over or around the soft tissue 80.

Figure 15C:
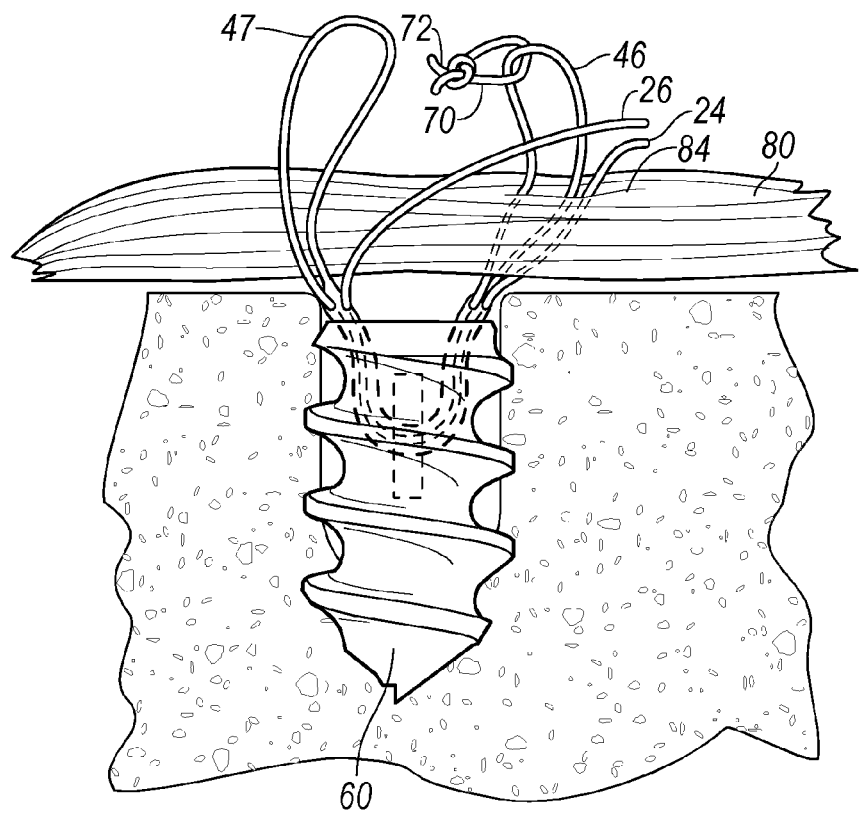

As shown in FIG. 15C, one loop 46 can have a fastening element 70 coupled thereto. This fastener element 70 can take the form of a loop of suture having a knot 72. This fastening element 70 along with the loop 46 and one or more strands 24 can be passed through the aperture 84 formed in the soft tissue 80.

Figure 15D:
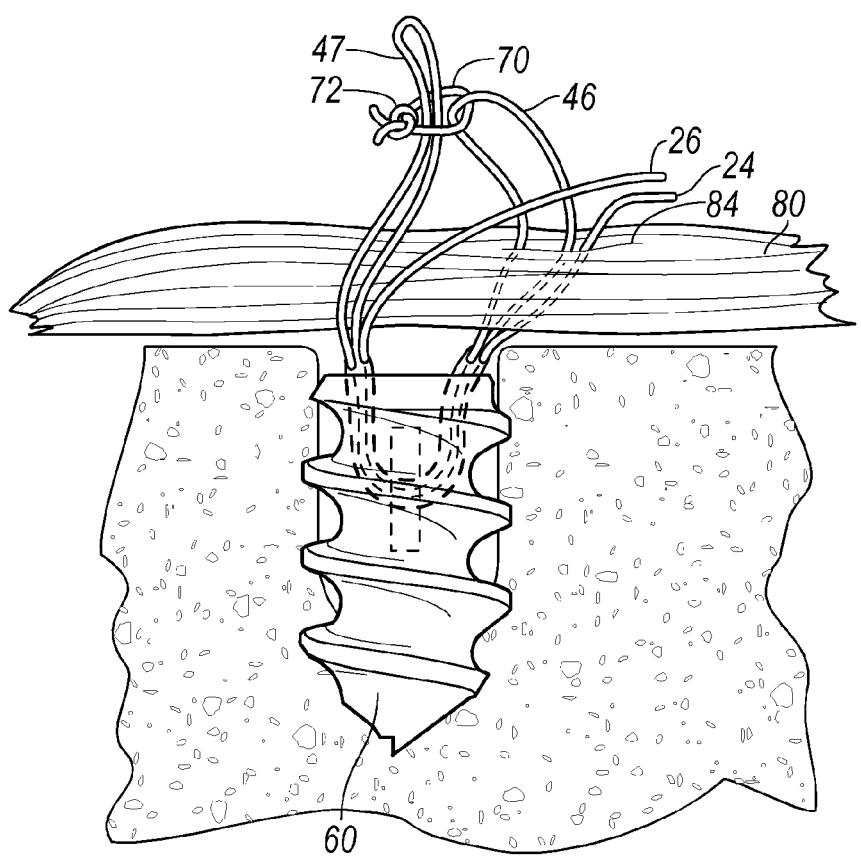

FIG. 15D shows the second loop 47 can be passed around the soft tissue and coupled to the fastening element 70. The first and second loops 46 and 47 are coupled together about the soft tissue 80, and optionally can be positioned about the knot 72.

Figure 15E:
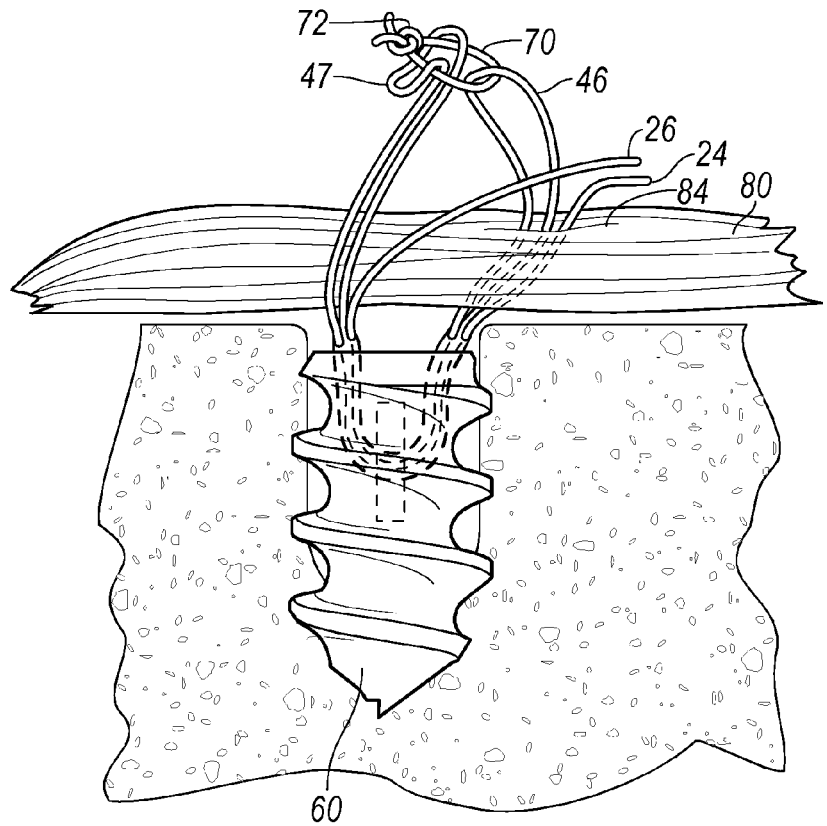
Figure 15F:
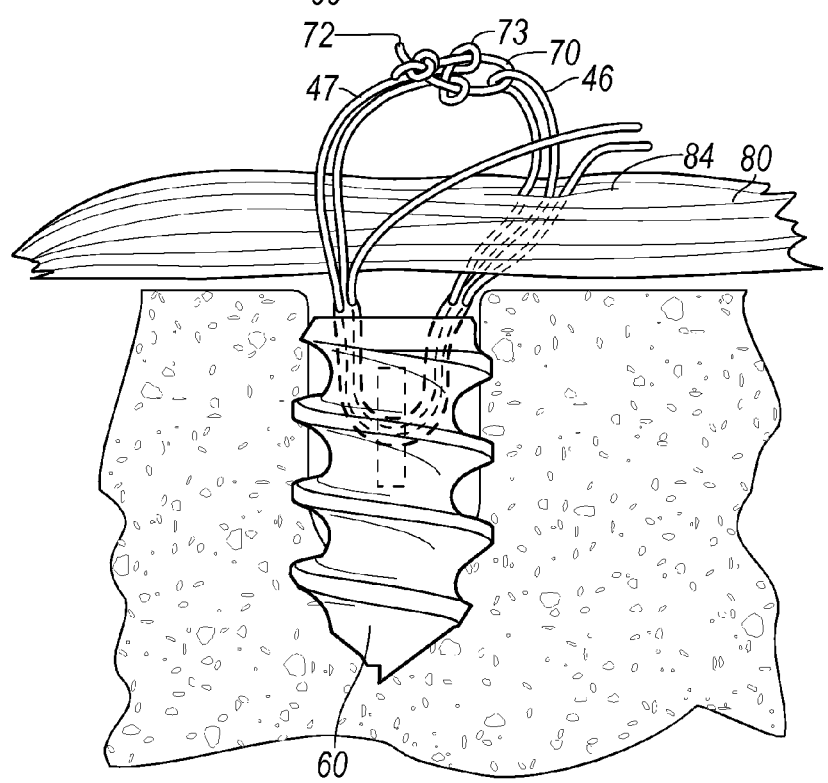
Figure 15G:
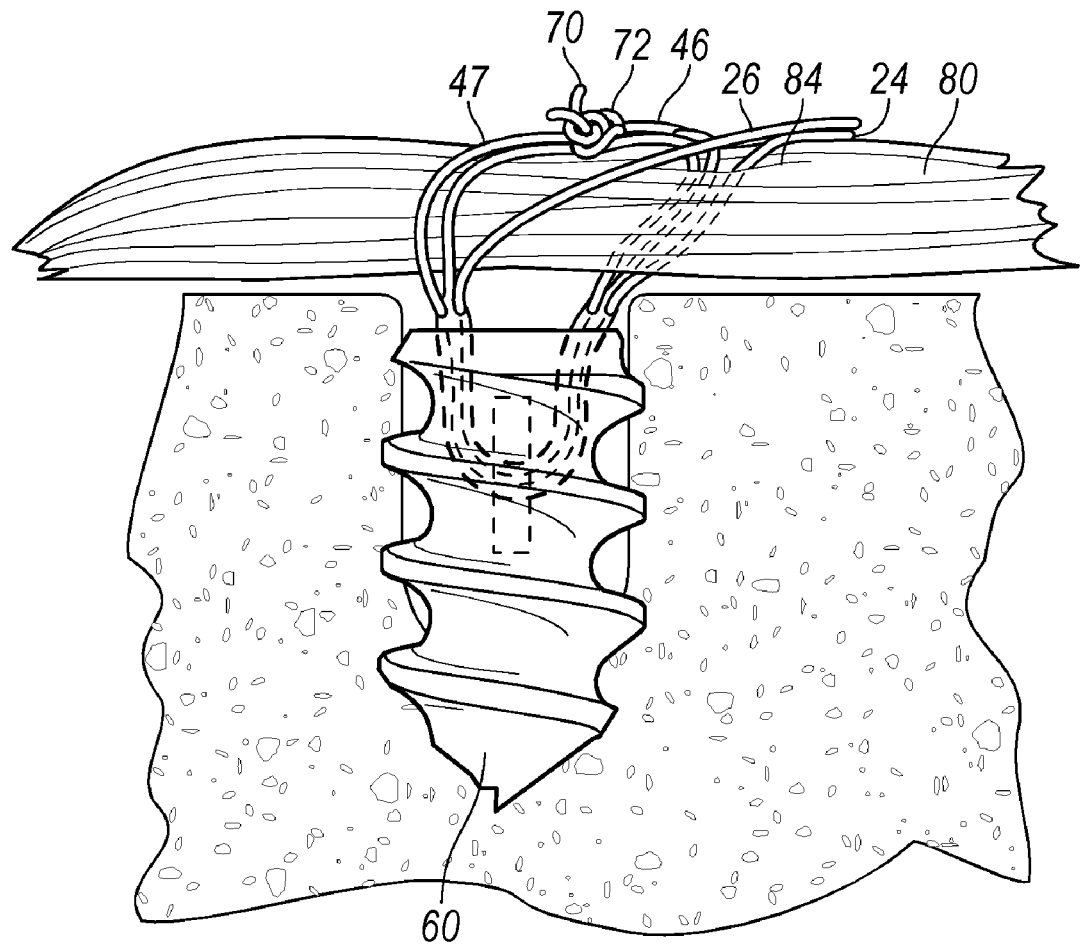

As shown in FIG. 15E, the first loop 46 and first end 24 can be passed through an aperture 84 of the soft tissue 80. Coupled to the first loop 46 is a fastener 70 in the form of a suture having a knot 72. The second loop 47 can be passed through the suture 70 and the knot 72 so as to form a pair of locking loops 73 (see FIG. 15F). FIG. 15G shows that tension can be applied to the first and second ends 24 and 26 of the suture 22 to constrict the suture 22 about the soft tissue 80. In this regard, the first and second loops 46 and 47 are tightened to constrict about and fix the soft tissue 80 to the bone.

Figure 16A:
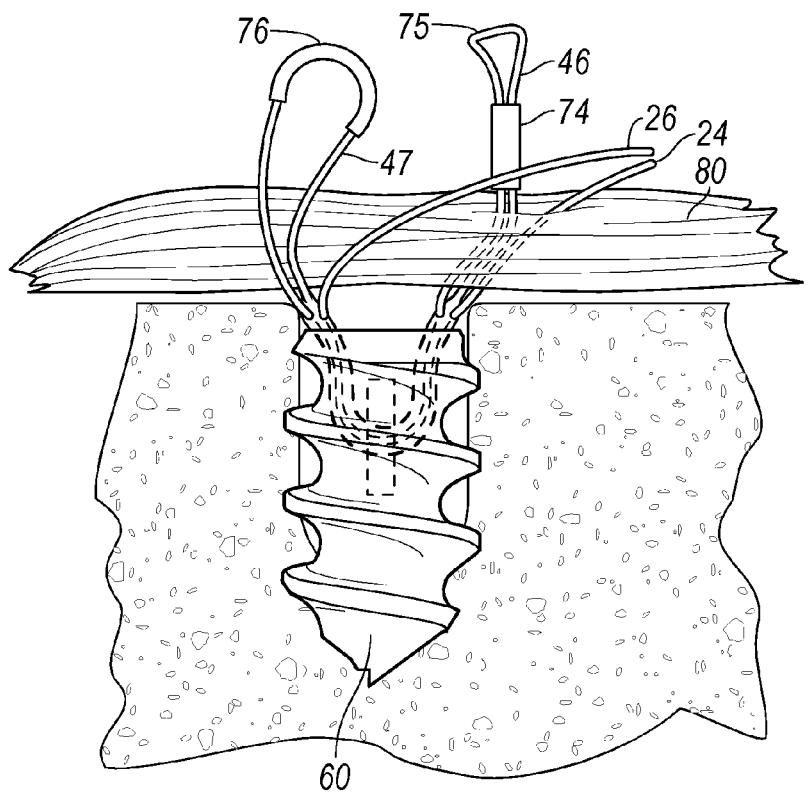
FIGS. 16A-16D represent the coupling of soft tissue to a bone using alternate teachings.

As seen in FIG. 16A, the construction of FIGS. 14A and 14B can be modified so as to place a pair of collapsible fabric tubes 74 and 76 about a portion of the suture 22. In this regard, collapsible tubes 74 and 76 can be coupled to the first and second suture loops 46 and 47. It is also envisioned several collapsible tubes can be coupled to a single loop 46 or the suture ends 26, 27.

Figure 16B:
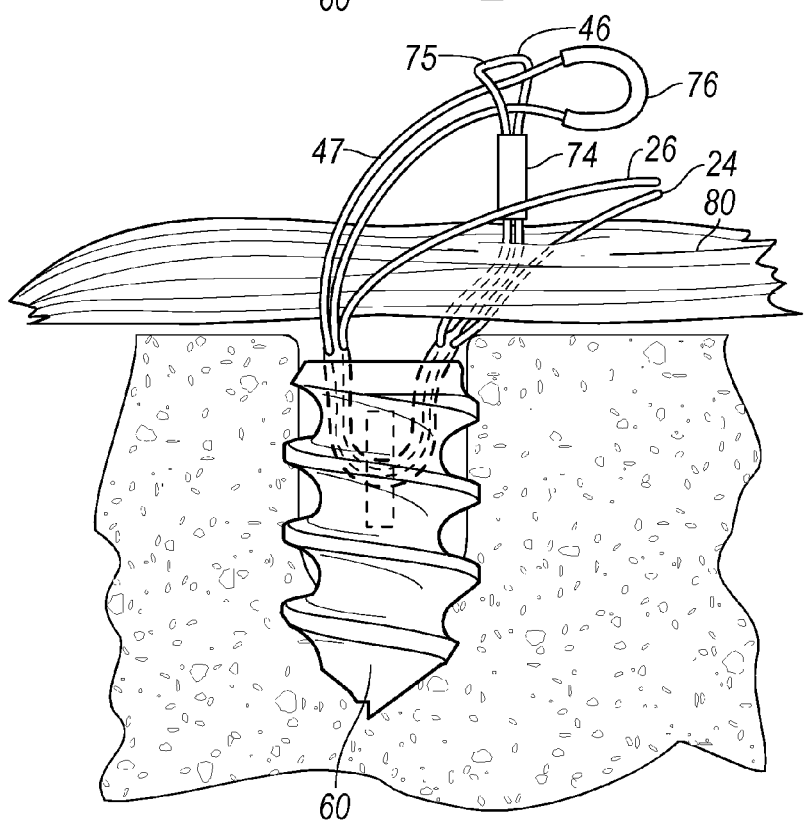
Figure 16C:
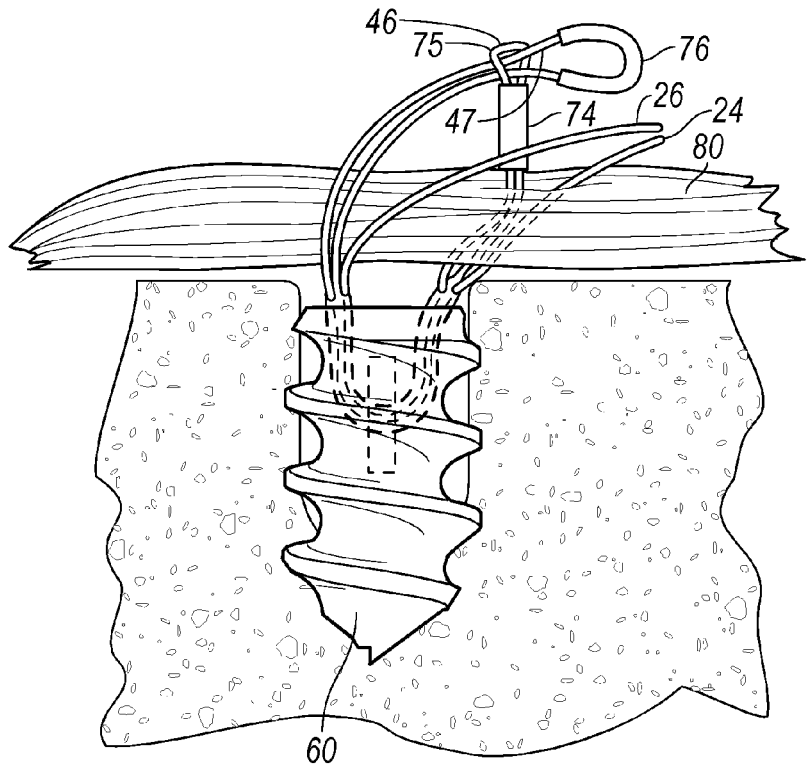
Figure 16D:
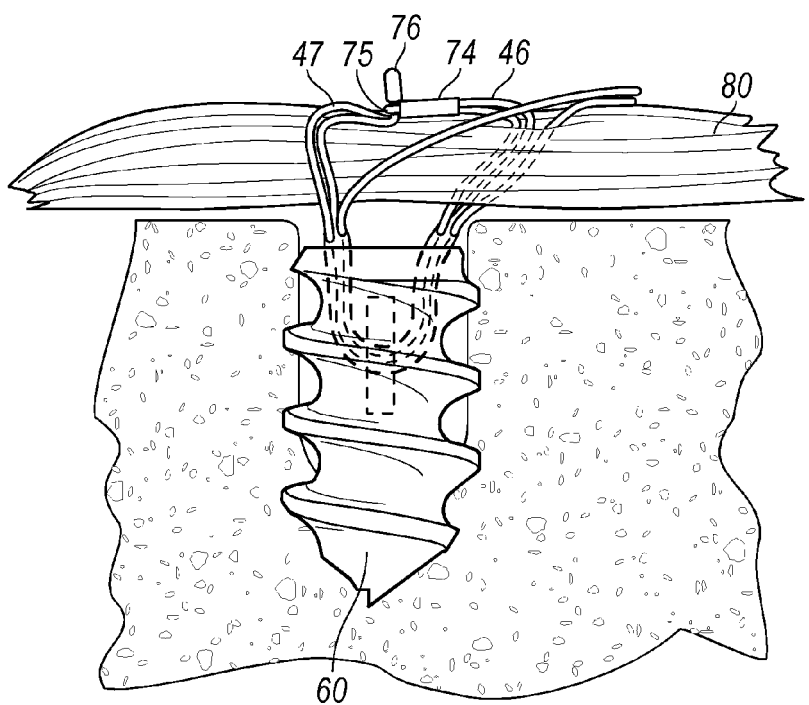

The collapsible tubes 74 and 76 can be either threaded onto (76) or disposed about a loop 75 formed in the suture loop 46. As seen in FIG. 16B, the first collapsible tube 76 can be fed through the loop 75. When tension is applied to the second end 26 of the sutures 47, the first loop 46 constricts about the second loop causing the collapse of the first collapsible tube 74. As shown in FIG. 16D, tension can be applied to the first suture end 24 causing the second loop 47 to constrict causing the collapse of the second collapsible tube 76 and the subsequent locking of the soft tissue 80 to the bone.

Figure 17A:
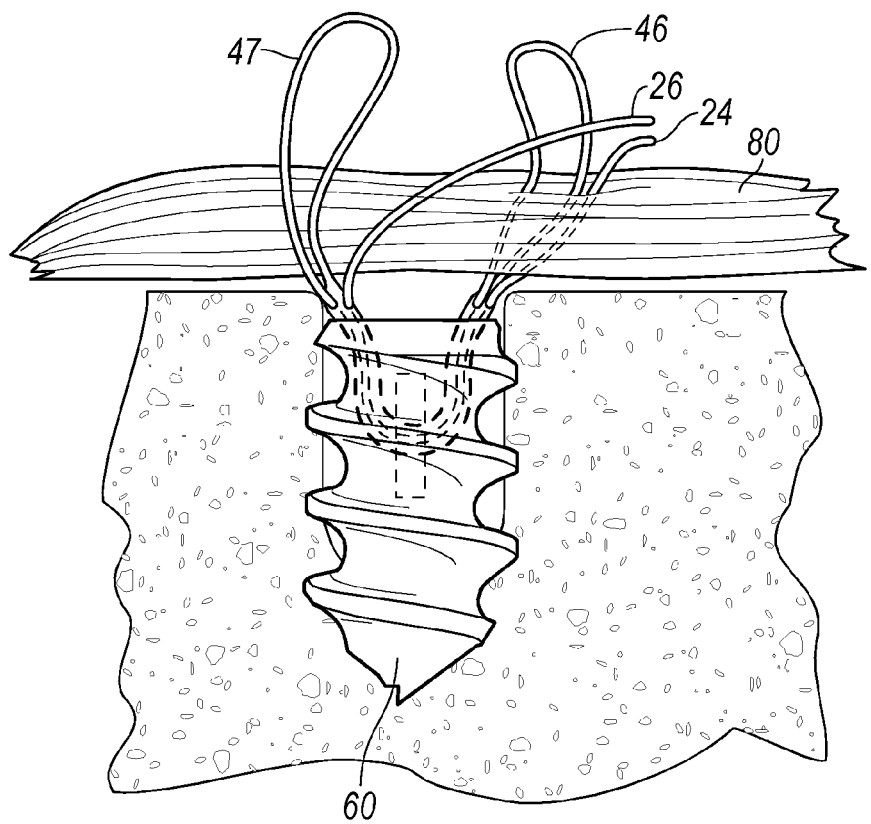
FIGS. 17A-17E represent the coupling of soft tissue to a bone using alternate teachings.
Figure 17B:
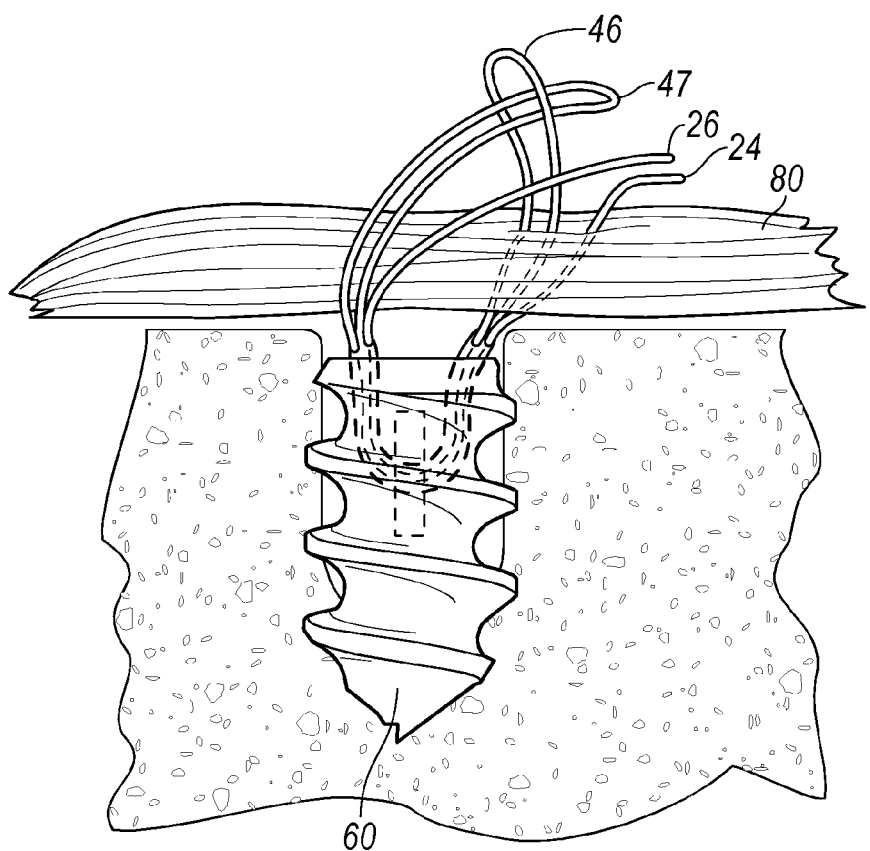
Figure 17C:
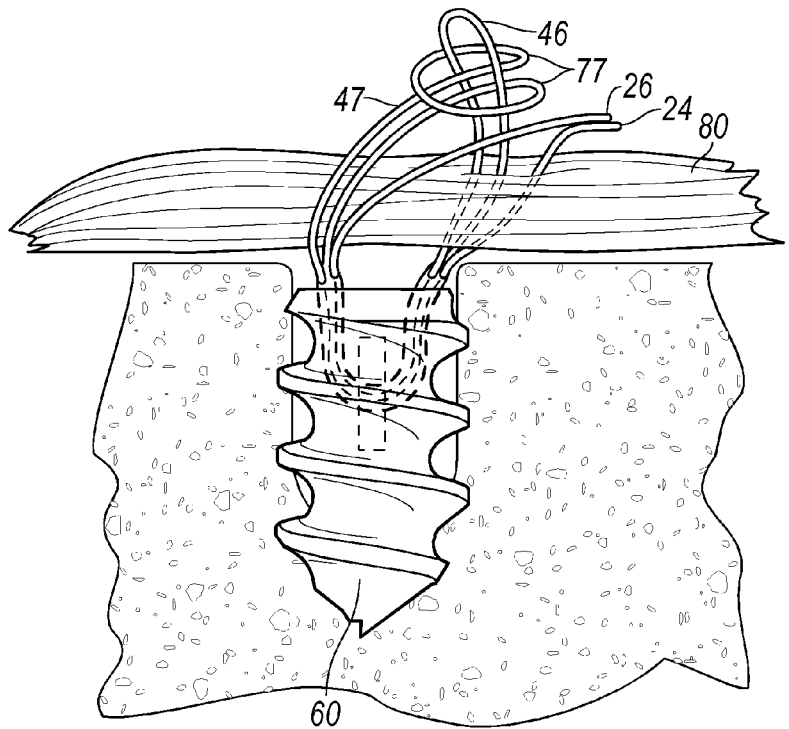

FIGS. 17A-17E represent an alternate method for coupling soft tissue 80 to a bone using the construction of FIGS. 14A and 14B. As shown in FIG. 17A, the first loop 46 and first suture end 24 are passed through an aperture 84 formed in the soft tissue 80. The second loop 47 is passed through the first loop 46.

Figure 17D:
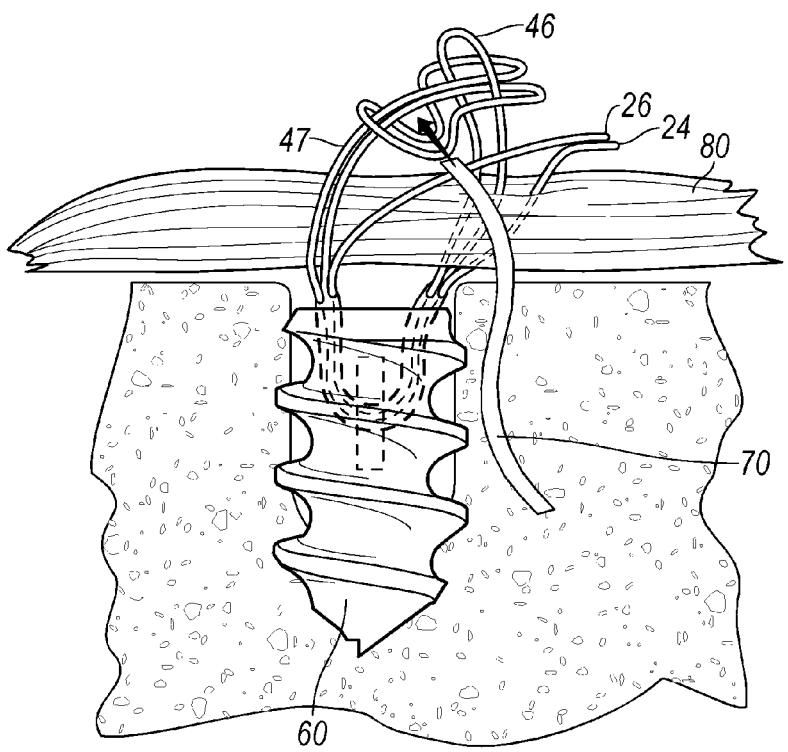
Figure 17E:
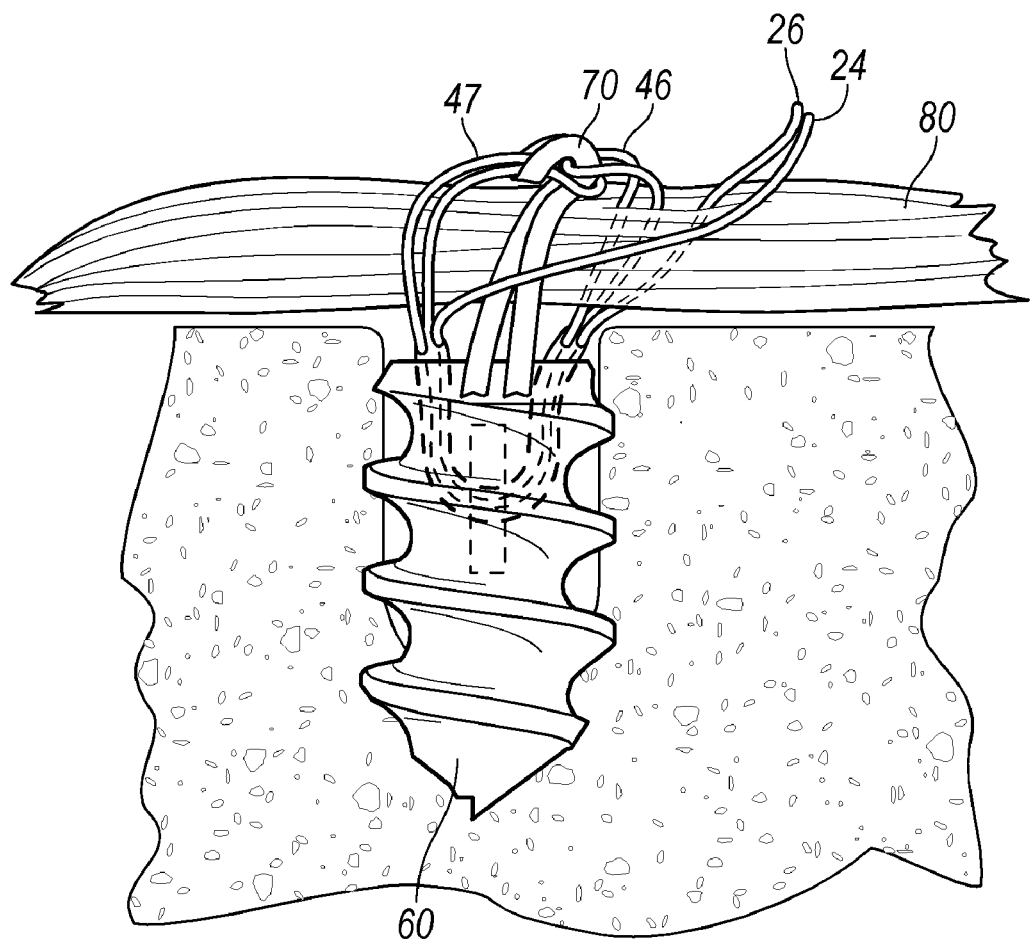

The second loop 47 is then doubled back over the first loop 46 causing a pair of intermediate loops 77. As shown in FIG. 17D, a locking member 70, soft or hard, can then be passed through the pair of intermediate loops 77 or a portion of the first loop 75 to lock the first and second loops 46 and 47 together. As shown in FIG. 17E, tension applied to the suture ends 26, 27 tighten the loops 46 and 47 about the locking member 70. The soft tissue 80 is also fixed to the bone.

Figure 18A:
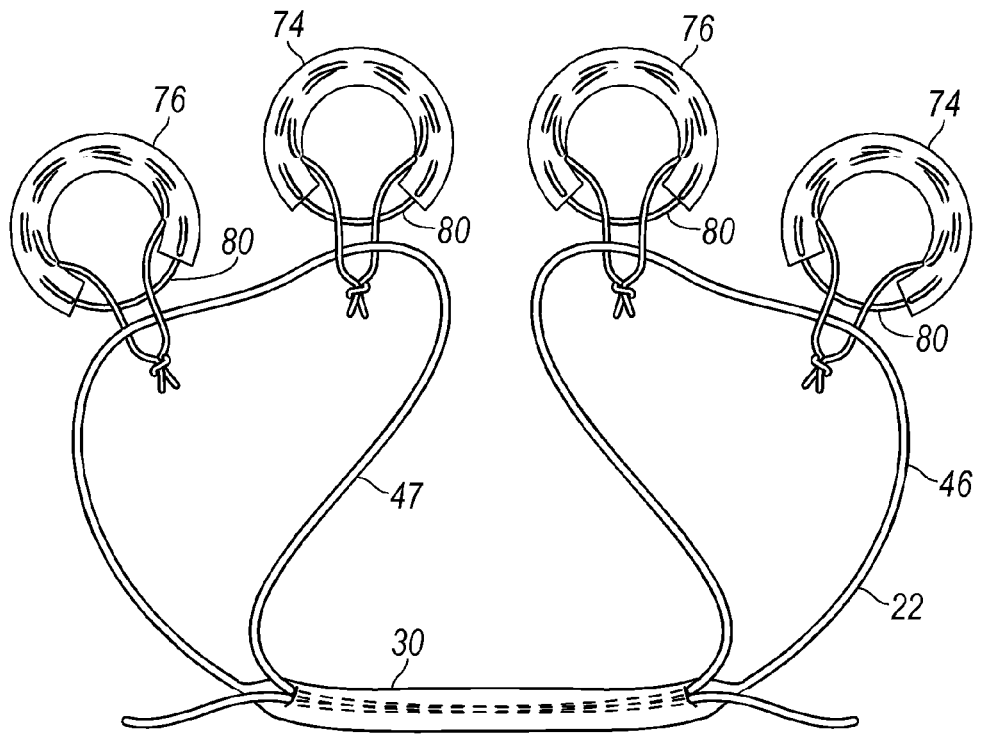
FIGS. 18A-18C represent the coupling of soft tissue to a bone using multiple collapsible loop structures.
Figure 18B:
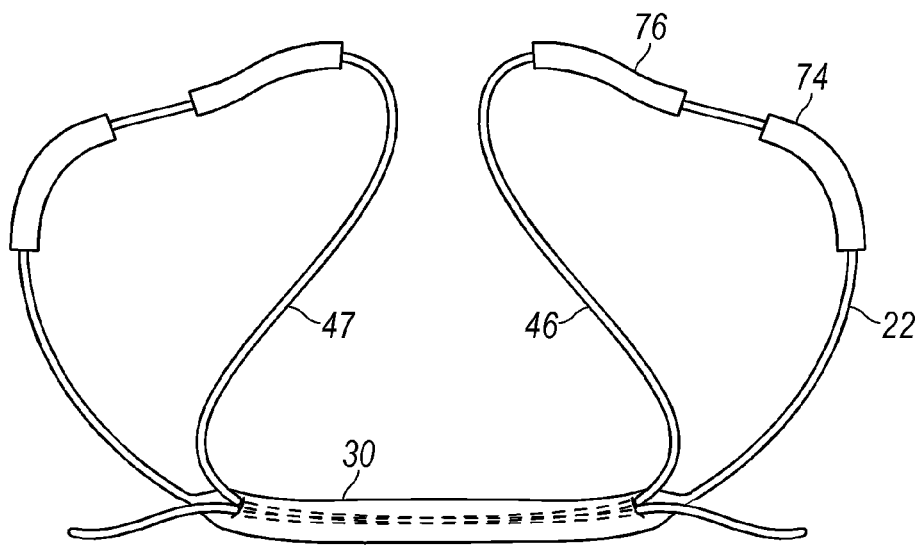
Figure 18C:
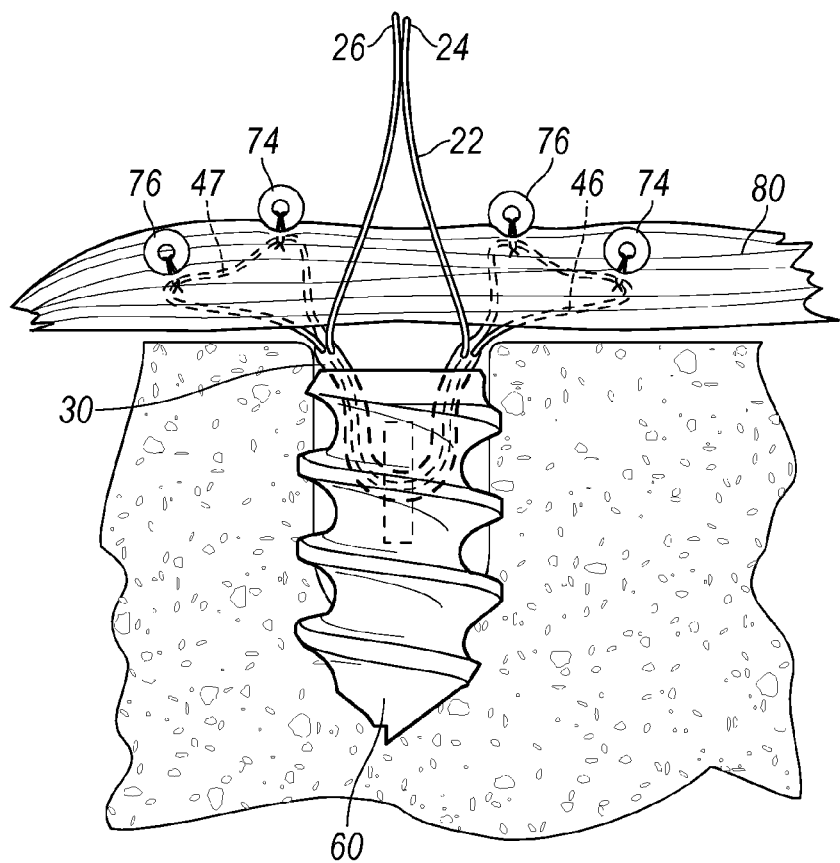

FIGS. 18A-18C represent alternate suture constructions 22 which are used to couple soft tissue 80 and 81 to bone. Disposed about the first and second loops 46 and 47 are collapsible tubes 74 and 76. The tubes 74 and 76 which can be, for example, fabric or polymer, can either be directly disposed about the suture 22 of the first and second loops 46 and 47, or can be coupled to the suture loops 46 and 47 using a separate loop member 81.

As shown in FIG. 18C, the suture construction 22 shown in FIG. 18A or 18B, the collapsible tubes 74 and 76 are passed through the apertures 84 formed in the soft tissue 80. The application of tension to the ends 26 and 27 causes the soft tissue 80 to be drawn against the bone and cause compressive forces to be applied to the collapsible tubes 74 and 76. By tightening the suture which passes through the passage 30, the soft tissue 80 is coupled to the bone without the use of knots.

Figure 19A:
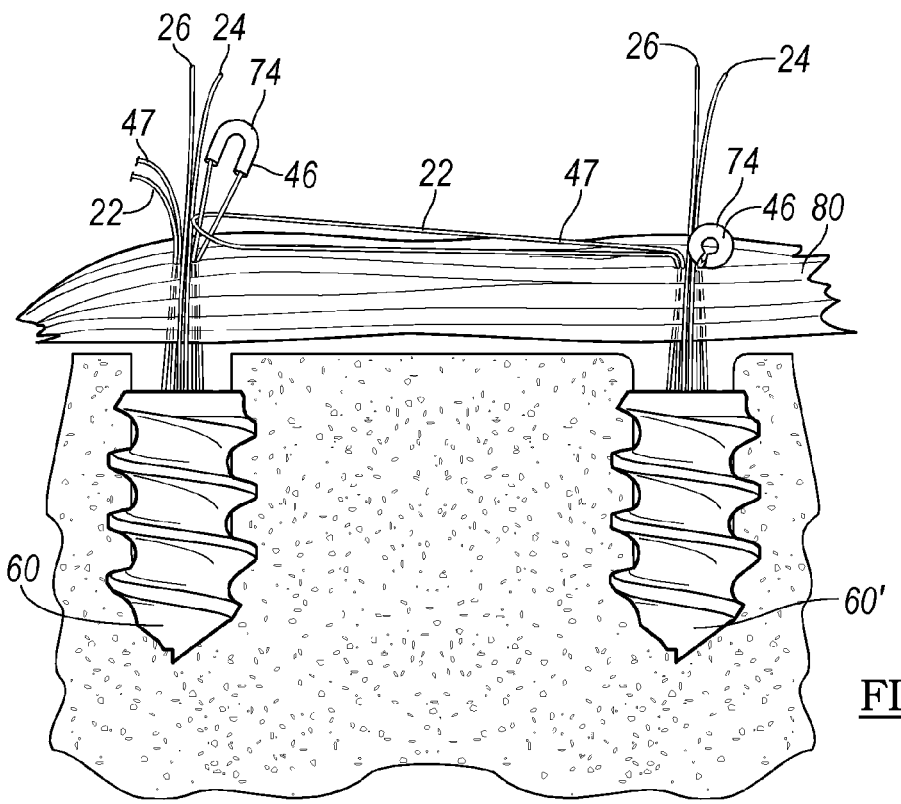
FIGS. 19A-19C represent the coupling of soft tissue to a bone using yet alternate teachings.
Figure 19B:
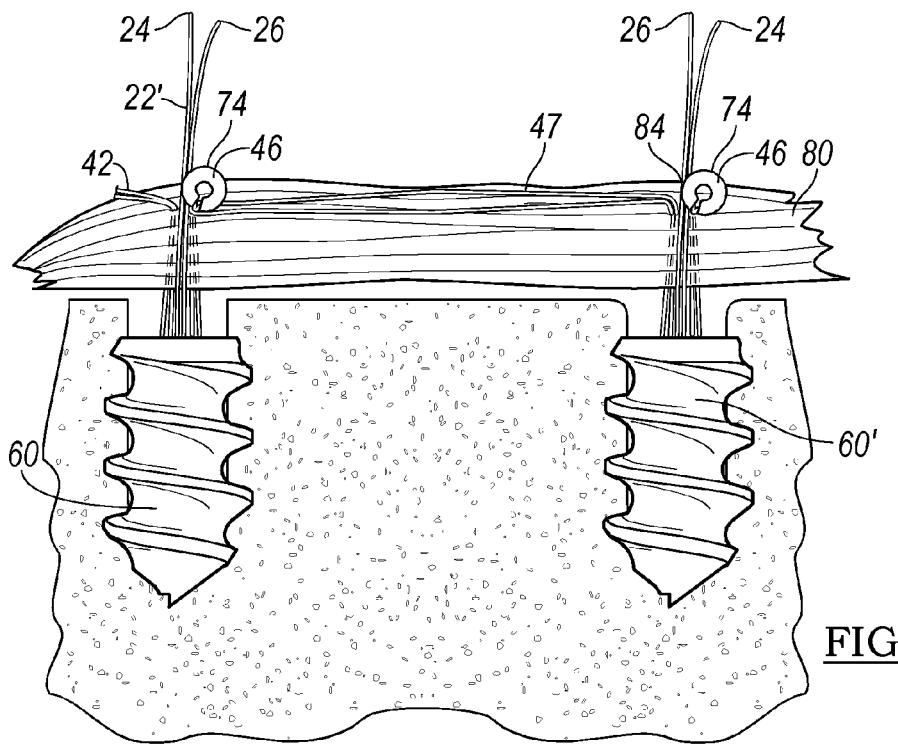
Figure 19C:
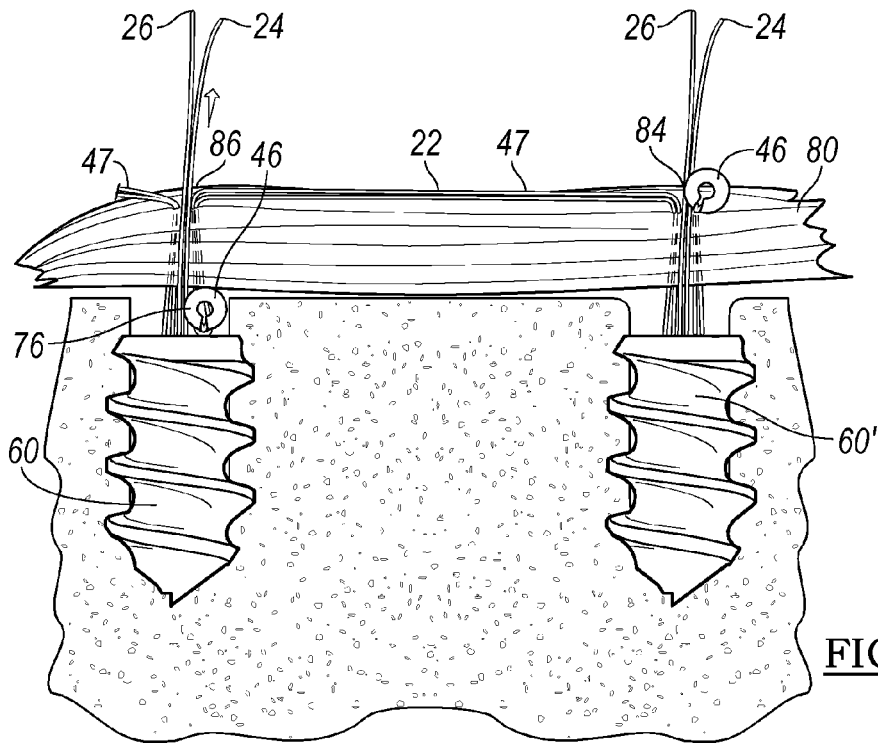

As can be seen in FIGS. 19A-19C, several fixation members 60 and 60' can be coupled to the suture construction 22 to fasten soft tissue 80 to bone. As seen in FIG. 19A, the collapsible tube 74 can be coupled to a first loop 46 while the second loop 47 can be used to couple the first suture 22 to the second fastener 60'. In this regard, they are coupled using a collapsible tube 76 of the second suture 22', thus allowing downward force along the entire length between the fasteners, thus providing bridge fixation as well as point fixation.

As seen in FIG. 19B, tension of the ends 24 and 26 of the first suture 22 draws the second loop 47 into the fixation member 60'. The second loop 47 of the first suture 22 is then coupled to the collapsed tube 76. This couples the first and second fasteners together and applies the downward force.

As seen in FIG. 19C, the second loop 47 of the first suture 22 can be passed through a second aperture 86 in the soft tissue 80. A second loop 47 is then coupled to the collapsible tube 76 associated with the second suture 22'. The collapsed tube 76 of the second suture 22' functions to fix the suture 22' to the fixation member 60'. It is envisioned the collapsed tube 76 can be found within a bore defined in the bone or the fastener 60.

Figure 20A:
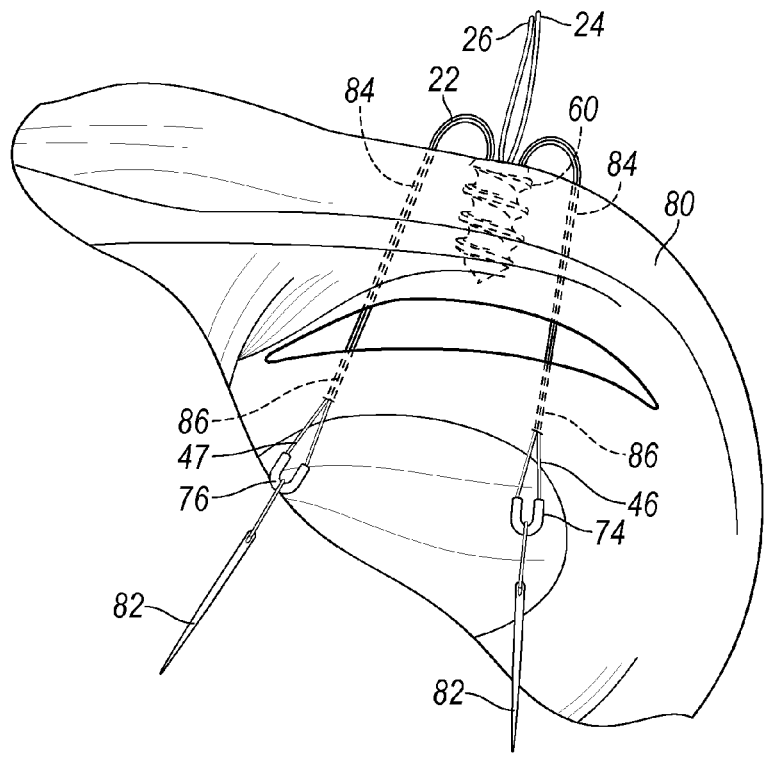
FIGS. 20A and 20B represent a meniscal repair according to the present teachings.
Figure 20B:
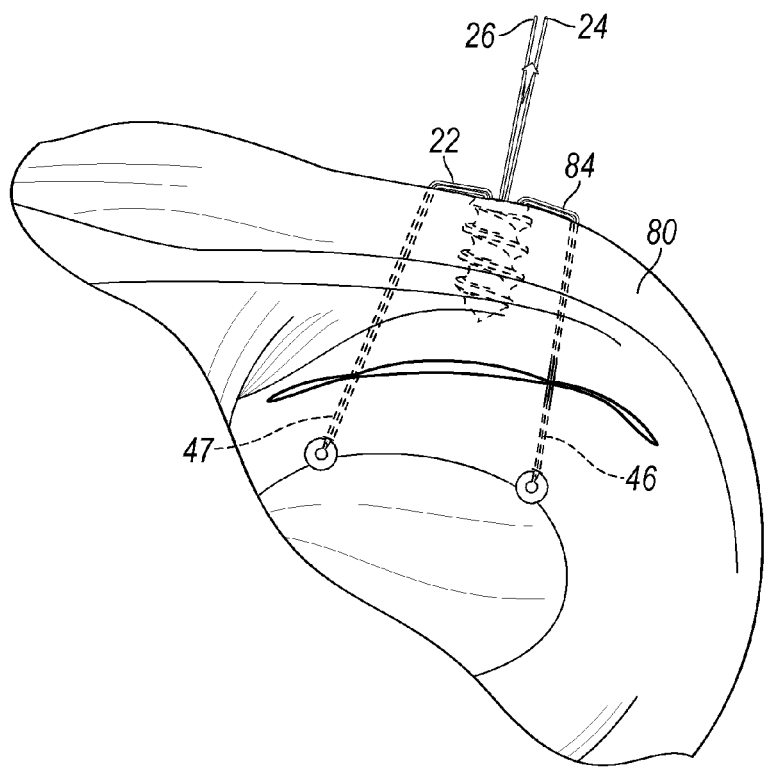

FIGS. 20A and 20B represent the use of a suture construction 22 to repair a meniscus. Fasteners 82 are coupled to first and second loops 46 and 47. After the fixation member 60 is coupled to bone or soft tissue, the first loop 46 is passed through a first aperture 84 in a first portion of the meniscus. The first loop and collapsible tube 74 is then passed through a second aperture 86 and a second portion of the meniscus. The second loop 47 and second collapsible tube 76 are similarly passed through the meniscus. Tension is applied to the first and second ends 24 and 26 of the suture 22 to pull the meniscus together. As seen in FIG. 20B, a first and second collapsible tube 74 and 76 are constricted so as to couple the suture to the meniscus.

Figure 21:
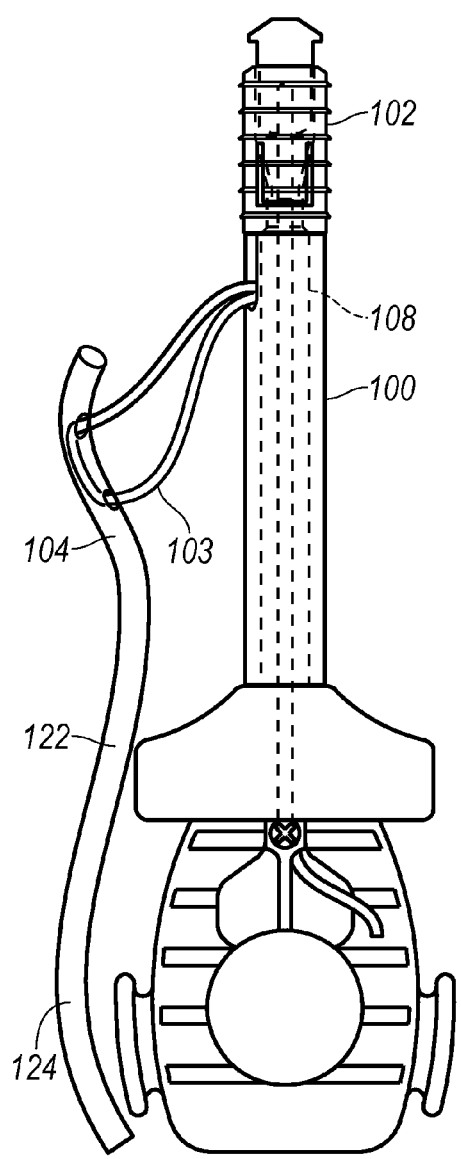
FIG. 21 represents an insertion tool with associated fastener and soft tissue anchor.

FIG. 21 represents a tool 100 with associated fastener 102 and soft tissue anchor 104. The tool 100 has a handle portion 106 which releasably engages the fastener 102. Associated with the handle portion 106 is a hollow longitudinal suture 103 which accepts a soft tissue anchor 104. Disposed at a distal end 110 of the hollow longitudinal portion 108 is a slot having a portion of the soft tissue anchor 104 disposed therethrough. The distal end 110 is further configured to support the fastener 102 for insertion into a bore defined within bone 112.

Figure 22:
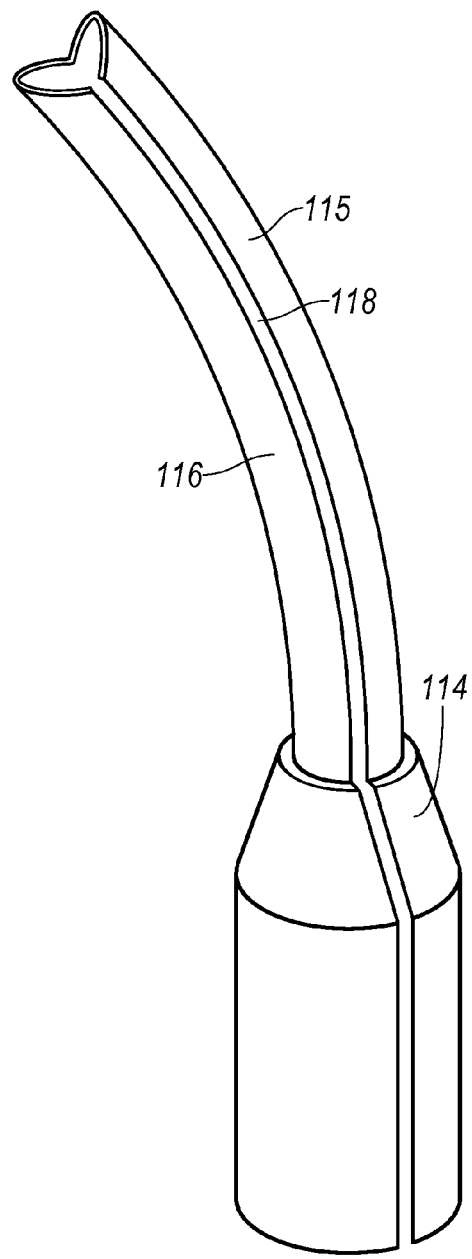
FIG. 22 represents an insertion sleeve associated with the tool shown in FIG. 21.

FIG. 22 represents an insertion guide 115 having a handle portion 114 and a curved longitudinal guide tube 116. The longitudinal guide tube 116 and handle portion 114 slidably accept the fastener 102 and soft tissue anchor 104. The curved longitudinal tube 116 and handle portion 112 define a slot 118 which also slidably accepts the suture 103 of soft tissue anchor 104.

Figure 23:
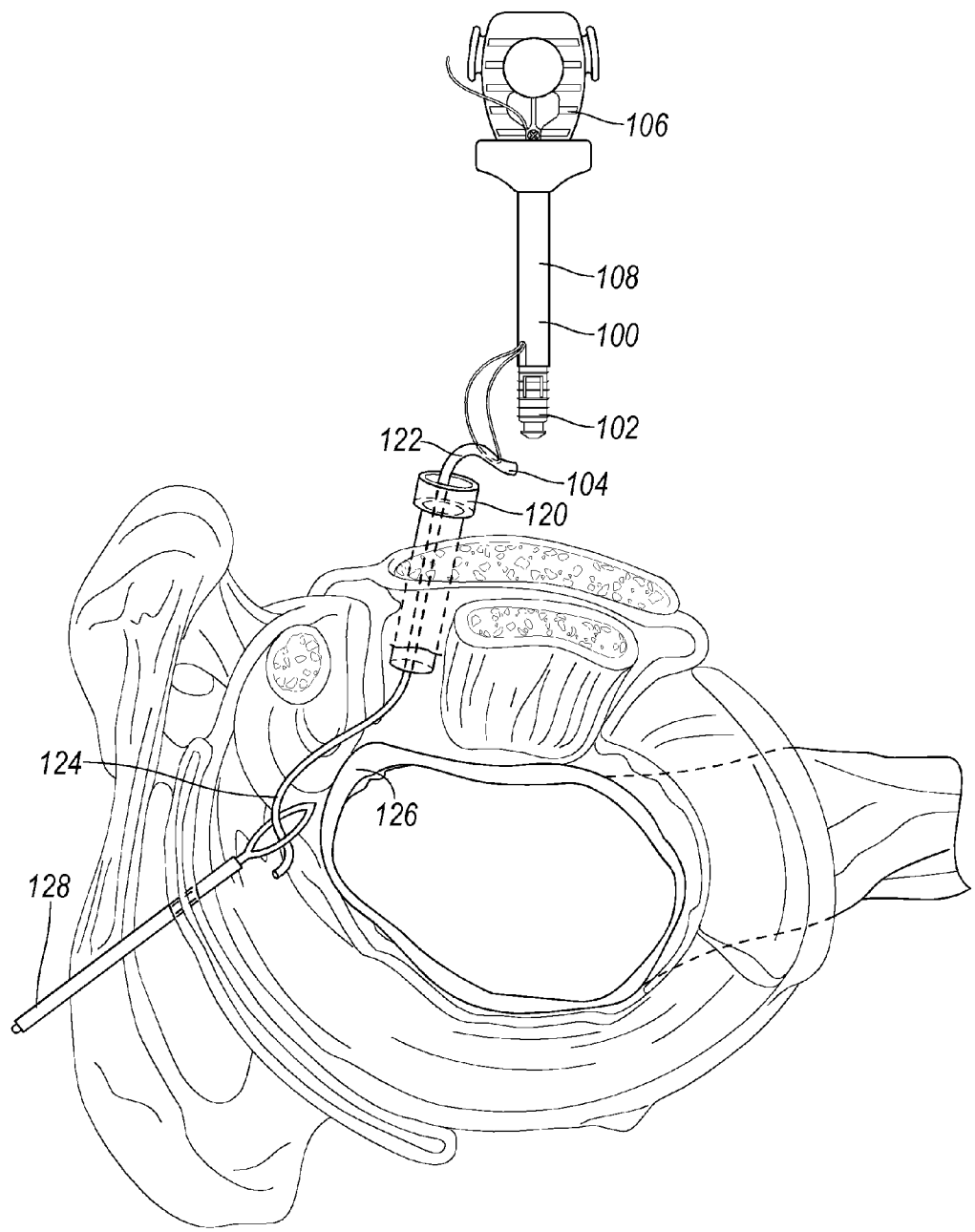
FIGS. 23-31 represent the repair of a rotator cuff using a tool shown in FIG. 21.

FIGS. 23-38 generally depict the repair of labral tissue of a glenoid. While the repair shown generally relates to a specific anatomical injury, it is envisioned the teachings herein can be applied to other anatomical regions which require the coupling of soft tissue to bone. For example, a meniscal repair in a knee may be performed using similar techniques. As shown in FIG. 23, access to the region of the injury is made through a tube 120. At this point, a collapsible tube 122 having an extended portion 124 is threaded through tube 120 into close proximity of the soft tissue 126 to be coupled to bone. A suture grabber 128 such as a speed pass by Biomet Sports Medicine is used to pierce the soft tissue 126 and to grab the extended portion 124 of the collapsible tube 122. This extended portion 124 is then pulled through the soft tissue 126.

Figure 24:
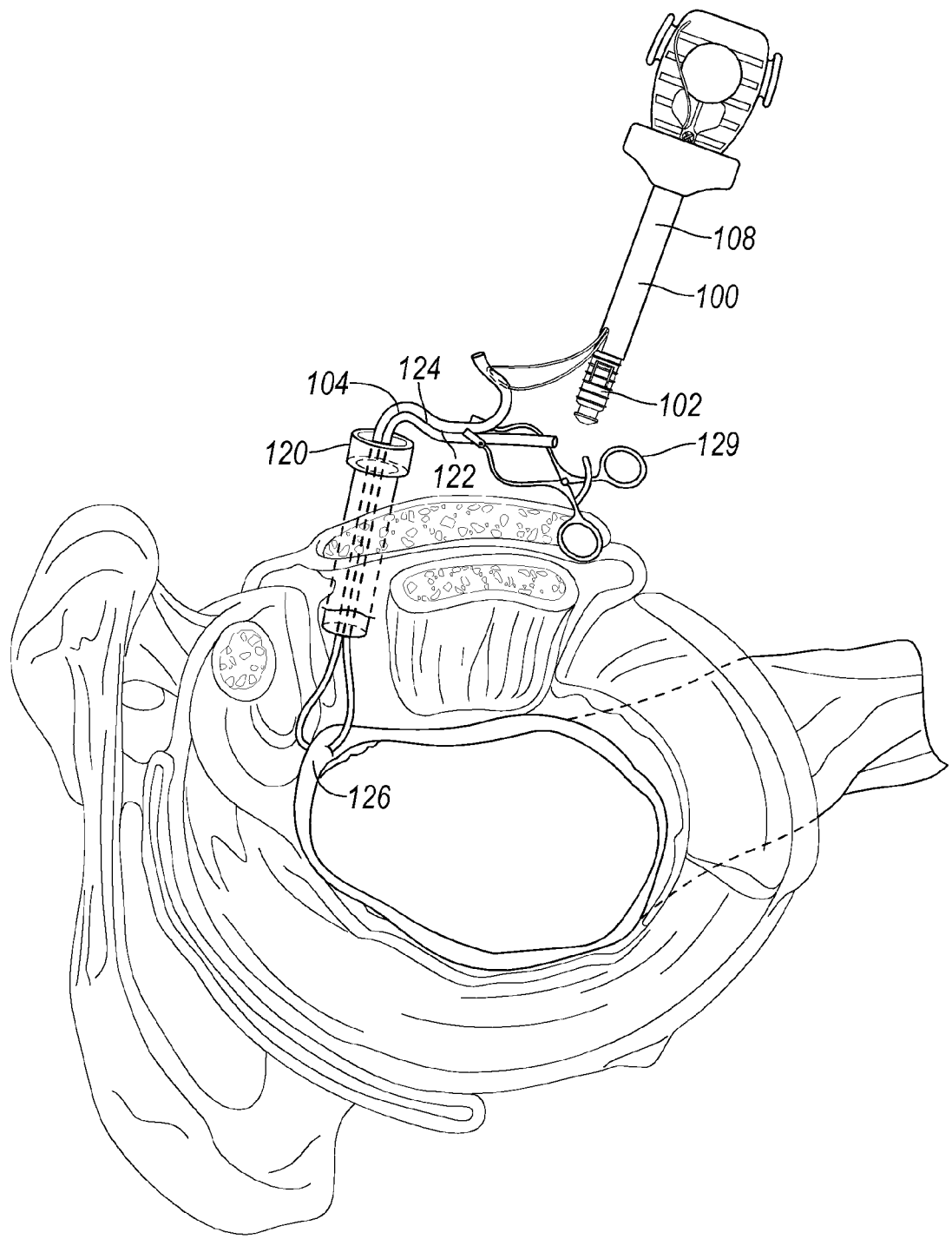
Figure 25:
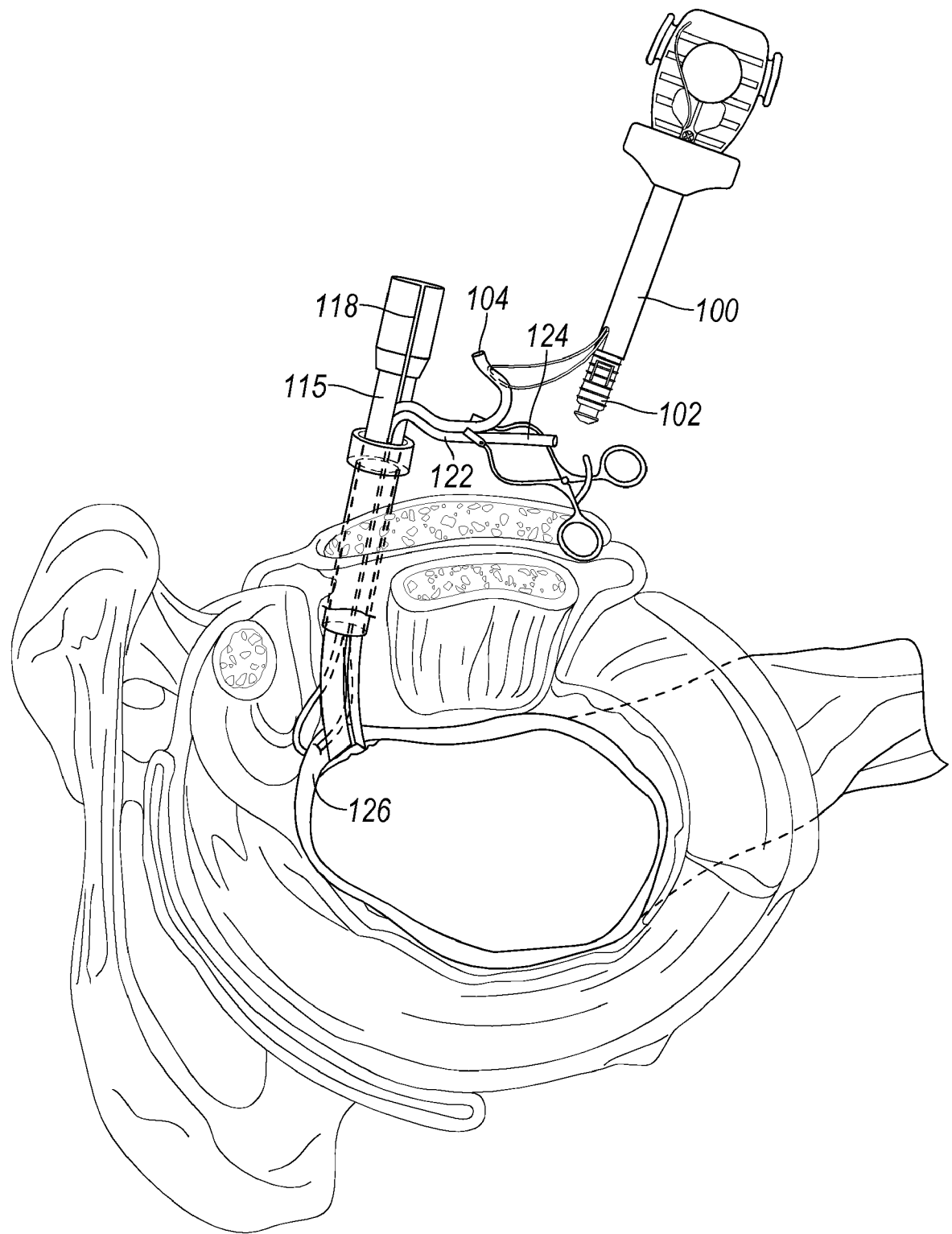

As shown in FIG. 24, the extended portion 124 of the collapsible tube 122 is fed back out the access tube 120 and clamped with clamp 129 so as to prevent inadvertent translation with respect to the tube. As shown in FIG. 25, the insertion sleeve 115 is placed through the access tube 120. The collapsible tube 122 is placed through the slot 118 defined in the handle portion 114 and longitudinal guide tube 116.

Figure 26:
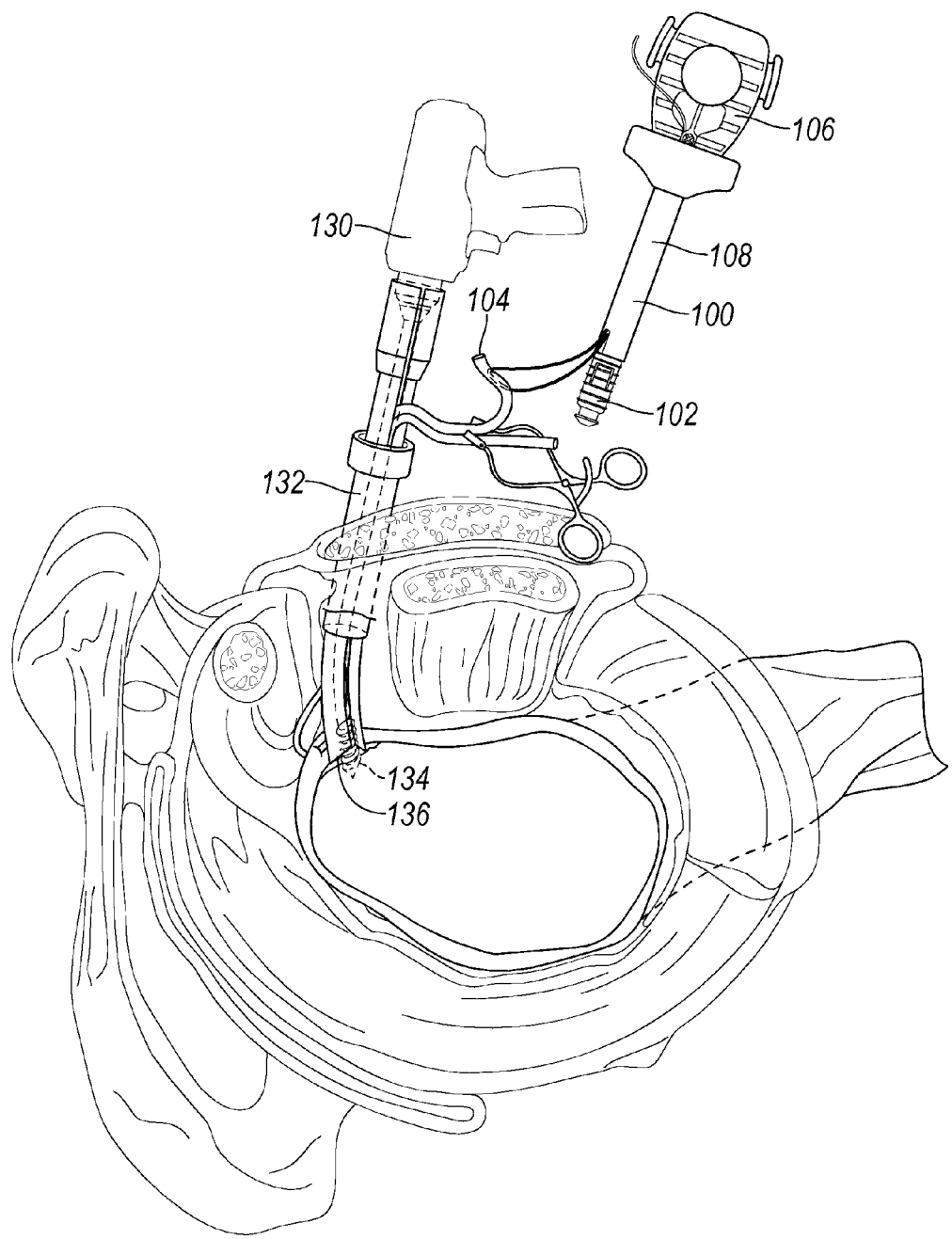
Figure 27:
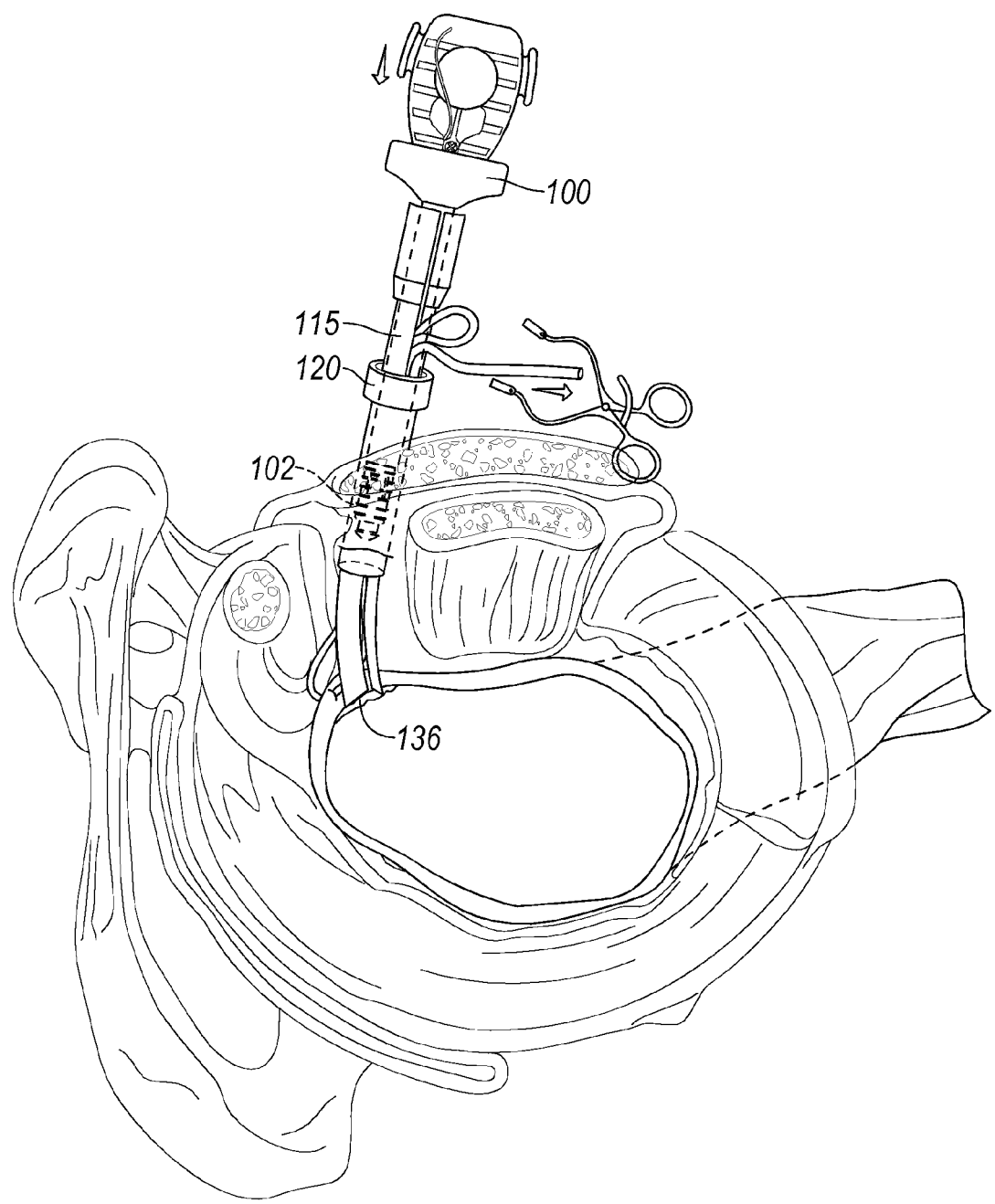

FIG. 26 shows a drill 130 having a flexible drive shaft 132 and a bone cutting drill bit 134. The drill bit 134 is placed through the guide tube 116 to form a bore 136 in bone at a location adjacent to a soft tissue repair. It is envisioned the bore 136 can be placed under or adjacent the soft tissue repair.

Figure 28:
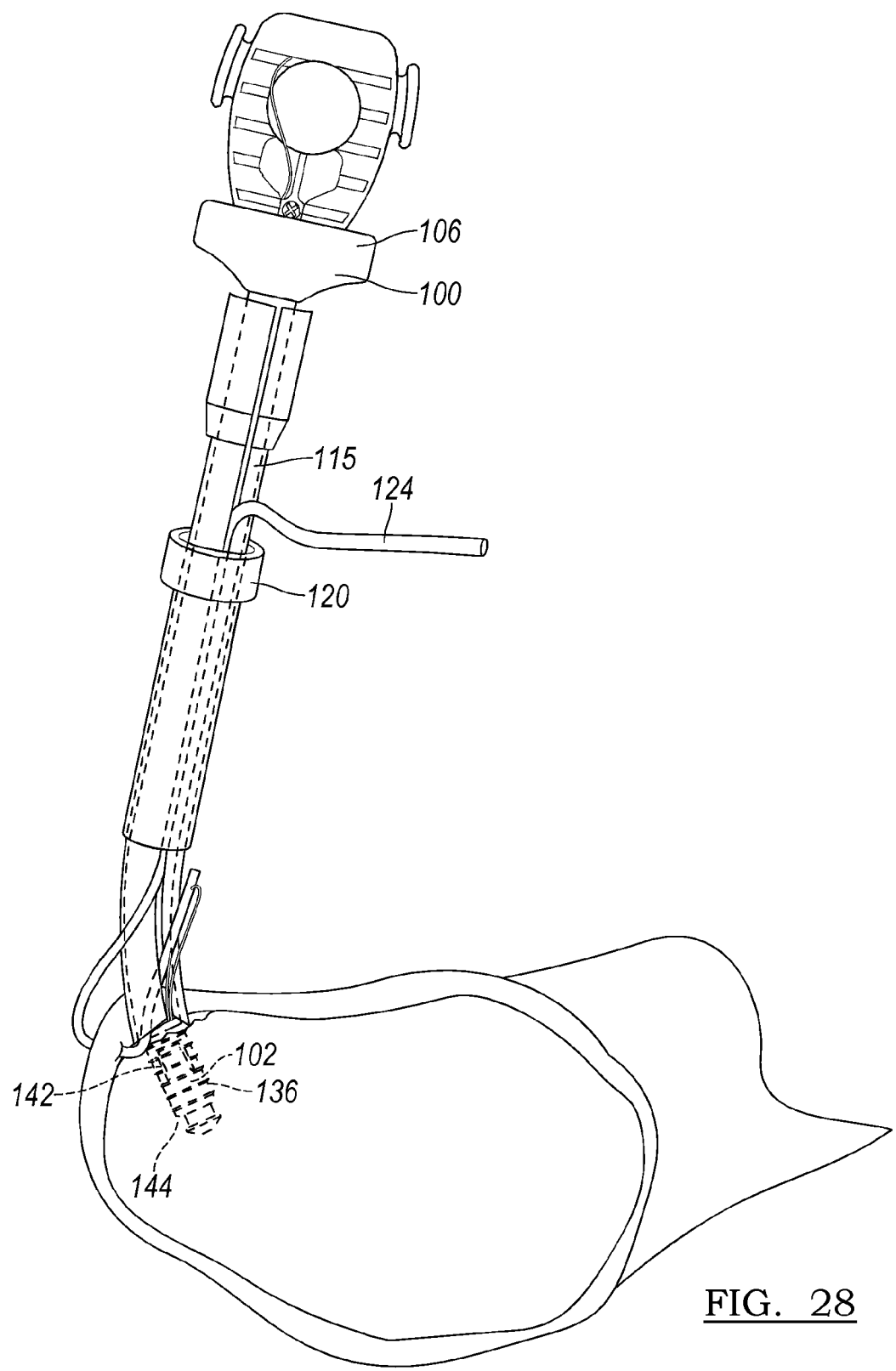
Figure 29:
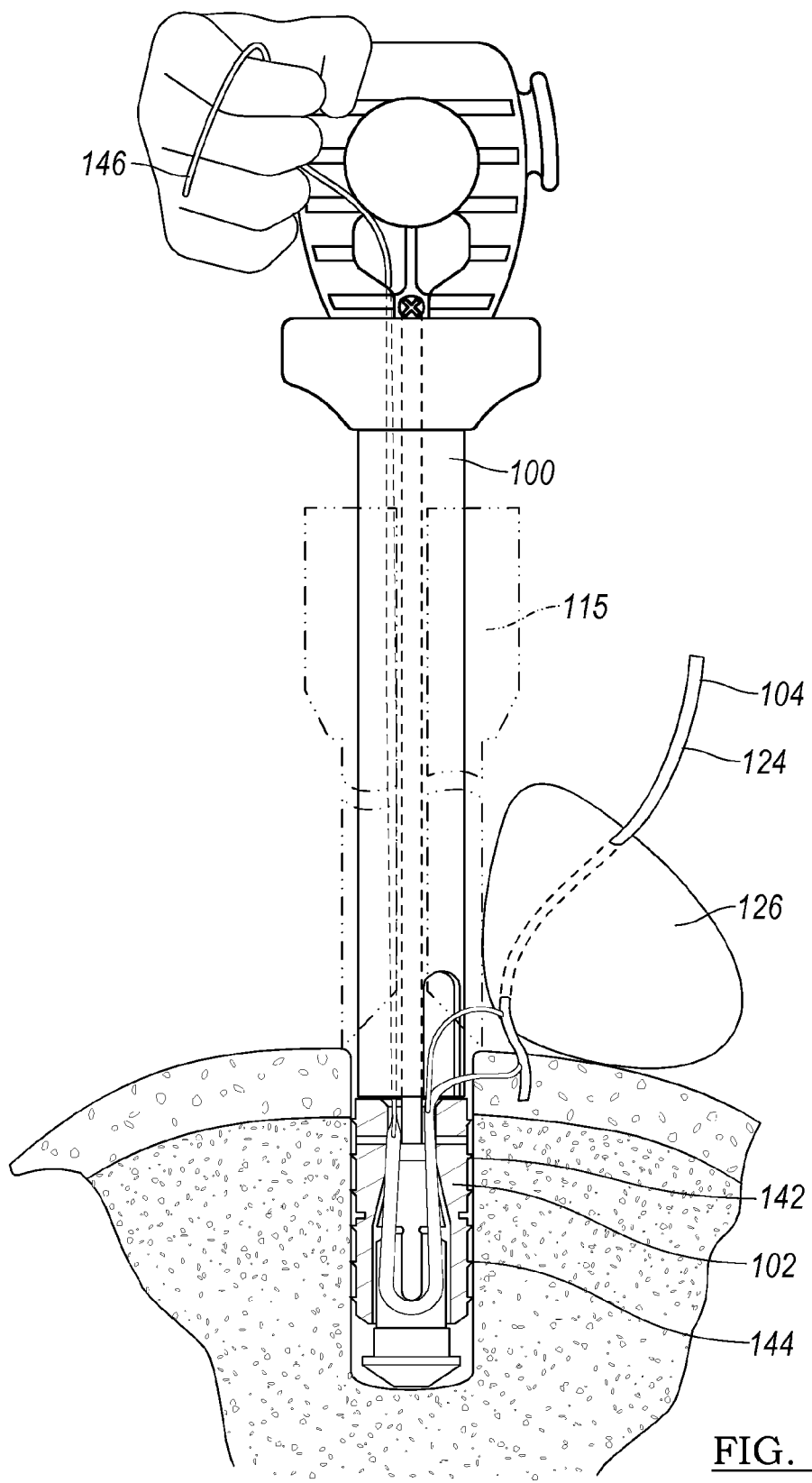

After the bore 136 has been formed in the bone, the tool 100, fastener 102, and associated soft tissue anchor 104 are placed through the insertion guide 115. As shown in FIG. 28, the fastener is inserted into the bore 136. It is envisioned the fastener 102 can be a two-part fastener having a first insertion portion 140 and a locking portion 142. The locking portion 142 can have a plurality of expandable bone engaging members 144.

Figure 30:
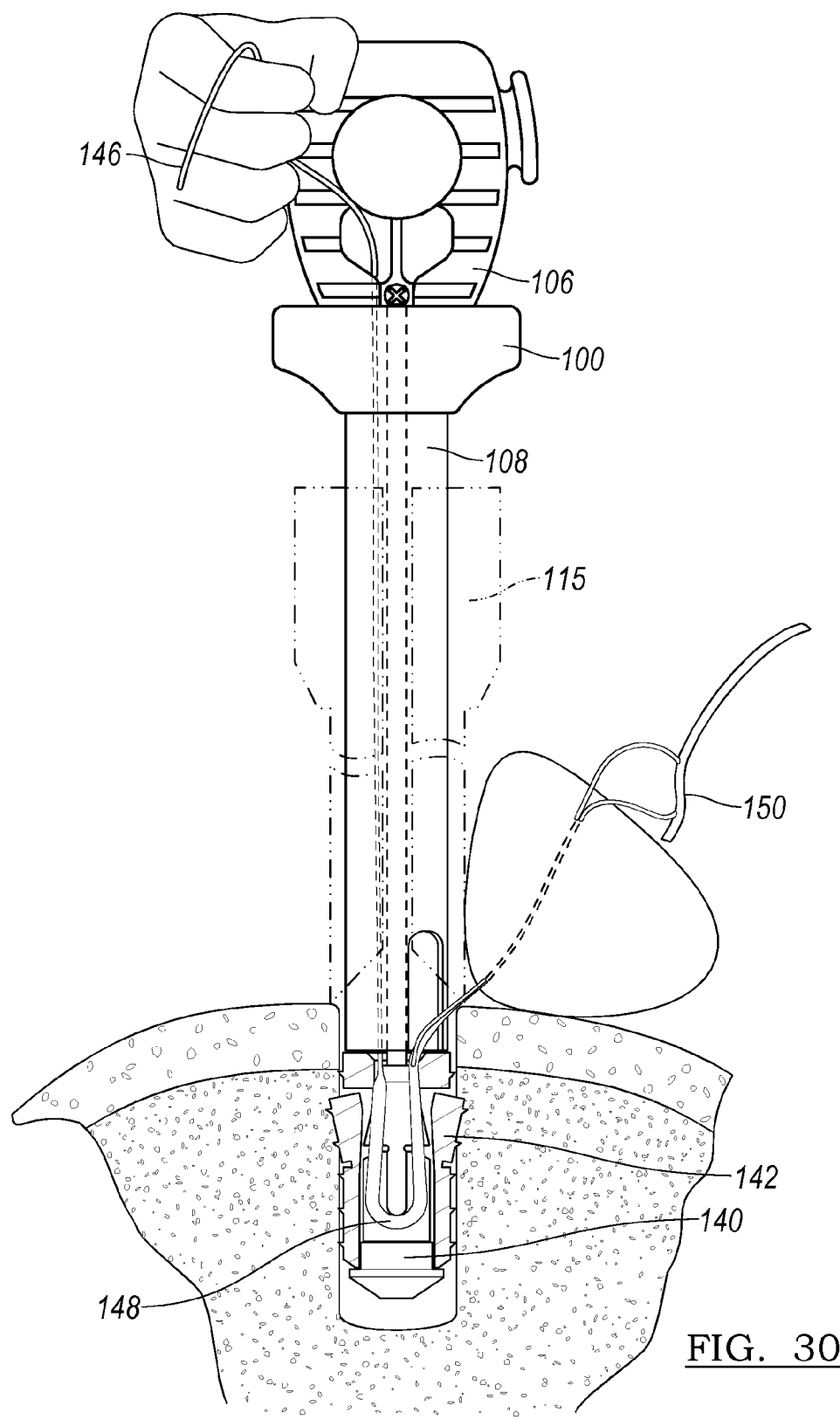

As seen in FIG. 30, the pair of sutures 146 can be pulled through the soft tissue 126. The sutures 146 can be coupled together using a suture construction shown in FIG. 1A or 1B. In this regard, the suture 146 can be looped through an integrally formed collapsible member or tube 148 which can be used to fix the suture construction with respect to either the insert or locking portion 140, 142 of the fastener.

Figure 31:
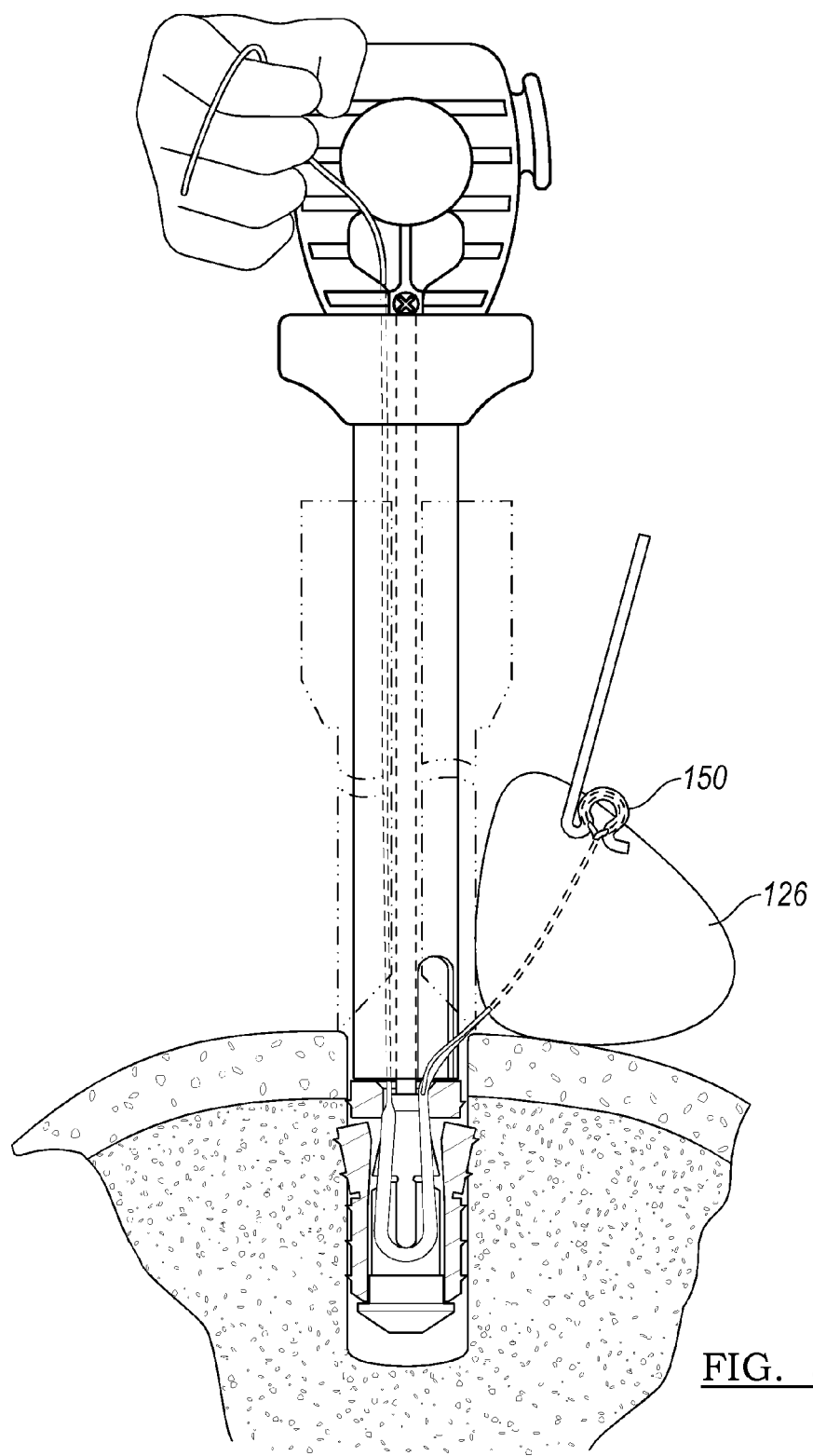
Figure 32:
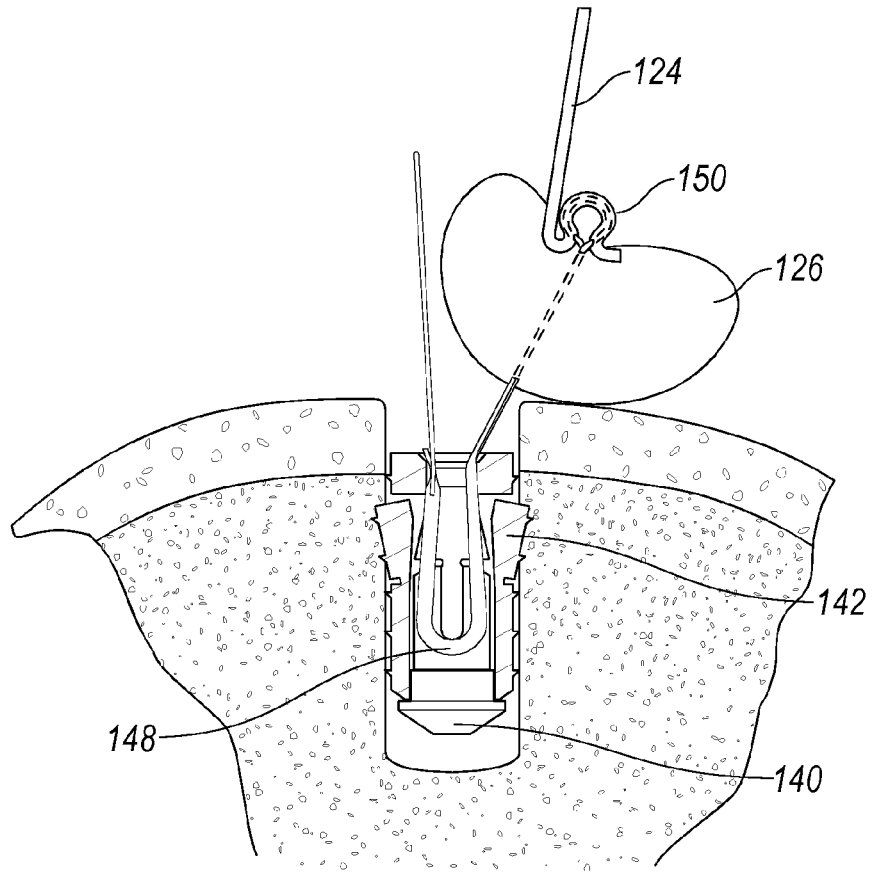
FIGS. 32-38 represent alternate methods for tying a suture anchor to the fastener.
Figure 33A:
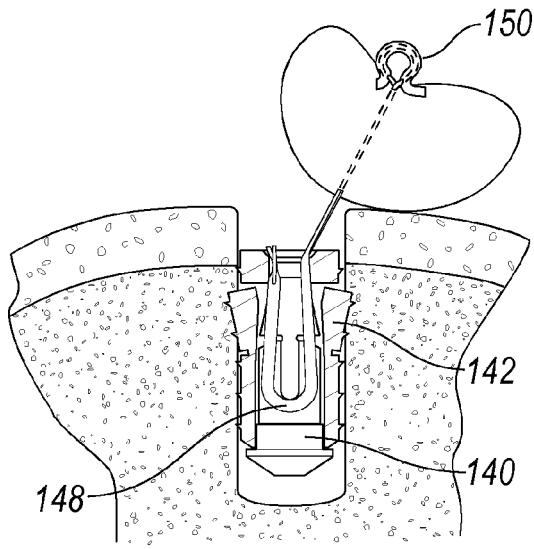
Figure 33B:
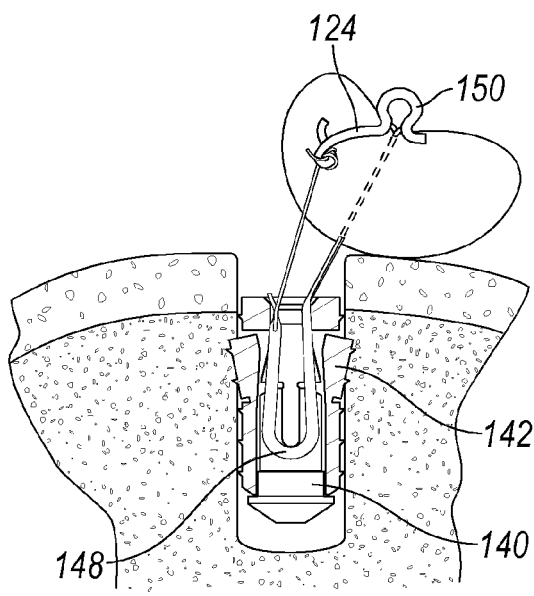

As shown in FIG. 31, when tension is applied to the suture 146 through the tool 100, a collapsible portion 150 of the collapsible tube engages the soft tissue 126. As seen in FIGS. 32-33B, once the collapsible portion 150 of the collapsible tube is set, the tool 100 can be removed from the insertion guide 115. At this point, the end of the longitudinal tube can be removed, or can be tied to the suture 146.

Figure 34:
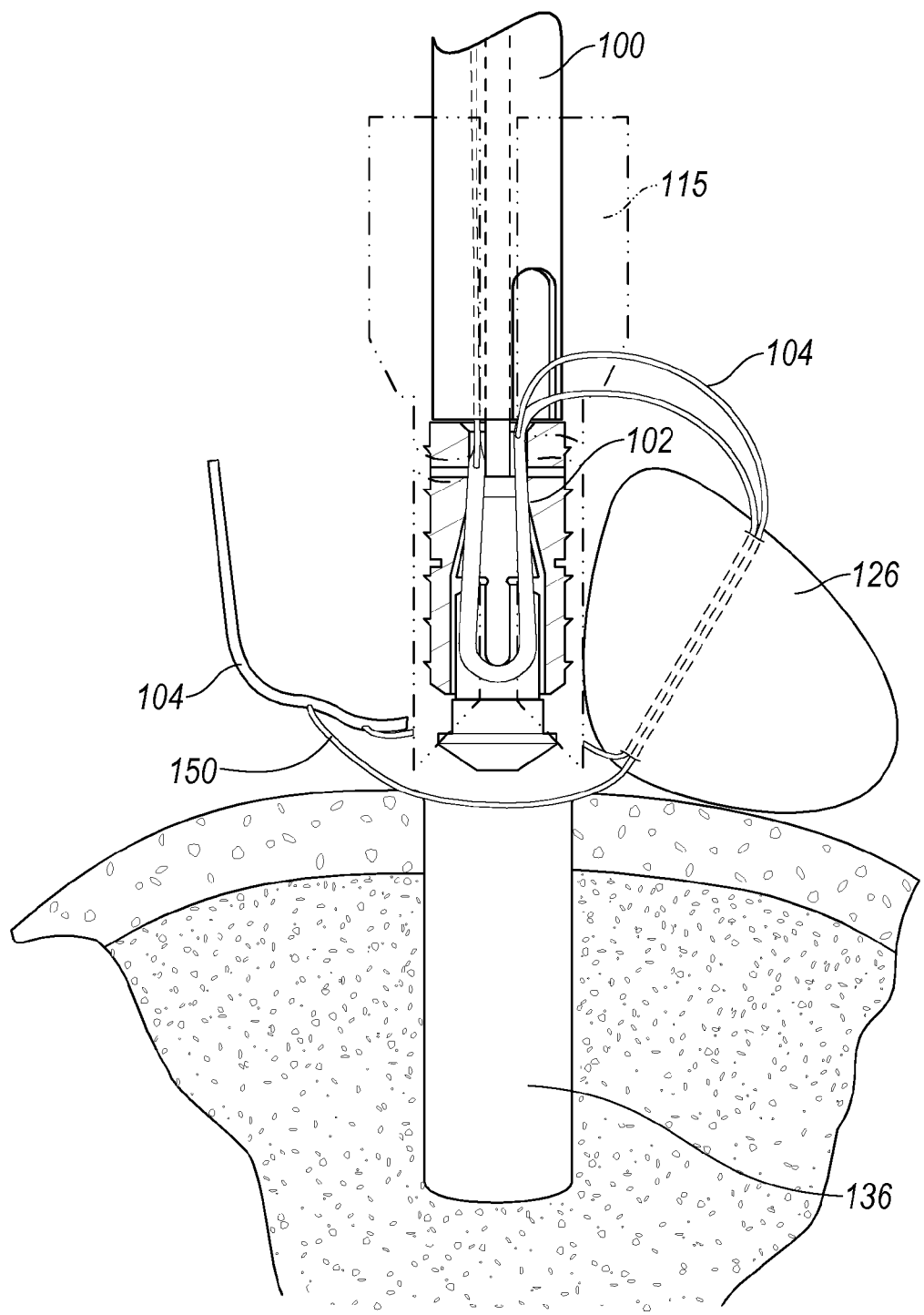
Figure 35:
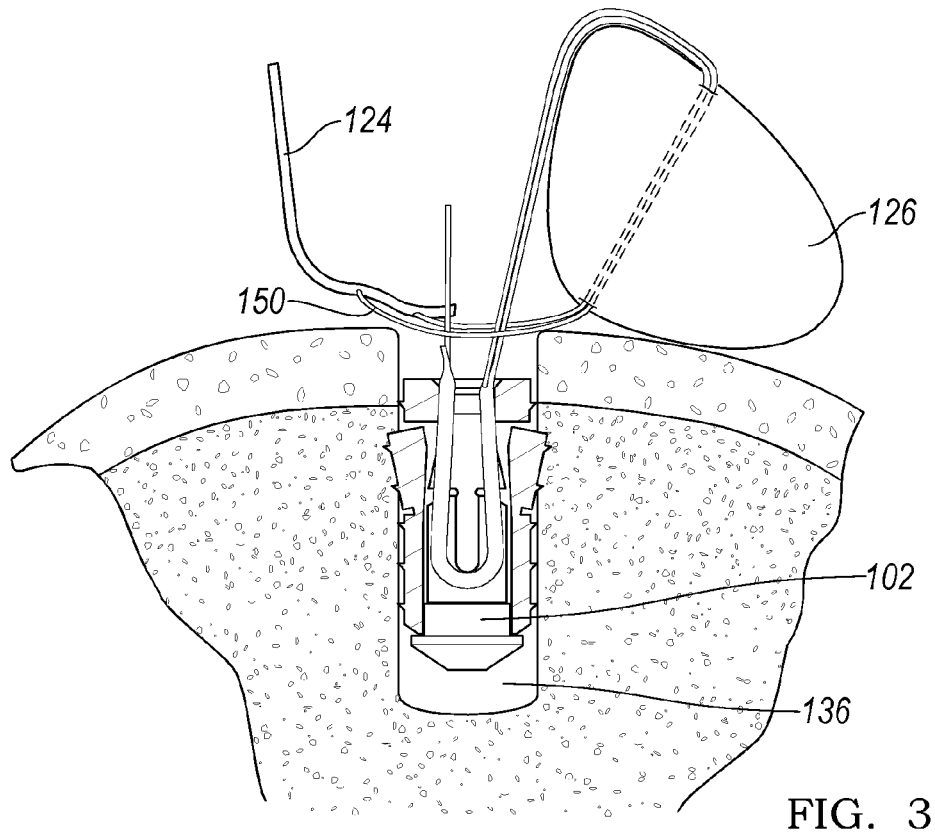
Figure 36:
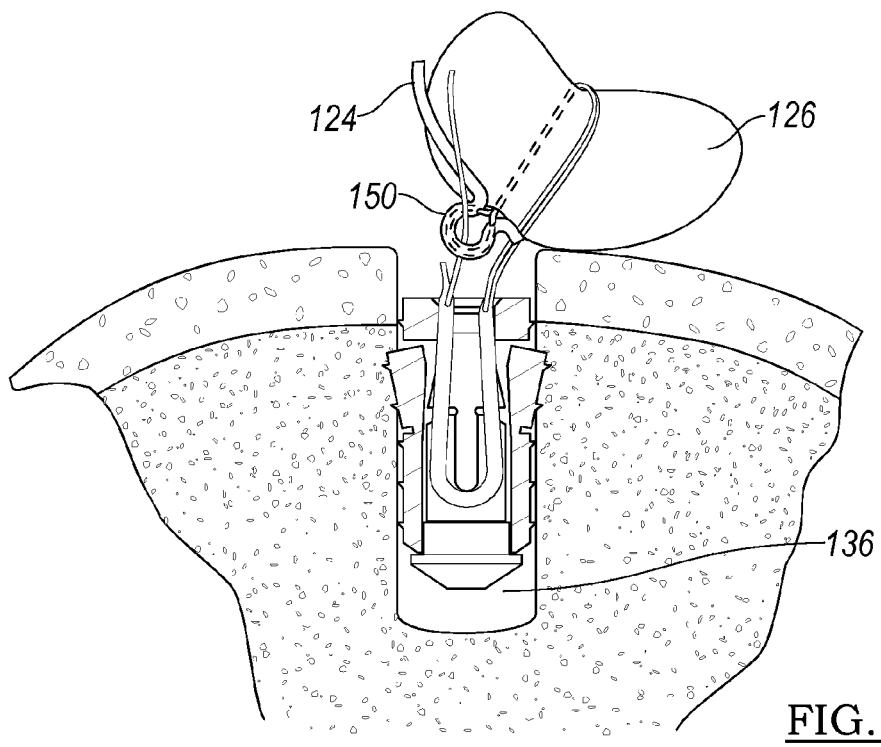

FIGS. 34-36 represent an alternate method for coupling a suture construction 104 to the fastener 102. Shown is a fastener 102 being passed through the loop of the suture. In this regard, the fastener 102 is passed through the loop of the suture prior to insertion of the fastener 102 within the bore 136 in the bone. After removal of the tool 100, tension is applied to the ends of the suture to constrict the collapsible portion 150 of the collapsible tube. This tensioning pulls the soft tissue 146 into a position with respect to the fastener 102.

Figure 37:
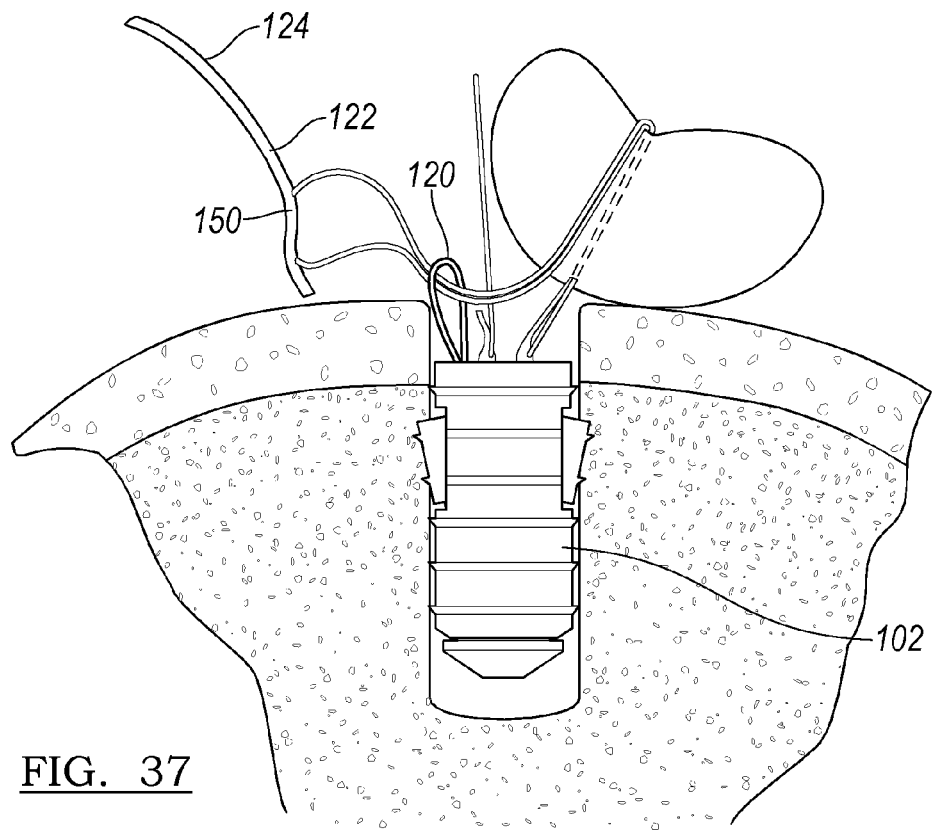
Figure 38:
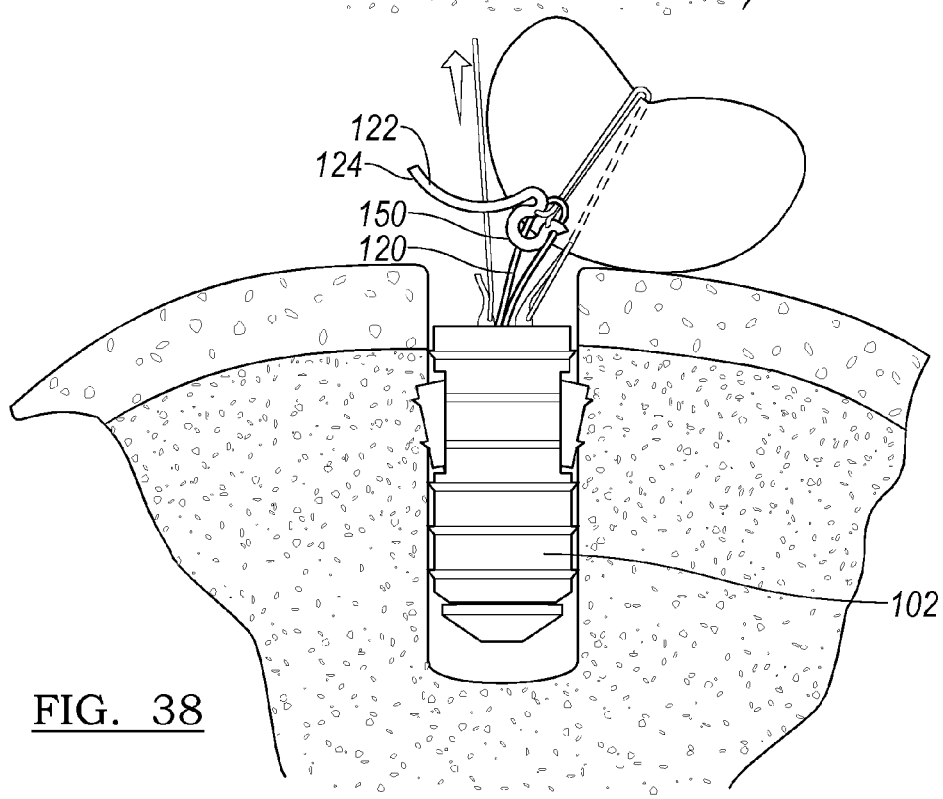

As shown in FIGS. 37 and 38, the fastener 102 can have an associated integral loop 120. The integral loop 120 can be a suture or can be an integral polymer construction. The compressible tube 122 can be threaded through the integral loop 120. Application of tension onto the suture causes the collapsible portion 150 of the collapsible tube to bear against the integral loop 120 and the soft tissue. It is envisioned the integral loop can be elastically deformable or can be fixed with respect to the fastener.

Figure 39:
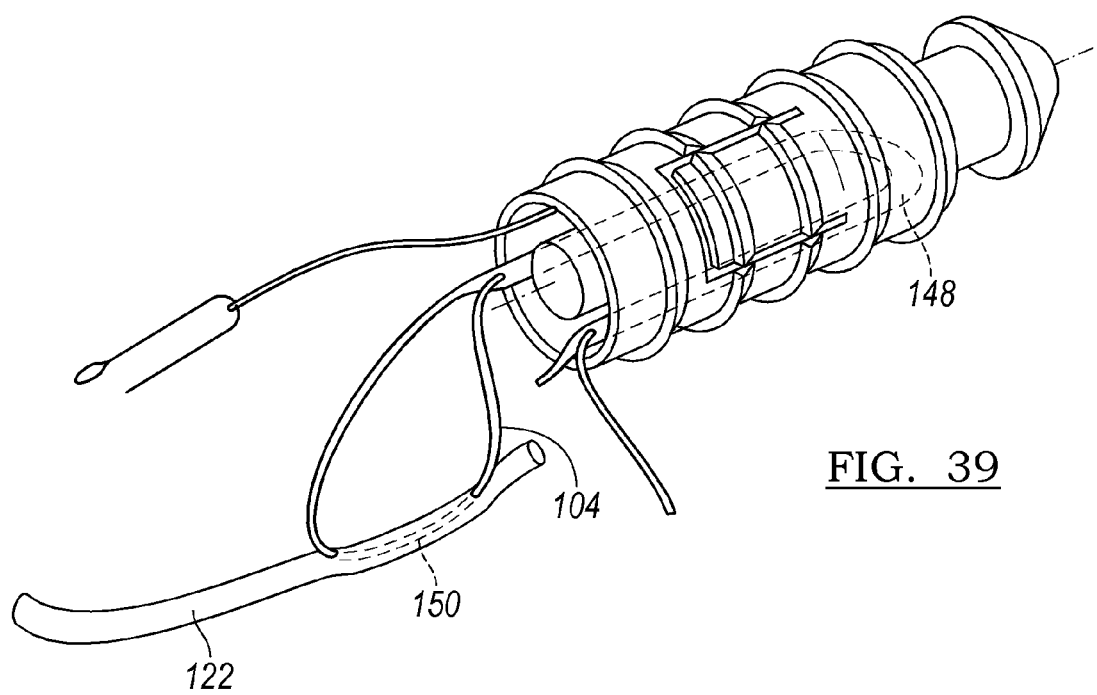
FIG. 39 represents the suture anchor coupled to a two-piece fastener.

FIG. 39 represents a suture construction coupled to a two-piece fastener 102. The suture construction 104 can be threaded through the aperture formed within the first or second portions of the fastener 102. As shown, an integrally formed collapsible tube portion 148 can be disclosed within the aperture of the fastener. Upon application of tension onto the suture, the tension will cause the collapse of this second collapsible tube portion 148, thus locking the suture to the fastener body 102.

FIGS. 40-44 represent an alternative system and method of coupling soft tissue to bone. By way of non-limiting example, a fastener 102 can be coupled to the bone as described above and shown in FIGS. 23-30. Subsequent to this, the collapsible portion 150 of the tube 104 can be passed through the soft tissue 126.

Figure 40:
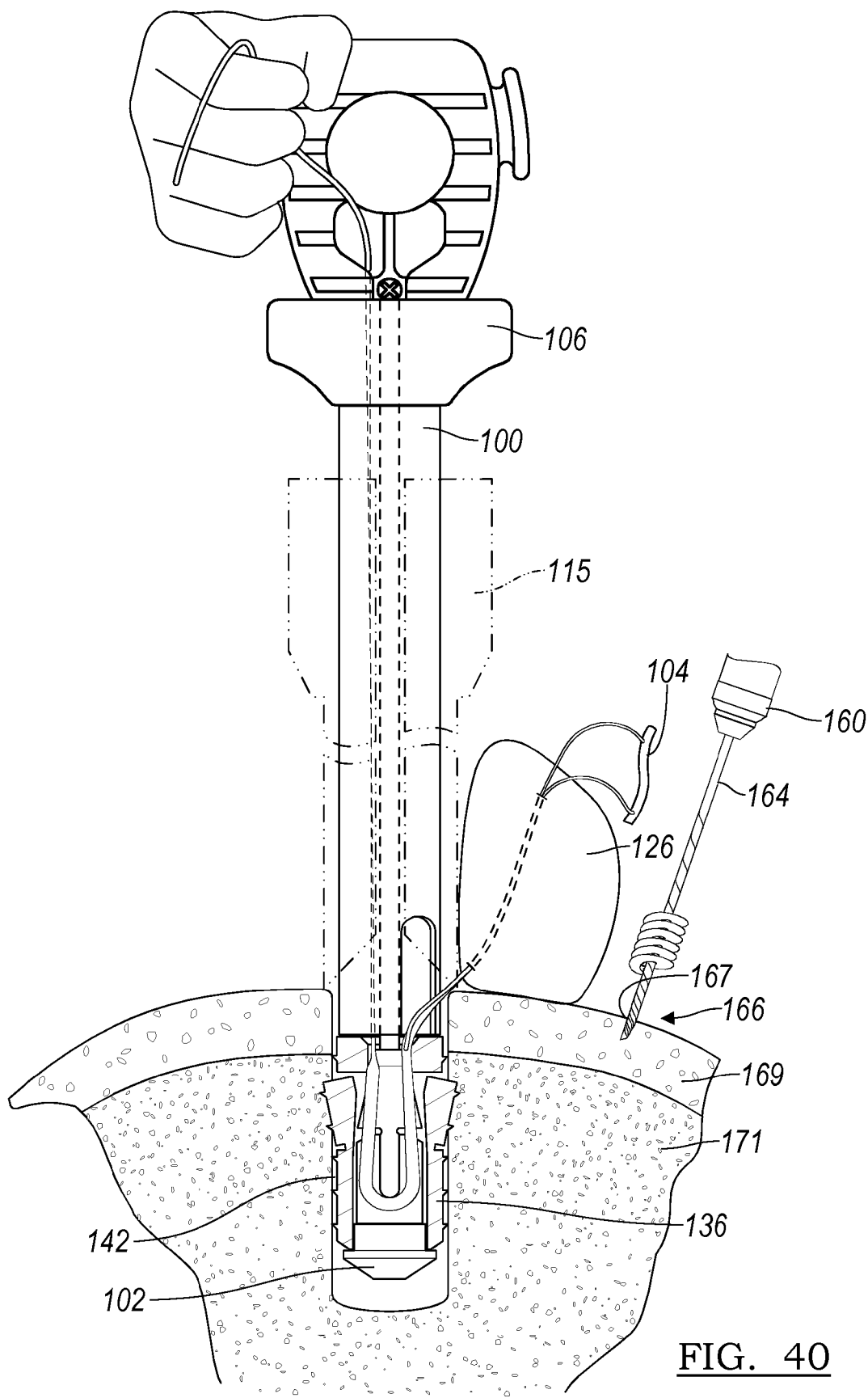
FIGS. 40-44 represent an alternate system and method of coupling soft tissue to the bone.
Figure 41:
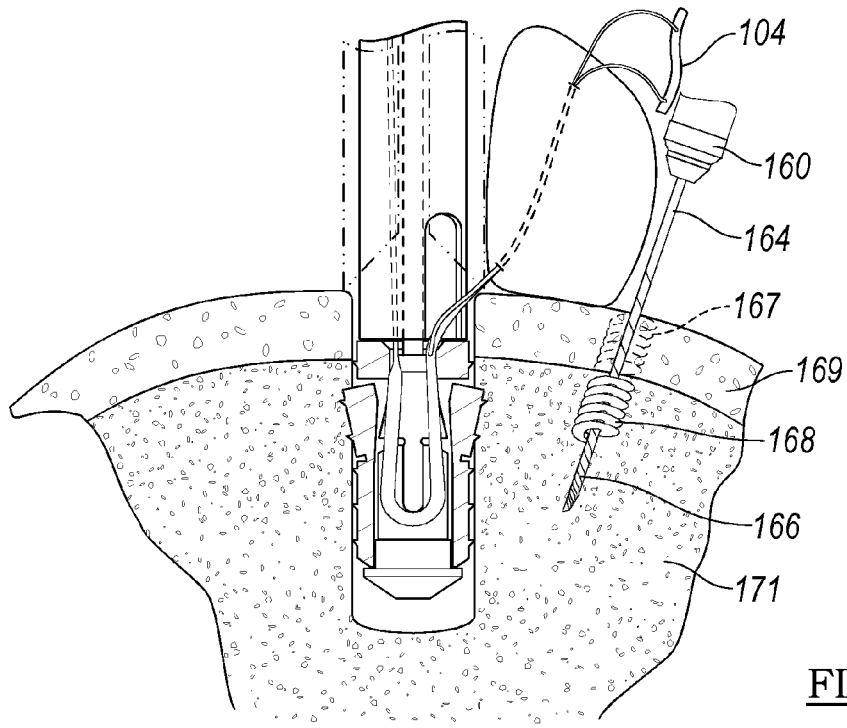
Figure 42:
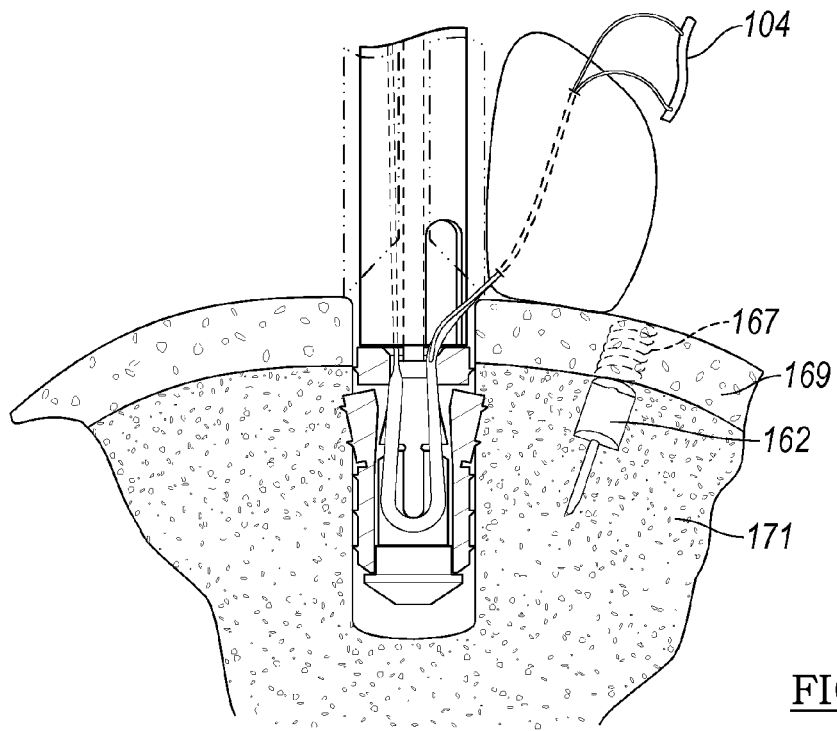

As best seen in FIGS. 40-42, a drive tool 160 is used to form a soft tissue engagement site 162 in a bone structure. The tool 160 has a drive (not shown) which rotates a bone cutting bit 164. The bone cutting bit 164 has a first portion 166 configured to drill a hole 167 through cortical bone and a threaded second portion 168. The threaded second portion 168 is configured to cut threads in the cortical 169 and cancellous bone 171 structures. This is accomplished by advancing the cutting bit 164 into the bone at a predetermined rate while rotating the bit at a predetermined speed. As shown in FIG. 41, after the second portion 168 has entered the cancellous bone 171, the bit is rotated while keeping the rotating tool 160 in a substantially stationary position. The thread cutting threads of the second portion 168 then displace cancellous bone 171, forming the cavity 162. The bit is removed by rotating the thread cutting threads through the threads formed in the cortical bone 169.

Figure 43:
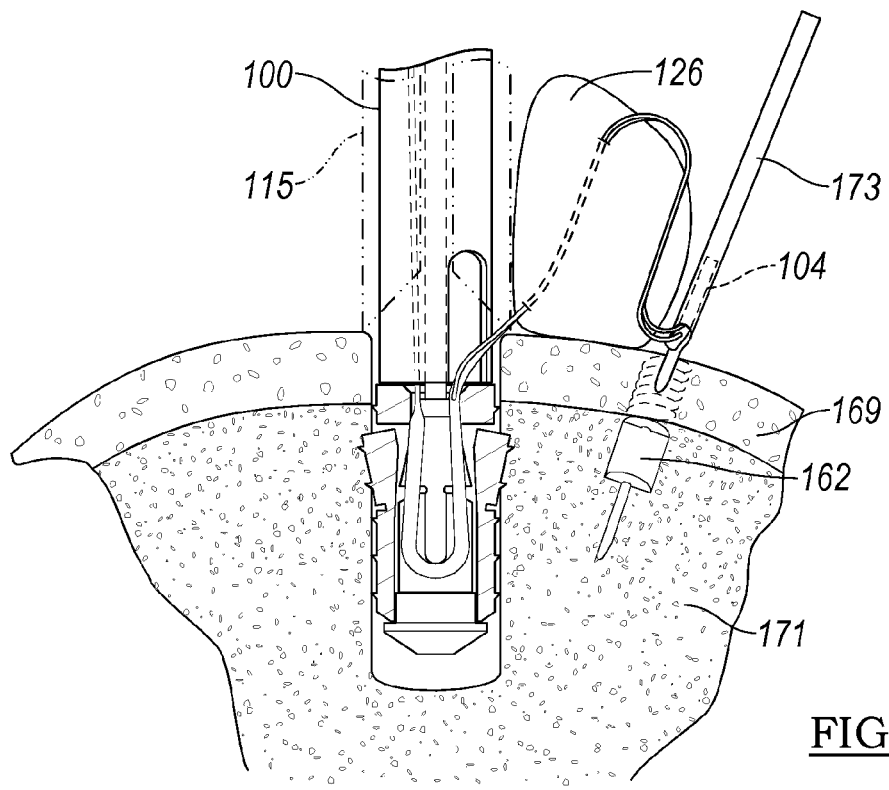
Figure 44:
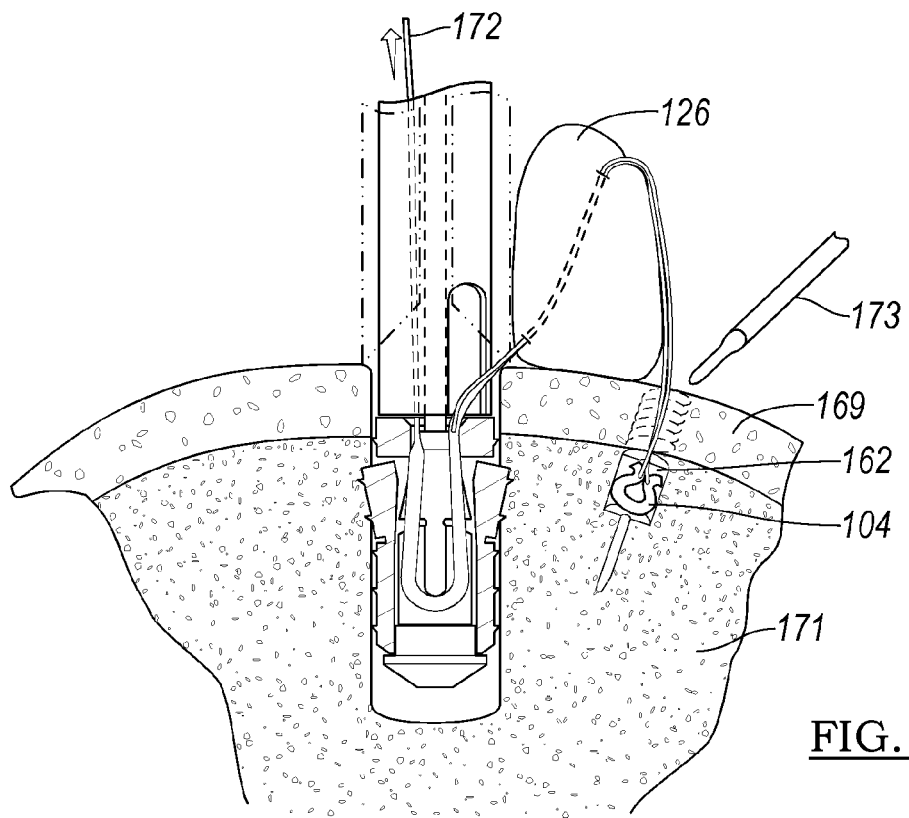

As shown in FIG. 43, the collapsible tube 104 of suture anchor is passed through passage 167 and into the cavity 162. In this regard, an insertion tool 173 can be used to insert the collapsible tube 104 into the cavity 162. As shown in FIG. 44, tension is applied to the end 172 of the suture anchor, thus causing the collapsible portion 104 of the anchor.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Further, the suture material and collapsible tubes can be formed of resorbable material. Such variations are not to be regarded as a departure from the spirit and scope of the invention.

What is claimed is:

1. A method for use in surgically implanting a flexible strand comprising:

passing the flexible strand through a bore defined by a first construct;

passing a first end of the flexible strand through a first aperture defined by the flexible strand into a passage portion defined by the flexible strand and out a second aperture defined by the flexible strand so as to place the first end outside of the passage portion and form a first loop;

coupling the first construct to a patient;

forming a hole in soft tissue;

passing the first loop through the hole; and applying tension to at least one end to constrict the first loop pulling soft tissue toward the first construct.

2. The method according to claim 1 further comprising passing the first end through the hole.

3. The method according to claim 1 wherein the first loop is coupled to a fastening member.

4. The method according to claim 3 wherein a second loop is coupled to the construct.

5. The method according to claim 1 further comprising passing a second end of the flexible strand through a third aperture into the passage portion and out a fourth aperture so as to place the second end outside of the passage portion and form a second loop; and positioning the passage portion within the bore.

6. The method according to claim 5 further comprising coupling a collapsible fabric member disposed about one of the first or second loops.

7. The method according to claim 5 wherein the flexible strand comprises a collapsible fabric tube disposed about the first and second loops.

8. The method according to claim 1 wherein the flexible strand is a suture.

9. A method for use in surgically implanting a suture comprising:

passing the suture through an aperture defined by a first bone engaging member, where a first end of the suture is passed through a first aperture defined by the suture into a passage portion defined by the suture and out a second aperture defined by the suture so as to place the first end outside of the passage portion and form a first loop, and where a first collapsible tube is threaded onto the first loop;

coupling the first bone engaging member to a patient; and applying tension on at least one of the first end or a second end to constrict the first loop against patient soft tissue.

10. The method according to claim 9 further comprising forming a hole through the soft tissue and passing a portion of the suture through the hole.

11. The method according to claim 9 further comprising passing the first collapsible tube through the first hole.

12. The method according to claim 5 wherein the third aperture is the second aperture and the fourth aperture is the first aperture.

13. The method according to claim 5, wherein passing a first end of the flexible strand through a first aperture defined by the flexible strand into a passage portion defined by the flexible strand and out a second aperture defined by the flexible strand so as to place the first end outside of the passage portion and form a first loop includes forming the first loop about a first end of the passage portion; and wherein passing a second end of the flexible strand through a third aperture into the passage portion and then out a fourth aperture so as to place the second end outside the passage portion and form a second loop includes forming the second loop about a second opposite end of the passage portion.

14. The method according to claim 13, wherein applying tension to at least one end to constrict the first loop pulling soft tissue toward the first construct includes applying tension to first and second ends of the flexible strand to reduce a size of the first and second loops and draw the soft tissue to the first construct.

15. A method for use in surgically implanting a suture comprising:
    forming a first hole in soft tissue;
    forming a second hole in soft tissue spaced apart from the first hole;
    forming a bore in a bone of a patient;
    positioning a fixation member in the bore of the bone, the fixation member having an adjustable flexible member construct extending therefrom;
    positioning a first adjustable loop of the flexible member construct through the first hole in the soft tissue, where the first loop includes a first collapsible tube coupled thereto;
    positioning a second adjustable loop of the flexible member construct through the second hole in the soft tissue, where the second loop includes a second collapsible tube coupled thereto; and
    applying tension to first and second ends of the flexible member construct to reduce a size of the first and second loops and couple the soft tissue to the bone.

16. The method according to claim 15, wherein positioning a first adjustable loop of the flexible member construct through the first hole in the soft tissue, where the first loop includes a first collapsible tube coupled thereto includes positioning the first collapsible tube through the first hole; and
    positioning a second adjustable loop of the flexible member construct through the second hole in the soft tissue, where the second loop includes a second collapsible tube coupled thereto includes positioning the second collapsible tube through the second hole.

17. The method according to claim 15, wherein applying tension to first and second ends of the flexible member construct to reduce a size of the first and second loops and couple the soft tissue to the bone includes applying tension to the first and second ends to constrict the first and second collapsible tubes against the soft tissue.

18. A method for use in surgically implanting a flexible strand comprising:
    passing the flexible strand through an aperture defined by a first bone engaging member;
    passing a first end of the flexible strand through a first aperture defined by the flexible strand into a passage portion defined by the flexible strand and out a second aperture defined by the flexible strand so as to place the first end outside of the passage portion and form a first adjustable loop;
    passing a second end of the flexible strand through the second aperture into the passage portion and then out the first aperture so as to place the second end outside the passage portion and form a second adjustable loop;
    coupling a first collapsible tube to the first loop; and
    coupling a second collapsible tube to the second loop.

19. The method according to claim 18 further comprising coupling a first cinch loop between the first collapsible tube and the first adjustable loop; and coupling a second cinch loop between the second collapsible tube and the second adjustable loop.

20. The method according to claim 18, wherein coupling a first collapsible tube to the first loop and a second collapsible tube to the second loop includes threading a pair of first collapsible tubes through the first loop and threading a pair of second collapsible tubes through the second loop.

21. The method according to claim 18, wherein forming a first hole through the soft tissue and passing the first collapsible tube though the first hole includes forming a first pair of holes spaced apart from each other through the soft tissue and passing the pair of first collapsible tubes through the respective first pair of holes; and
    wherein forming a second hole through the soft tissue spaced apart from the first hole and passing the second collapsible tube through the second hole includes forming a second pair of holes spaced apart from each other and the first pair of holes through the soft tissue and passing the pair of second collapsible tubes through the respective second pair of holes.

22. The method according to claim 18, wherein passing the flexible strand through an aperture defined by a first bone engaging member includes positioning the passage portion within the aperture defined by the first bone engaging member.

23. The method according to claim 18, further comprising:
    coupling the first bone engaging member to a bone of a patient;
    forming a first hole through soft tissue and passing the first collapsible tube though the first hole;
    forming a second hole through the soft tissue spaced apart from the first hole and passing the second collapsible tube through the second hole; and
    applying tension on the first and second ends to constrict the first and second loops against the soft tissue.

* * * * *

UNITED STATES PATENT AND TRADEMARK OFFICE
CERTIFICATE OF CORRECTION

| | | |
|---|---|---|
| PATENT NO. | : 8,088,130 B2 | Page 1 of 1 |
| APPLICATION NO. | : 12/474802 | |
| DATED | : January 3, 2012 | |
| INVENTOR(S) | : Ryan A. Kaiser et al. | |

It is certified that error appears in the above-identified patent and that said Letters Patent is hereby corrected as shown below:

Title Page No. (56) References Cited, U.S. Patent Documents, Page 2, Column 1, Reference 57
Replace "RE26,501 12/1968 Kendrick et al." with --RE26,501 12/1968 Himmelstein et al.--

Column 2,
Line 45, replace "A first" with --First--

Column 4,
Line 8, after "either" delete "a"

Column 4,
Line 61, replace "FIG. 11b" with --FIG. 11B--

Column 12,
Line 22, replace "though" with --through--

Column 12,
Line 42, replace "though" with --through--

Signed and Sealed this
Seventh Day of August, 2012

David J. Kappos
*Director of the United States Patent and Trademark Office*